US012727905B2

(12) United States Patent
Tani et al.

(10) Patent No.: US 12,727,905 B2
(45) Date of Patent: Sep. 8, 2026

(54) CUTTING DEVICE, FORCEPS AND GRIPPING/CUTTING METHOD

(71) Applicant: NATIONAL UNIVERSITY CORPORATION SHIGA UNIVERSITY OF MEDICAL SCIENCE, Shiga (JP)

(72) Inventors: Tohru Tani, Shiga (JP); Shigeyuki Naka, Shiga (JP); Atsushi Yamada, Shiga (JP); Tsuyoshi Nakakubo, Kyoto (JP)

(73) Assignee: NATIONAL UNIVERSITY CORPORATION SHIGA UNIVERSITY OF MEDICAL SCIENCE, Shiga (JP)

( * ) Notice: Subject to any disclaimer, the term of this patent is extended or adjusted under 35 U.S.C. 154(b) by 1079 days.

(21) Appl. No.: 17/554,386

(22) Filed: Dec. 17, 2021

(65) Prior Publication Data

US 2022/0175410 A1 Jun. 9, 2022

Related U.S. Application Data

(63) Continuation-in-part of application No. PCT/JP2020/023914, filed on Jun. 18, 2020.

(Continued)

(51) Int. Cl.
*A61B 17/3201* (2006.01)
*A61B 17/00* (2006.01)

(Continued)

(52) U.S. Cl.
CPC ...... *A61B 17/3201* (2013.01); *A61B 17/2804* (2013.01); *A61B 17/29* (2013.01);

(Continued)

(58) Field of Classification Search
CPC . A61B 17/3201; A61B 17/2804; A61B 17/29; A61B 2017/00367;

(Continued)

(56) References Cited

U.S. PATENT DOCUMENTS 4,476,862 A * 10/1984 Pao .................... A61B 18/1402 606/50
5,211,655 A * 5/1993 Hasson .............. A61B 17/2909 606/205

(Continued)

FOREIGN PATENT DOCUMENTS

JP 2015-16347 A 1/2015
JP 2017-060845 A 3/2017

(Continued)

OTHER PUBLICATIONS

International Search Report issued in PCT/JP2020/023914 mailed on Sep. 1, 2020 with English Translation (6 pages).

(Continued)

*Primary Examiner* — Tan-Uyen T Ho
*Assistant Examiner* — Bridget E. Rabaglia
(74) *Attorney, Agent, or Firm* — Greenblum & Bernstein, P.L.C.

(57) ABSTRACT

A cutting device including a first contact member and at second contact member assembled so as to be openable and closable, a contact mechanism that rotates the first contact member toward the second contact member to bring the first contact member and the second contact member into contact with a target portion, and a cutting mechanism for cutting the target portion in a state where the first contact member and the second contact member are in contact with the target portion by the contact mechanism.

21 Claims, 49 Drawing Sheets

Related U.S. Application Data

(60) Provisional application No. 62/864,224, filed on Jun. 20, 2019.

(51) Int. Cl.
*A61B 17/28* (2006.01)
*A61B 17/29* (2006.01)
*A61B 34/30* (2016.01)

(52) U.S. Cl.
CPC .... *A61B 34/30* (2016.02); *A61B 2017/00367* (2013.01); *A61B 2034/305* (2016.02)

(58) Field of Classification Search
CPC ...... A61B 2018/00607; A61B 18/1445; A61B 2018/1455; A61B 2018/1457; A61B 2017/2936; A61B 17/285; A61B 2017/2901; A61B 2017/2903; A61B 2017/2904; A61B 2017/2905; A61B 2017/2906; A61B 2017/2908; A61B 17/2909; A61B 2017/291; A61B 2017/2912; A61B 2017/292; A61B 2017/2922; A61B 2017/2924; A61B 2017/2926; A61B 2017/2932; A61B 2017/294; A61B 2017/2941; A61B 2017/2944; A61B 2017/2946; A61B 2017/2947; A61B 17/295; A61B 2018/00601; A61B 2018/0063
See application file for complete search history.

(56) References Cited

U.S. PATENT DOCUMENTS 6,743,230 B2 * 6/2004 Lutze ................. A61B 18/1445 606/205
8,974,479 B2 * 3/2015 Ross .............. A61B 17/320092 606/169
2011/0087208 A1 4/2011 Boudreaux et al.
2011/0087209 A1 4/2011 Boudreaux et al.
2011/0087218 A1 4/2011 Boudreaux et al.
2011/0087219 A1 4/2011 Boudreaux et al.
2011/0087220 A1 4/2011 Felder et al.
2016/0058460 A1 3/2016 Ohki
2019/0167342 A1 * 6/2019 Hancock ............ A61B 18/1447

FOREIGN PATENT DOCUMENTS

JP 2017-060846 A 3/2017
WO 2014/103096 A1 7/2014
WO WO 2019/073036 A2 4/2019

OTHER PUBLICATIONS

Extended European search report issued on counterpart European application No. 20826037.2 dated Jun. 7, 2023.

* cited by examiner (a)
(b)
(c)
1
10
12
13
13a
14
15
16
17
11
111
112
112 (11)
113
114
115, 132
116
117, 141
118
121, 133
122
122, 142
123
131
143
153
24a
24b
24c
24a, 24b
L
F
R (a)
(b)
(c)
10
15
24c
153
143
14(17)
24a
24b
116(17)
17
14
116
122
142
117
B
40
41
42
43
44
30

Figure 48:
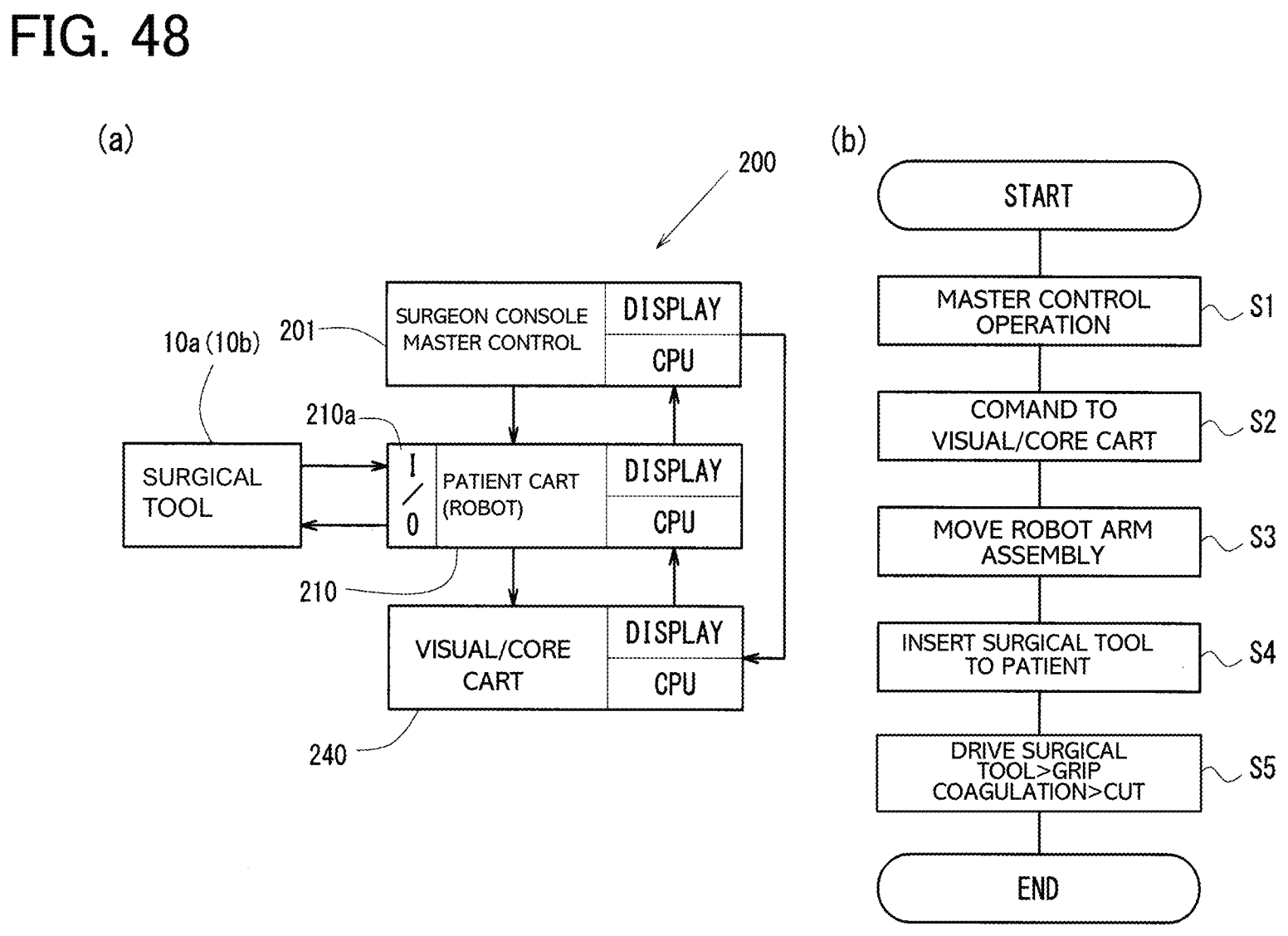

SURGEON CONSOLE MASTER CONTROL
DISPLAY
CPU
201

PATIENT CART (ROBOT)
DISPLAY
CPU
I / O
210a
210

VISUAL/CORE CART
DISPLAY
CPU
240

SURGICAL TOOL
10a (10b)

(b)

START

S1 MASTER CONTROL OPERATION

S2 COMAND TO VISUAL/CORE CART

S3 MOVE ROBOT ARM ASSEMBLY

S4 INSERT SURGICAL TOOL TO PATIENT

S5 DRIVE SURGICAL TOOL>GRIP COAGULATION>CUT

END

MOVABLE PART
MOPERATION RELEVANCE
OPERATION
FUNCTION
UPPER JAW
LOWER JAW
COAGULAT-ION BUTTON
CUTTER
(CLOSE ALL)
(GRIP)
(PUSH)
(RELEASE)
(CUT IN)
(RELEASE)
(OPEN)
DRILLING
GRIPPING
COAGULATING
CUTTING
OPENING

CUTTING DEVICE, FORCEPS AND GRIPPING/CUTTING METHOD

CROSS REFERENCE TO RELATED APPLICATION

This application is a continuation-in-part application of International Patent Application No. PCT/JP2020/023914 (filed on Jun. 18, 2020), which claims the benefit of priority from U.S. Provisional Application No. 62/864,224 (filed on Jun. 20, 2019 and now abandoned). This application also claims the benefit of priority from Japanese Patent Application No. 2020-209292 (filed on Dec. 17, 2020).

The entire contents of the above applications, which the present application is based on, are incorporated herein by reference.

BACKGROUND OF THE INVENTION

1. Field of the Invention

The present invention relates to a cutting device, forceps and gripping/cutting method, in particular, a gripping/cutting device that abuts on a target site, grips, crashes and/or cuts, forceps is capable of contacting (gripping), incision, peeling, coagulation (hemostasis), cutting surgery, a portable surgical device, and surgery related systems, medical systems, surgical medical operation robots, and gripping/cutting methods.

2. Description of the Related Art

For example, the basic operation in extraction surgery is a repetition of gripping, coagulation (hemostasis), and amputation following dissection. With known forceps, when the biological tissue (target site) is griped or cut, the contact point that comes into contact with the biological tissue (target site) by a two-step operation or the electrode provided on the cutting blade is applied to the target site. On the other hand, it is irradiated with high-frequency electromagnetic waves to coagulate or cut.

In the hemostatic operation during surgery, although the blood is coagulated by irradiating electromagnetic waves (high radio frequencies such as microwaves) from the electrodes, the hemostatic power is weakened in a liquid, a water pool, or a blood pool.

SUMMARY OF THE INVENTION

The present invention provides a cutting device that may contact (abut) a target site, and grip, crash, coagulate and cut the target site (portion) by a series of operations, and further, forceps, surgical systems, medical systems, robots, and surgical medical operation robots that may contact (abut) and cut the target site by a series of operations, According to an example of the present invention, there is provided a cutting device including a first contact member and a second contact member assembled so as to be openable and closable, a contact mechanism that rotates the first contact member toward the second contact member to bring the first contact member and the second contact member into contact with a target site, and a cutting mechanism for cutting the target site in a state where the first contact member and the second contact member are in contact with the target site by the contact mechanism. The cutting mechanism may be provided with a cutting member, in which the cutting member is rotated in the same direction as the rotational drive of the first gripping member, and is joined to the second gripping member to cut the target site.

Further, the first gripping member may be provided with a protrusion restricting portion for restricting the cutting member rotating in the same direction from protruding beyond the first gripping member in the direction opposite to the cutting direction. Further, in the cutting mechanism, the cutting member may be slid forward in parallel with the second gripping member to cut the target site by the cutting edge of the cutting member.

According to an example of the present invention, there is a forceps having the above described cutting device in which the target site is a living tissue, and the first gripping member and the second gripping member are a first jaw member and a second jaw member, respectively, including a driving mechanism that grips (or crash) and coagulates the biological tissue by rotating the first jaw member toward the second jaw member, and one operation member operating the driving mechanism and the cutting mechanism, wherein at least a part of the living tissue is coagulated by irradiating electromagnetic waves from the electrodes, and the biological tissue is gripped by the first jaw member and the second jaw member, and then cut by the cutting mechanism in accordance with a series of operations of the one operation member. The driving mechanism may be configured to grip, crash, and then coagulate the biological tissue for gripping, crashing, and coagulation.

The cutting device or the forceps may be configured to include electrodes for irradiating electromagnetic waves which are disposed to at least one of the gripping point that grips the target site in the first gripping member and the vicinity of the cutting blade in the cutting member, and the gripping point that grips the target site in the second gripping member. The electrodes may be branched and connected to a coaxial cable that supplies electromagnetic waves.

According to an example of the present invention, there are provided a method of rotating the first jaw member toward the second jaw member, and gripping or crashing a biological tissue by the first jaw member and the second jaw member, and a method of gripping a biological tissue, the electrode, in which the first jaw member is rotated toward the second jaw member and the first jaw member and the second jaw member, a coagulation method by irradiation with an electromagnetic wave, and a cutting method by the above-mentioned attached cutting member. The gripping method may be a method of gripping and/or crashing, and coagulating the body tissue.

According to an example of the present invention, there is provided a robot including an input/output unit connected to the cutting device or forceps by wire and/or wirelessly, an input unit that receives an operation signal in real time, and an arithmetic unit that executes a program of a predetermined operation based on the operation signal, and a drive that abuts on the target site and a predetermined operation based on the operation signal, and an output unit that generates a drive signal that abuts on the target site and/or cuts the target portion by the first contact member and the second contact member of the cutting device based on the output from the calculation unit. Further there is provided a cutting method having a robot arm movement, a tool movement, and a cutting step. A working limb of the robot is equipped with the cutting device having a microwave irradiation function on both blades of the cutting device.

According to an example of the present invention, there is provided medical tool including an end effector having a gripping mechanism and a cutting mechanism, and a driving unit for driving the end effector, and by driving the first gripping member, the second gripping member, and the cutting member in combination to selectively activate at least one of a gripping function, a crashing function, a coagulation function, a cutting function, and an opening/closing function.

According to an example of the present invention, there is provided a robot including the cutting device, wherein the first contact member is a first gripping member and the second contact member is a second gripping member, the contact mechanism is provided with a gripping mechanism having a gripping rotation mechanism for rotating the first gripping member toward the second gripping member, the cutting mechanism is provided with a cutting member attached to the first gripping member and a cutting rotation mechanism for rotating the cutting member in the same direction as the rotation of the first gripping member, the second gripping member is provided with a support shaft that rotatably supports the first gripping member and the cutting member, the gripping rotation mechanism is composed of a gripping movement mechanism that moves a portion of the first gripping member pivotally supported by the support shaft at a predetermined distance from the support shaft, wherein the cutting rotation mechanism is composed of a cutting movement mechanism that moves a portion of the cutting member pivotally supported by the support shaft at a predetermined distance from the support shaft, the gripping movement mechanism and the cutting movement mechanism are composed of an elongated long member to be moved along a long longitudinal direction, a gripping side driving unit for driving the gripping movement mechanism and a cutting side driving unit driving the cutting movement mechanism are provided, and wherein in a state where the first gripping member is rotated by the gripping movement mechanism driven by the gripping side driving unit and the target site is gripped by the gripping mechanism, the cutting member is rotated by the cutting movement mechanism driven by the cutting side driving unit, and the target site is cut by contacting with the second gripping member.

According to an example of the present invention, there is provided a cutting device wherein a contact mechanism is provided with a gripping mechanism having a gripping rotation mechanism for rotating a first gripping member toward a second gripping member, a cutting mechanism is composed of a cutting mechanism attached to the first gripping member, and a cutting rotation mechanism for rotating the cutting member in the same direction as the rotation of the first gripping member, the second gripping member is provided with a support shaft that rotatably supports the first gripping member and the cutting member, the gripping rotation mechanism is composed of a gripping movement mechanism provided with a pair of elongated members whose tips are fixed and move at predetermined a pair of positions on the outer periphery of the support shaft of the first gripping member, and wherein the cutting rotation mechanism is composed of a pair of elongated members whose tips are fixed and moved at predetermined pairs of positions on the outer periphery of the support shaft of the cutting member, and moves the pair of elongated members to rotate the cutting member. The elongate member may be made of a flexible long member such as a flexible wire.

A cutting device, robot, or portable surgical device of the present invention may employ a cutting device including a gripping mechanism having a first gripping member and a second gripping member assembled so as to be openable and closable, and a gripping member rotating mechanism for rotating the first gripping member toward the second gripping member, a cutting mechanism having a cutting member attached to the first gripping member and a cutting member rotating mechanism for rotating the cutting member in the same direction as the rotation of the first gripping member, a support shaft disposed at the second gripping member that rotatably supports the first gripping member and the cutting member, wherein the gripping member rotating mechanism is composed of a gripping member moving mechanism for moving the first gripping member pivotally supported by the support shaft at a predetermined distance from the support shaft, the cutting member rotation mechanism is composed of a cutting member moving mechanism that moves the cutting member pivotally supported by the support shaft at a predetermined distance from the support shaft, the gripping member moving mechanism and the cutting member moving mechanism are composed of a long member and are moved along a long longitudinal direction, wherein in a state where the first gripping member is rotated by the movement of the gripping member moving mechanism in the longitudinal direction and the target site is gripped by the gripping mechanism, the cutting member is moved by the movement of the cutting member moving mechanism in the longitudinal direction to cut the target site by rotating and joining with the second gripping member.

The medical system of the present invention may include a driving mechanism that independently drives the above-mentioned cutting device, the gripping movement mechanism and the cutting movement mechanism, and a medical robot connected so as to apply a drive signal to the driving mechanism.

BRIEF DESCRIPTION OF THE DRAWINGS

FIG. 1 at (a) is a front view of the forceps, FIG. 1 at (b) is a partial plane view of the cutting mechanism in the forceps, and FIG. 1 at (c) is a partial front view of the cutting mechanism of FIG. 1 at (b);

FIG. 3 at (a) is a side sectional view taken along the line A-A in FIG. 2, FIG. 3 at (b) is a partial vertical sectional view of the forceps, and FIG. 3 at (c) is a sectional view taken along the line B-B in FIG. 3 at (b) with an enlarged view of the electrode part;

FIG. 4 at (a) is a front view of the gripping state in which the gripping mechanism of the forceps is closed, and FIG. 4 at (b) is a rear view of the forceps in the same state;

FIG. 5 at (a) is a front view of the cutting mechanism of the forceps with the cutter closed, and FIG. 5 at (b) is a rear view of the forceps in the same state;

FIG. 6 at (a) is a side sectional view taken along the line A-A in FIG. 2 before being gripped by the gripping mechanism, and FIG. 6 at (b) is a state in which the target site is gripped and crashed by the gripping mechanism. A side sectional view taken along the line C-C, FIG. 6 at (c) is a side sectional view taken along the line D-D in FIG. 5 at (b) in a state where the target site is cut with a cutter, and FIG. 6 at (d) is a schematic side view on the right in a state of being gripped by a gripping mechanism of a cutting mechanism in another aspect.

FIG. 8 at (a) is a rear view of the forceps, and FIG. 8 at (b) is a side view of the forceps on the cutting mechanism;

FIG. 9 is a rear view of the forceps of FIG. 8. FIG. 8 at (b) is a partial cross-sectional view taken along the line E-E;

FIG. 10 at (a) is a front view of the forceps in the gripped state, FIG. 10 at (b) is a rear view of the forceps in the same state, FIG. 10 at (c) is a side view of the forceps in the same state on the cutting mechanism side, and FIG. 10 at (d).) Is a partial cross-sectional view taken along the line FF in FIG. 10 at (c);

FIG. 11 at (a) is a front view of the forceps in the cut state, FIG. 11 at (b) is a rear view of the forceps in the same state, FIG. 11 at (c) is a side view of the forceps in the same state on the cutting mechanism side, and FIG. 11 at (d) is a partial cross-sectional view taken along the line G-G in FIG. 11 at (c);

FIG. 12 is a front view of a forceps of still another embodiment of the present invention;

FIG. 13 is a rear view of the forceps of FIG. 12;

FIG. 14 at (a) is a front view of the forceps in the gripped state, and FIG. 14 at (b) is a rear view of the forceps in the same state;

FIG. 15 at (a) is a front view of the forceps in the cut state, and FIG. 15 at (b) is a rear view of the forceps in the same state;

FIG. 16 is a schematic front view of an end effector of still another embodiment of the present invention;

FIG. 17 at (a) is a side sectional view taken along the line H-H in FIG. 16, FIG. 17 at (b) is a partial vertical sectional view of the end effector, and FIG. 17 at (c) is an enlarged plane view of the end effector taken along the line I-I in FIG. 16;

FIG. 18 at (a) is a schematic front view of the end effector in the normal state, and FIG. 18 at (b) is a schematic front view of the end effector in the disconnected state;

FIG. 20 is a schematic cross-sectional view of an end effector showing an outline of an electrode of a modified connection example of a coaxial electrode and a coaxial cable. 20 at (a) is a side sectional view of a reverse connection with FIG. 19 at (a), and FIG. 20 at (b) is a partial vertical sectional view of the reverse connection with the connection in FIG. 17 at (b);

FIG. 21 is a schematic explanatory view of an end effector of a modification of the end effector of FIG. 17. FIG. 21 at (a) is a side sectional view taken along the line H-H in FIG. 16, FIG. 21 at (b) is a partial vertical sectional view of the end effector, and FIG. 21 at (c) is an enlarged plane view taken along the line I-I in FIG. 16;

FIG. 22 at (a) is a rear view of the forceps of FIG. 1 having a coaxial electrode, FIG. 22 at (b) is a front view of the forceps of FIG. 7 having a coaxial electrode, and FIG. 22 at (c) is a front view of forceps of FIG. 12 having a coaxial electrode;

FIG. 25 is a front view of an open forceps according to an embodiment of the present invention;

FIG. 26 is an explanatory view of forceps in an open state according to the first embodiment. FIG. 26 at (a) is a rear view of the forceps, FIG. 26 at (b) is a plane view of the forceps, and FIG. 2 at (c) is a bottom view of the forceps of FIG. 26 at (b);

FIG. 27 at (a) is a side sectional view taken along the line A-A in FIG. 25 at (a), FIG. 27 at (b) is a partial vertical sectional view of the forceps, and FIG. 27 at (c) is an enlarged view of the electrode part taken along the line B-B in FIG. 27 at (b).

FIG. 28 at (a) is a front view of a gripping mechanism of the forceps in a gripping and crashing state in which the gripping mechanism of the forceps is closed, and FIG. 28 at (b) is a rear view of the forceps in the same state;

FIG. 29 at (a) is a front view of the cutting mechanism of the forceps with the cutter closed, and FIG. 29 at (b) is a rear view of the forceps in the same state;

FIG. 30 at (a) is a side sectional view taken along the line A-A in FIG. 25 before gripping with the gripping mechanism, and FIG. 30 at (b) shows a side sectional view taken along the line C-C in FIG. 28 at (b) in a state where the target site is gripped and crashed by the gripping mechanism. FIG. 30 at (c) is a side sectional view taken along the line D-D in FIG. 29 at (b) in a state where the target site is cut with a cutter, and FIG. 30 at (d) is right schematic side view of the state of being gripped by the gripping mechanism of the cutting mechanism of another embodiment.

FIG. 33 at (a) is a front view of the gripping state in which the gripping mechanism of the forceps is closed, and FIG. 33 at (b) is a rear view of the forceps in the same state;

FIG. 34 at (a) is a front view of the cutting mechanism of the forceps with the cutter closed, and FIG. 34 at (b) is a rear view of the forceps in the same state;

FIG. 36 is a rear view of the open state forceps of another embodiment;

FIG. 38 at (a) is a rear view of the forceps. FIG. 38 at (b) is a partial vertical sectional view of the forceps, and FIG. 38 at (c) is a side sectional view taken along the line E-E in FIG. 38 at (a);

FIG. 39 at (a) is forceps rear view of the forceps, FIG. 39 at (b) is a partial longitudinal sectional view of the forceps;

FIG. 41 at (a) is a side sectional view of the F-F arrow in FIG. 40, FIG. 41 at (b) is a partial vertical sectional view of the end effector, and FIG. 41 at (c) is an enlarged plane view of the G-G arrow in FIG. 40. FIG. 41 at (c) is an enlarged view in FIG. 41 at (b);

FIG. 42 at (a) is a schematic front view of the end effector in the normal state, FIG. 42 at (b) is a schematic front view of the end effector in a gripping and crashing state, and FIG. 42 at (c) is a schematic front view of the end effector in the cut state;

FIG. 43 is a schematic explanatory view of an end effector of a modification of the end effector of FIG. 41. FIG. 43 at (a) is a side sectional view of the F-F arrow in FIG. 40, FIG. 43 at (b) is a partial vertical sectional view of the end effector, and FIG. 43 at (c) is an enlarged plane view of the G-G arrow in FIG. 40;

FIG. 45 is a schematic explanatory view of a medical device in another embodiment;

FIG. 48 is an explanatory diagram relating to a remote surgery system; and

DETAILED DESCRIPTION

Figure 1:
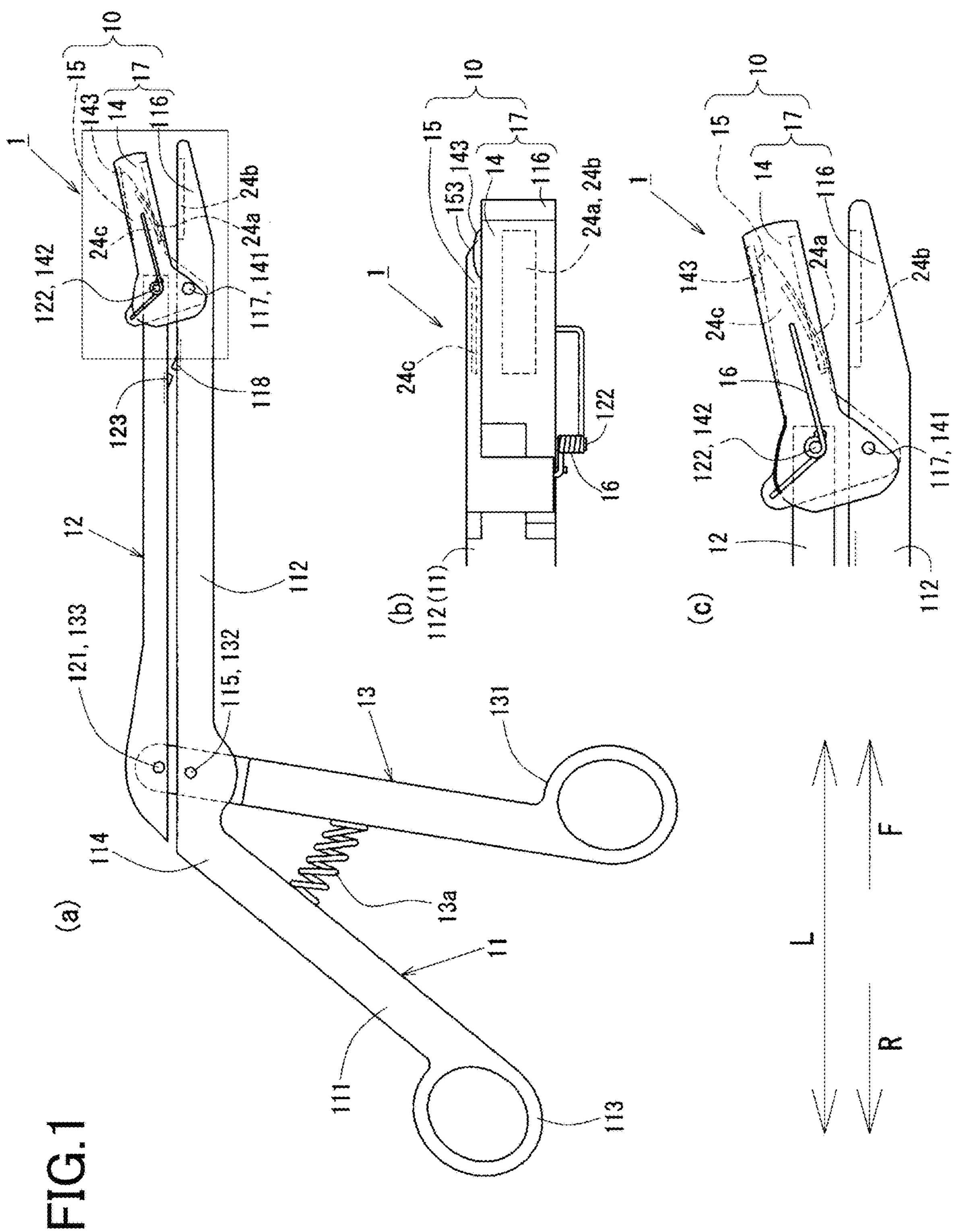
FIG. 1 is an explanatory view of an open forceps according to an embodiment of the present invention.

Embodiments of the present invention will be described below with reference to the accompanying drawings. In the following description, the same parts and components are designated by the same reference numerals. The present embodiment includes, for example, the following disclosures.

[Structure 1]

A cutting device, forceps, or medical device (1,1X) including a first contact member (14, 14*a*, 14*b*) and a second contact member (116, 116*a*, 119*b*) assembled so as to be openable and closable, a contact mechanism (17,17*a*) that rotates the first contact member (14, 14*a*, 14*b*) toward the second contact member (116, 116*a*, 119*b*) to bring the first contact member (14, 14*a*, 14*b*) and the second contact member (116, 116*a*, 119*b*) into contact with a target site (B), and a cutting mechanism (10, 10X, 19) for cutting the target site in a state where the first contact member (14, 14*a*, 14*b*) and the second contact member (116, 116*a*, 119*b*) are in contact with the target site (B) by the contact mechanism (17,17*a*). According to this configuration, it is possible to grip an external member such as a plate material, a pipe, a rod, or a tissue and cut the gripped member. In addition, the gripped member can be processed by heating, irradiating with energy such as microwaves, or the like in a gripped/crashed state, and then cut by the cutting member. It can be used in multiple fields as a cutting device.

[Structure 2]

The cutting device, forceps, or medical device (1,1X, 1Y, 10*a*, 220) according to Structure 1, further including a gripping mechanism (17, 17*a*) in which the first contact member (14,14*a*) and the second contact member (116,116*a*) are a first grip member (14,14*a*) and a second grip member (116,116*a*), and the contact mechanism (17,17*a*) rotates the first grip member (14,14*a*) toward the second grip member (116,116*a*) to grip the target site (B) between the first gripping member (14,14*a*) and the second gripping member (116,116*a*), a cutting member (15,15*a*,15Y) attached to the first gripping member (1; $_o$ wherein the cutting mechanism (10, 10X, 19) moves (rotate or slide) the cutting member (15,15*a*,15Y) along the first gripping member in a state where the target site (B) is gripped by the first gripping member (14,14*a*) and the second gripping member (116, 116*a*) by the gripping mechanism (17,17*a*), and the target site (B) is cut by joining the cutting member (15,15*a*,15Y) with the second gripping member (116,116*a*), and a gripping/cutting method using the same above device.

[Structure 3]

The cutting device, forceps, or medical device (1,1X, 1Y, 10*a*, 220) according to Structure 1 or 2, including electrodes (20,24*a*,24*b*,24*c*) which are disposed in at least one of a gripping portion that grips the target site (B) in the first gripping member (14,14*a*) and a vicinity of the cutting blade in the cutting member (15,15*a*,15Y), and a gripping portion that grips the target site (B) in the second gripping member (116,116*a*) for irradiating electromagnetic waves. A method of gripping, coagulating, and cutting a living tissue with forceps, a medical device (1,1X, 1Y, 10*a*, 10*b*, 220), and the same device. A method of gripping, crashing, coagulating, or cutting the target site by the above device, which may be a method of gripping, crashing, and then coagulating the living or biological tissue.

[Structure 4]

The electrode (20) is a coaxial electrode (20) provided with a center electrode (21) and an outer electrode (23) surrounding the center electrode (21) via an insulator, and irradiates the electromagnetic wave. The coaxial cable (40) connecting the irradiation device (30) and the electrode (20) is branched in parallel to a plurality of coaxial cables (40), and the coaxial cable (40) is connected to the central conductor (41) and the outer conductor (43). The cutting device, forceps, or medical device (1,1X, 1Y, 10*a*, 10*b*, 220) and gripping device according to the structure 3 in which each of the electrodes (20) is electrically connected to the same pole or the opposite polarity, and methods of gripping, crashing, coagulating, and cutting.

[Structure 5]

The forceps (1,1X, 1Y, 10*a*) provided with the cutting device (1,1X, 1Y) according to any one of structures 2 to 4 in which the first gripping member (14,14*a*) and the second gripping member (116,116*a*) are a first jaw member (14,14*a*) and a second jaw member (116,116*a*) respectively, including a driving mechanism for gripping and coagulating a target site (B) by rotating the first jaw member (14,14*a*) toward the second jaw member (116), and one operation member (13) for operating the driving mechanism and the cutting mechanism, wherein by a series of operations of the operation member (13), and a biological tissue (B) as the target site (B) is gripped by the first jaw member (14,14*a*) and the second jaw member (116,116*a*), and then the forceps (1,1X, 1Y, 10*a*) cut by the cutting mechanism (10,10X), and a method of gripping, crashing, coagulating, and cutting by using the forceps or its similar equipment.

Driving Mechanism Driving Mechanism

In the case of this configuration, the gripping mechanism (17, 17*a*) and the cutting mechanism (10, 10X) are operated together by the operation of the operation member (13) until the grip is performed, and further operation of the operation member (13) is performed. A differential mechanism (142, 16X, 16Y) in which the cutting mechanism (10, 10X) is differential from the gripping mechanism (17, 17*a*) in a gripping state in which the target site (B) is gripped and crashed is provided. There may be provided, a notification unit (118, 123) for notifying the user of the operation of the differential mechanism (142, 16X, 16Y) by a series of operations of the operation member (13).

[Structure 6]

The cutting device, forceps, or medical device (10*b*, 220) according to the Structure 1 having the following components; the first contact member and the second contact member are provided with cutting blades (153*a*, 153*b*) for cutting the target site (B) at the contact portion to cut the target site (B); the cutting member (14*b*) and the second cutting member (119*b*), and the contact mechanism abuts on the target site (B) by the first cutting member (14*b*) and the second cutting member (119*b*); and the cutting mechanism (19) for cutting the device, electrodes (20) for irradiating electromagnetic waves along the cutting blades (153*a*, 153*b*) in the first cutting member (14*b*) and the second cutting member (119*b*).

[Structure 7]

The cutting device, forceps, or medical device (10*b*, 220) according to Structure 6, which is electrically connected to the same pole or the opposite polarity. Further, including the followings: the electrode (20) is a coaxial electrode (20) provided with a center electrode (21) and an outer electrode (23) surrounding the center electrode (21) via an insulator, and irradiates the electromagnetic wave; the coaxial cable (40) connecting the irradiation device (30) and the electrode (20) is branched in parallel to a plurality of coaxial cables (40), and the coaxial electrode (20) is attached to the central conductor and the outer conductor of the coaxial cable (40); and the first cutting member (14*b*) and the second cutting member (119*b*) have functions of coagulating, cutting, and separating living tissue.

[Structure 8]

The forceps (1,1X, 1Y, 10*a*, 10*b*) includes a plurality of the above medical device with each of said forceps (1,1X, 1Y, 10*a*, 10*b*) the electrodes (20) provided in the microwave In addition to being an irradiation electrode (20), a microwave irradiation unit is provided on each of the forceps (1,1X, 1Y), and a microwave applied to each electrode (20) from the coaxial cable (40). Surgical system with the same cycle.

[Structure 9]

A robot including the following components: an input/output unit (210*a*) connected to the disconnectors (10*a*, 10*b*) by wire and/or wirelessly, an input unit (210*a*) that receives an operation signal in real time, and a predetermined operation program based on the operation signal; the first contact member (14, 14*a*, 14*b*) of the cutting device (10*a*, 10*b*) and the second contact member (116, 116*a*, 119*b*); and a robot (210) equipped with an output unit (210*a*) that generates a drive signal that contacts and crashes or disconnects from the target site (B) and/or an irradiation signal that irradiates the electromagnetic waves from the electrodes (20, 24*a*, 24*b*, 24*c*).

[Structure 10]

A control method of generating a command by operating the master control unit (202), moving the arm assembly (212) of the robot (210) to a treatment position by the above command, and an arm assembly (212) of the robot (210). A robot having a step of moving the tool (217) attached to the tool (217) to a treatment position and a step of controlling the movement of the cutting device (10*a*, 10*b*) attached to the tip of the tool (217) and the irradiation of electromagnetic waves.

[Structure 11]

Surgical system (210) with a robot (210) described in Structure 9 which is a patient-side cart (200), including a plurality of surgeon consoles (201) serving as stations for a plurality of operators, a master control unit (202) operated by a plurality of operators.

[Structure 12]

A cutting device including a first gripping member (upper jaw part: 14) and a second gripping member (lower jaw part: 116) assembled so as to be openable and closable, a gripping mechanism having a gripping rotation mechanism (16*a*) for rotating the first gripping member (14) toward the second gripping member (116), a cutting mechanism having a cutting member (15) attached to the first gripping member (14) and a cutting rotation mechanism (16*b*) for rotating the cutting member in the same direction as the rotation of the first gripping member, in which the second gripping member (116) is provided with a support shaft (117*a*) that rotatably supports the first gripping member (14) and the cutting member (15), the gripping rotation mechanism (16*a*) is composed of a pair of elongated members (161 (16*a*) and 162 (16*a*)) and rotates the first grip member (14) by moving the pair of elongated members (161 (16*a*), 162 (16*a*)) the cutting rotation mechanism (16*b*) is a pair of elongated members (161 (16*b*), 162 (16*b*)) whose tips are fixed and move to a predetermined pair of points (152*a*, 152*b*) on the outer periphery of the support shaft (117*a*) of the cutting member (15) and the cutting movement mechanism that rotates the cutting member (15) by moving the pair of elongated members (161 (16*b*), 162 (16*b*)). The elongated member may be composed of a flexible elongated member such as a flexible wire.

[Structure 13]

A cutting device including: a gripping mechanism having a first gripping member and a second gripping member assembled so as to be openable and closable, and a gripping member rotating mechanism for rotating the first gripping member toward the second gripping member, a cutting mechanism having a cutting member attached to the first gripping member and a cutting member rotating mechanism for rotating the cutting member in the same direction as the rotation of the first gripping member, a support shaft disposed at the second gripping member that rotatably supports the first gripping member and the cutting member, wherein the gripping member rotating mechanism is composed of a gripping member moving mechanism for moving the first gripping member pivotally supported by the support shaft at a predetermined distance from the support shaft, wherein the cutting member rotation mechanism is composed of a cutting member moving mechanism that moves the cutting member pivotally supported by the support shaft at a predetermined distance from the support shaft, wherein the gripping member moving mechanism and the cutting member moving mechanism are composed of a long member and are moved along a long longitudinal direction, and wherein in a state where the first gripping member is rotated by the movement of the gripping member moving mechanism in the longitudinal direction and the target site is gripped by the gripping mechanism, the cutting member is moved by the movement of the cutting member moving mechanism in the longitudinal direction to cut the target site by rotating and joining with the second gripping member.

The elongated member may be a flexible elongated member.

[Structure 14]

The cutting device according to structure 1, wherein the first contact member is a first gripping member and the second contact member is a second gripping member, wherein the contact mechanism is provided with a gripping mechanism having a gripping rotation mechanism for rotating the first gripping member toward the second gripping member, wherein the cutting mechanism is composed of a cutting mechanism attached to the first gripping member, and a cutting rotation mechanism for rotating the cutting member in the same direction as the rotation of the first gripping member, wherein the second gripping member is provided with a support shaft that rotatably supports the first gripping member and the cutting member, wherein the gripping rotation mechanism is composed of a gripping movement mechanism provided with a pair of elongated members whose tips are fixed and move at predetermined a pair of positions on the outer periphery of the support shaft of the first gripping member, and wherein the cutting rotation mechanism is composed of a pair of elongated members whose tips are fixed and moved at predetermined pairs of positions on the outer periphery of the support shaft of the cutting member, and moves the pair of elongated members to rotate the cutting member. The elongated member may be configured by a flexible elongated member such as a flexible wire.

[Structure 15]

A robot including the cutting device wherein the first contact member is a first gripping member and the second contact member is a second gripping member, the contact mechanism is provided with a gripping mechanism having a gripping rotation mechanism for rotating the first gripping member toward the second gripping member, the cutting mechanism is provided with a cutting member attached to the first gripping member and a cutting rotation mechanism for rotating the cutting member in the same direction as the rotation of the first gripping member, the second gripping member is provided with a support shaft that rotatably supports the first gripping member and the cutting member, driving unit drives the gripping rotation mechanism and the cutting rotation mechanism independently to coagulate and cut the target site while gripping the target site by applying a drive signal to the driving unit. The driving unit may selectively drives at least one of a drilling function, a gripping function, a crashing function, a coagulation function, a cutting function, and an opening (widening) function by driving the first gripping member, the second gripping member, and the cutting member in combination.

[Structure 16]

A cutting device wherein the gripping movement mechanism composed of the flexible elongated member is provided with a first gripping movement mechanism connected to one of two predetermined positions separated from the support shaft by a predetermined distance in the first gripping member for movement in a pulling direction in the longitudinal direction, and a second gripping movement mechanism which is connected to the other predetermined position for movement in a pulling direction in the longitudinal direction, and wherein the cutting movement mechanism composed of the flexible elongated member is provided with a first gripping movement mechanism connected to one of two predetermined positions separated from the support shaft by a predetermined distance in the cutting member for movement in a pulling direction in the longitudinal direction, and a second gripping movement mechanism which is connected to the other predetermined position for movement in a pulling direction in the longitudinal direction,

[Structure 17]

A gripping movement mechanism and a cutting movement mechanism composed of the flexible elongated member move a predetermined portion in a pulling direction in the longitudinal direction, and the predetermined portion moves in a pushing direction in the longitudinal direction. A gripping urging portion that urges the first gripping member and a cutting urging portion that urges the first cutting member in a direction in which the predetermined portion moves in the pushing direction may be provided. The gripping movement mechanism and the cutting movement mechanism may move predetermined locations in the pushing direction and the pulling direction in the longitudinal direction. According to this Structure, by moving the first gripping member by the gripping movement mechanism, the first gripping member rotates with respect to the second gripping member to grip the target site, and the cutting member is moved by the cutting movement mechanism. By doing so, the cutting member can rotate with respect to the second gripping member to cut the target site.

[Structure 18]

A notification unit may be provided to notify the outside of at least one of the rotation of the first gripping member and the rotation of the cutting member with respect to the second gripping member, and the notification amount of the notification unit is adjusted. Notification amount adjusting mechanism may be provided. The notification unit may be, for example, a notification by a sound such as a click sound, a notification by a sensation such as a click feeling, or a notification as an electric or electric signal such as on/off of energization. Therefore, the notification amount adjusting mechanism is a mechanism for adjusting the magnitude of the sound in the click sound, the magnitude of the sensation in the click feeling, the magnitude of the energization amount, and the like. According to this configuration, it is possible to notify the outside of at least one of the rotation of the first gripping member with respect to the second gripping member and the rotation of the cutting member.

According to the above configurations, there are provided a cutting device, forceps, end effectors, medical tools, medical systems, robots, and medical operation robots, which can grip the target site and cut the target site without changing or replacing the device. A gripping/cutting method and a portable surgical device can be provided.

The following embodiments will be described as being used for a medical device as an example of the cutting device of the present invention, and examples of forceps and the like will be described below, but the present invention provides a cutting device and a tool not limited to the medical device.

Returning to FIG. 1, there is shown an explanatory diagram of forceps 1 in an open state according to an embodiment of the present invention. FIG. 1 at (a) shows a front view of the forceps 1, FIG. 1 at (b) shows a partial plane view of the cutting mechanism 10 in the forceps 1, and FIG. 1 at (c) shows a partial front view of the cutting mechanism 10 of FIG. 1 at (b).

Figure 2:
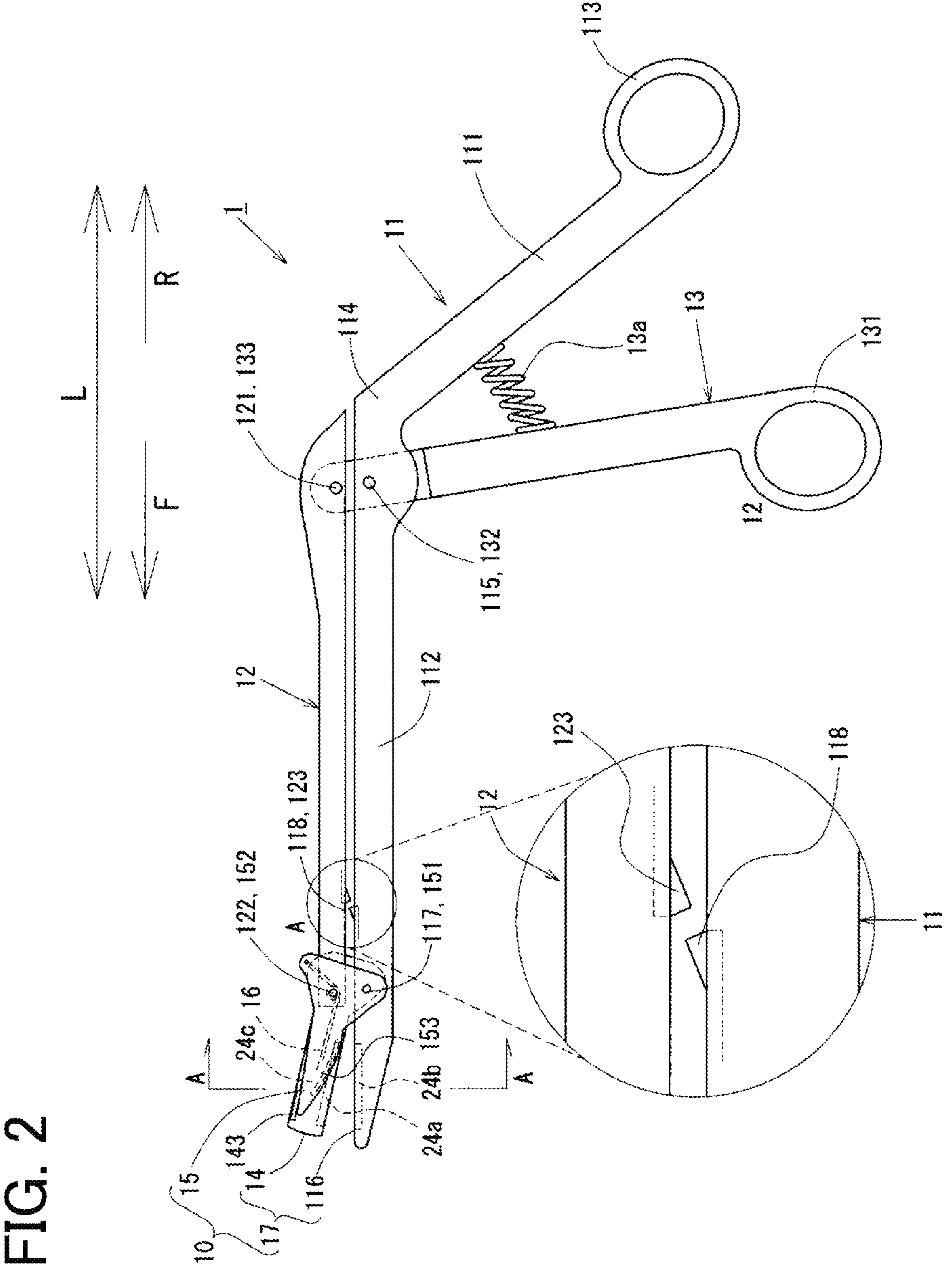
FIG. 2 is a rear view of the forceps of FIG. 1.

FIG. 2 shows a rear view of the forceps 1 of FIG. 1

Figure 3:
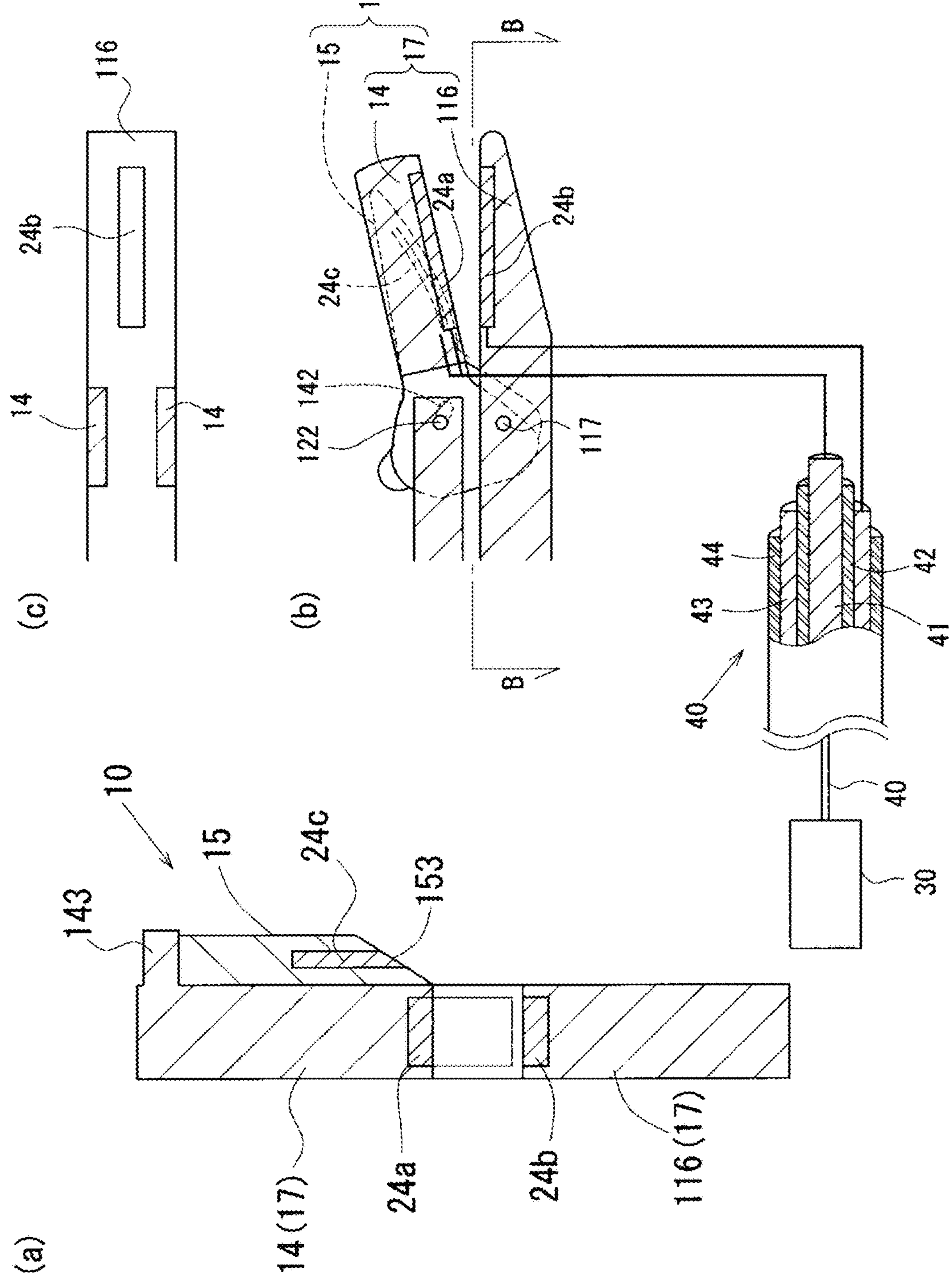
FIG. 3 is a schematic explanatory view of the forceps of FIG. 1.

FIG. 3 is a schematic explanatory view of the forceps of FIG. 1. FIG. 3 at (a) is a side sectional view taken along the line A-A in FIG. 2, FIG. 3 at (b) is a partial vertical sectional view of the forceps, and FIG. 3 at (c) is a sectional view taken along the line B-B in FIG. 3 at (b) with an enlarged view of the electrode part.

Figure 4:
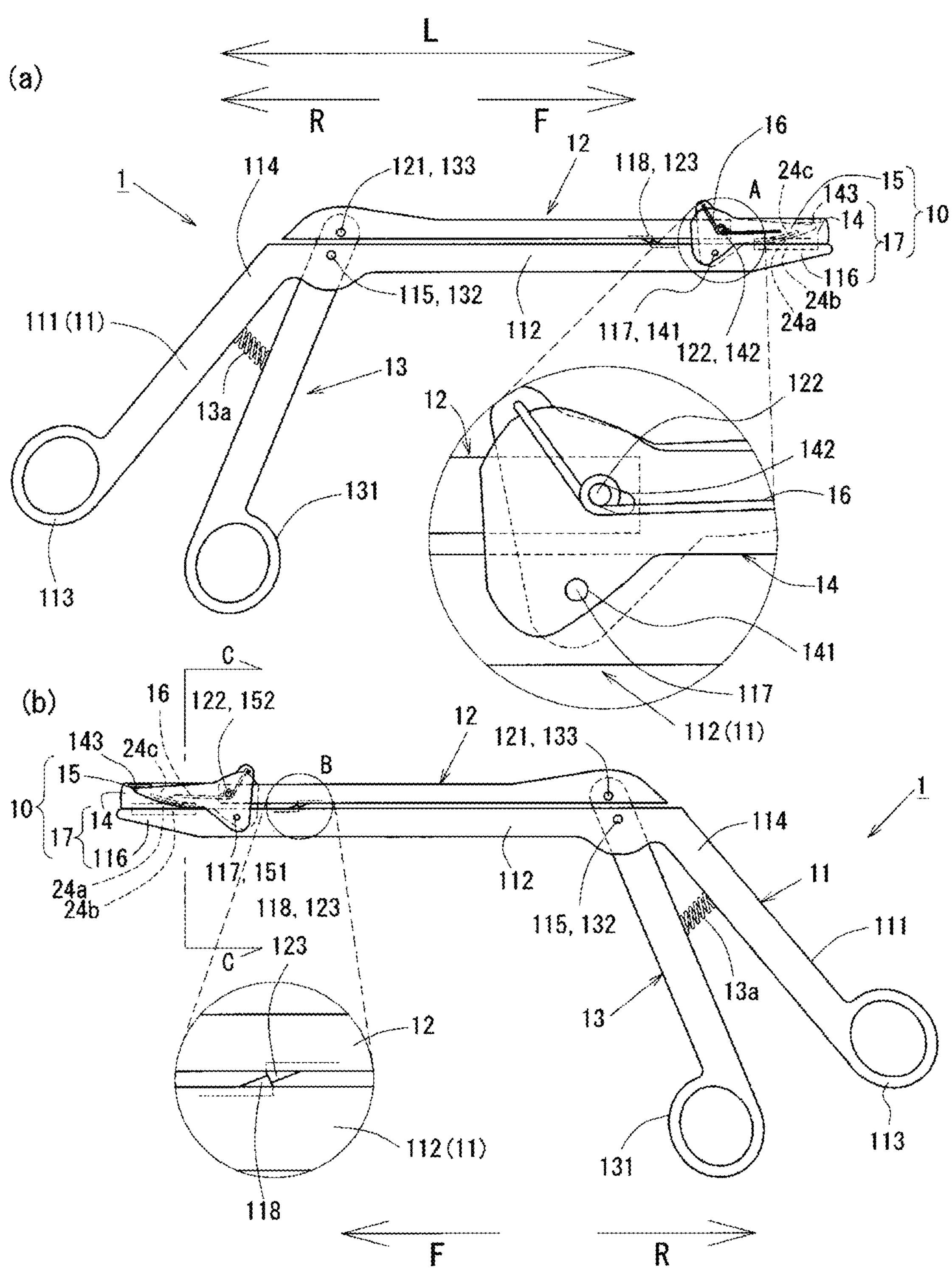
FIG. 4 is an explanatory view of a gripped state of the forceps of FIG. 1.

FIG. 4 is an explanatory view of a gripped state of the forceps of FIG. 1. FIG. 4 at (a) is a front view of the gripping state in which the gripping mechanism of the forceps is closed, and FIG. 4 at (b) is a rear view of the forceps in the same state.

Figure 5:
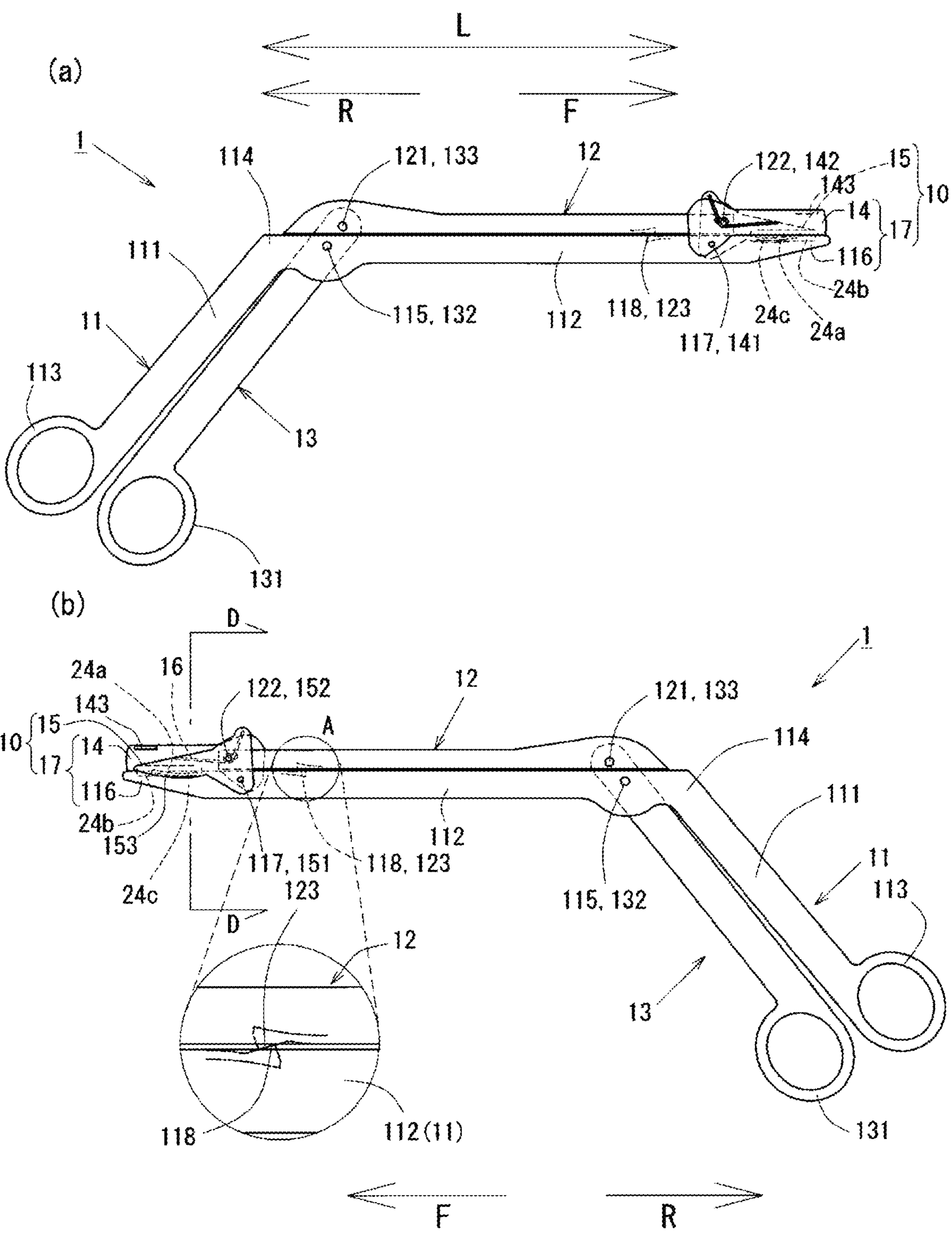
FIG. 5 is an explanatory view of a cut state of the forceps of FIG. 1.

FIG. 5 is an explanatory view of a cut state of the forceps of FIG. 1. FIG. 5 at (a) is a front view of the cutting mechanism of the forceps with the cutter closed, and FIG. 5 at (b) is a rear view of the forceps in the same state.

Figure 6:
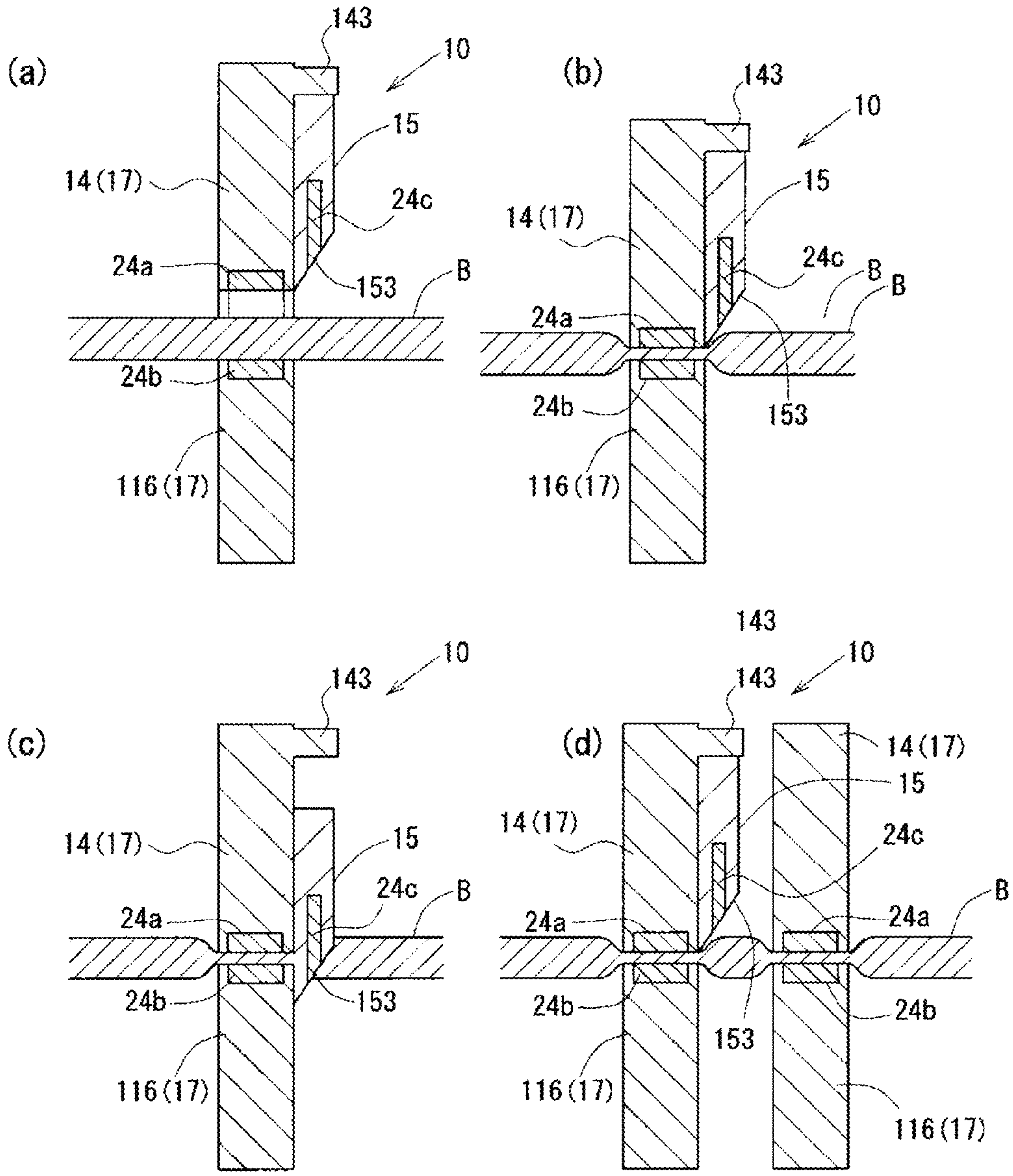
FIG. 6 is an explanatory view of a gripping state and a cutting state of the cutting mechanism in forceps.

FIG. 6 is an explanatory view of a gripping state and a cutting state of the cutting mechanism in forceps. FIG. 6 at (a) is a side sectional view taken along the line A-A in FIG. 2 before being gripped by the gripping mechanism, and FIG. 6 at (b) is a state in which the target site is gripped and pressed by the gripping mechanism. A side sectional view taken along the line C-C, FIG. 6 at (c) is a side sectional view taken along the line D-D in FIG. 5 at (b) in a state where the target site is cut with a cutter, cutter In FIG. 1 (FIGS. 1 to 6), the forceps 1 includes a main body frame 11, a slide frame 12, a trigger handle 13, an upper jaw portion 14, a cutter 15, and a spring 16.

The main body frame 11 is roughly composed of two sides that intersect in an obtuse angle, and one of the two sides is a fixed handle frame 111 that functions as an operation member together with the trigger handle 13, and the other is a reference frame 112. The main body frame 11 configured in this way is made of a metal such as stainless steel or a resin.

At the end of the fixed handle frame 111, a ring portion 113 for inserting a user's finger for operating the forceps 1 is provided. If necessary, the ring portion 113 may be provided with a cut portion.

Further, a portion where the fixed handle frame 111 and the reference frame 112 intersect at an obtuse angle is a corner portion 114, and a trigger handle 13 described later is pivotally supported at the base portion (near the above-mentioned corner portion 114) of the reference frame 112 by a support shaft 115.

Further, at the end of the tip side F of the reference frame 112, a lower jaw portion 116 constituting a gripping mechanism 17 for gripping a target site such as a blood vessel (B) to be treated is provided in cooperation with the trigger handle 13. The lower jaw portion 116 is configured to have a tapered shape toward the tip end side F in front view. The lower jaw portion 116 is also referred to as "mandibular".

Further, on the tip end side F of the reference frame 112, a tip support shaft 117 that pivotally supports the upper jaw portion 14 and the cutter 15 is provided.

Further, a click convex portion 118 (see FIG. 2) protruding toward the bottom surface of the slide frame 12 is provided on the upper surface of the intermediate portion of the reference frame 112 in the longitudinal direction L.

The click convex portion 118 has a triangular shape in front view protruding toward the bottom surface of the slide frame 12, but has a substantially right angle in front view in which the inclined surface of the base end side R has a steeper inclination angle than the inclined surface of the tip end side F. Further, the click convex portion 118, which has a triangular shape when viewed from the front and protrudes toward the bottom surface of the slide frame 12, is supported so as to bend downward with a predetermined force.

The slide frame 12 is provided so as to be slidable in the longitudinal direction L along the reference frame 112 in the main body frame 11, and is made of the same material as the main body frame 11 and is formed in a prismatic shape.

An upper support shaft 121 that pivotally supports the tip of the trigger handle 13 is provided on the base end side R (left side in FIG. 1) of the slide frame 12.

Further, on the tip end side (left side in FIG. 1) of the slide frame 12, a tip top support shaft 122 that pivotally supports the upper jaw portion 14 and the cutter 15 is provided.

Further, a click convex portion 123 (see FIG. 2) protruding toward the upper surface of the reference frame 112 is provided on the bottom surface of the intermediate portion of the slide frame 12 in the longitudinal direction L.

The click convex portion 123 has a triangular shape in front view protruding toward the upper surface of the reference frame 112, but the inclined surface of the tip side F facing the click convex portion 118 and the longitudinal direction L is from the inclined surface of the proximal end side R. It is formed in the shape of a substantially right-angled triangle in front view, where the inclination angle is steep. Further, the click convex portion 123, which has a triangular shape in front view and protrudes toward the upper surface of the reference frame 112, is supported so as to bend upward with a predetermined force.

The click convex portion 123 is not limited to a triangular shape, but may have another shape such as a polygonal shape or a semicircular shape that provides a function of notifying the user of a click sound or vibration.

The click convex portion 118 and the click convex portion 123 are arranged slightly apart from each other in the longitudinal direction L of the reference frame 112 and the slide frame 12 in the forceps 1 in the initial state (open state).

The trigger handle 13 is an operation member sliding the slide frame 12 along the reference frame 112, and includes a ring portion 131 at the lower end for inserting a user's finger.

Further, in the vicinity of the upper end of the trigger handle 13, a pivot portion 132 that is pivotally supported by the support shaft 115 of the main body frame 11 is provided, and is pivotally attached to the upper support shaft 121 of the slide frame 12 further above the pivot portion 132. It includes an upper axis 133 that is movably supported.

A compression coil spring **13*a* for automatically returning the slide frame 12 and the trigger handle 13 is provided between the fixed handle frame 111 and the trigger handle 13 (not shown in FIG. 5). The compression coil spring 13*a*** may be omitted depending on the specifications.

The upper jaw portion 14 is provided at the end portion of the tip side F of the slide frame 12, and constitutes the gripping mechanism 17 together with the lower jaw portion 116 of the main body frame 11. The upper jaw portion 14 is also referred to as "maxilla".

At the base end portion (left side in FIG. 1) of the upper jaw portion 14, a shaft-bearing portion 141 pivotally supported by the tip support shaft 117 of the main body frame 11 and a tip-top support shaft of the slide frame 12 above the shaft-mounted portion 141. A rotary bearing portion 142 pivotally supported by the 122 is provided. As shown in FIG. 1 at (c), which is an enlarged view of the portion surrounded by the square in FIG. 1 at (a), the rotary bearing portion 142 has a long hole shape (see FIG. 4) in which the support shaft 122 on the tip is loosely fitted.

A tip side on the back side of the upper jaw portion 14 is provided with a protrusion control unit 143 to restrict that the cutter 15 rotating along the back surface side surface of the upper jaw portion 14 projects upward from the upper surface of the upper jaw portion 14.

As shown in FIGS. 1 and 2, the cutter 15 is arranged on the back side of the upper jaw portion 14 and is pivotally supported by the tip support shaft 117 of the main body frame 11 and above the shafted portion 151. A rotation shaft portion 152 that is pivotally supported by a support shaft 122 on the tip of the slide frame 12 is provided. The cutter 15 configured in this way has a cutting blade 153 formed along the lower end portion. Further, the cutter 15 has a plate shape and is configured to rotate along the side surface of the upper jaw portion 14 with the shafted portion 151 as an axis.

A spring 16 is arranged along the front side of the upper jaw portion 14 and is configured to urge the upper jaw portion 14 and the cutter 15.

More specifically, the spring 16 is a torsion spring that fits outside the support shaft 122 on the tip, and one arm is fitted to the upper jaw portion 14 and the other arm is fitted to a part of the cutter 15. Therefore, when the upper jaw portion 14 and the cutter 15 are differentially rotated toward the side close to each other with the tip upper support shaft 122 as the center, the spring 16 is attached in the rotation direction in which the upper jaw portion 14 and the cutter 15 are separated from each other.

In the forceps 1 configured in this way, a gripping mechanism 17 that grips the target site includes the lower jaw portion 116 provided at the end of the tip end side F of the main body frame 11 and the upper jaw portion 14 whose base is pivotally supported by the tip support shaft 117 with respect to the main body frame 11.

Further, the cutter 15 that rotates and cuts the target site gripped by the gripping mechanism 17 along the side surface of the upper jaw portion 14 constitutes the cutting mechanism 10 together with the gripping mechanism 17.

The forceps 1 is provided with irradiation electrodes 24 (24*a*, 24*b*, 24*c*), and a coaxial cable 40 is connected to the microwave generator 30 (see FIG. 3) that oscillates microwaves and to the irradiation electrodes 24.

Specifically, the upper jaw portion 14 is provided with an irradiation electrode 24*a*, the lower jaw portion 116 is provided with an irradiation electrode 24*b*, and the inside of the cutter 15 is provided with an irradiation electrode 24*c*, and a coaxial cable 40 is connected to the irradiation electrode 24*c*. Although not shown, the irradiation electrodes 24 (24*a*, 24*b*, 24*c*) arranged on the upper jaw portion 14, the cutter 15 and the lower jaw portion 116 have an insulating layer arranged on the outside, and the upper jaw portion 14, the cutter insulated from 15 and the lower jaw 116.

As shown in the enlarged cross-sectional view of FIG. 3 at (b), the coaxial cable 40 is composed of a central conductor 41, an insulator 42, an outer conductor 43, and an insulating coating 44 with the central conductor 41 and the central conductor 41 interposed therebetween from the center to the outer diameter. They are arranged in this order.

The central conductor 41 is a linear conductor arranged at the center of the coaxial cable 40, and may be a single conductor having an appropriate diameter, or may be composed of a plurality of core wires.

Insulator 42 surrounds the outside of the central conductor 41 is made of resin for insulating the central conductors 41 and 43, and has a cylindrical shape having a predetermined thickness.

The outer conductor 43 is composed of braided wires provided along the outer peripheral surface of the insulator 42.

The insulating coating 44 is a coating having an insulating property and surrounds the outside of the outer conductor 43.

As described above, the coaxial cable 40 in which the central conductor 41, the insulator 42, the outer conductor 43, and the insulating coating 44 are arranged in this order from the center side has appropriate flexibility.

Figure 16:
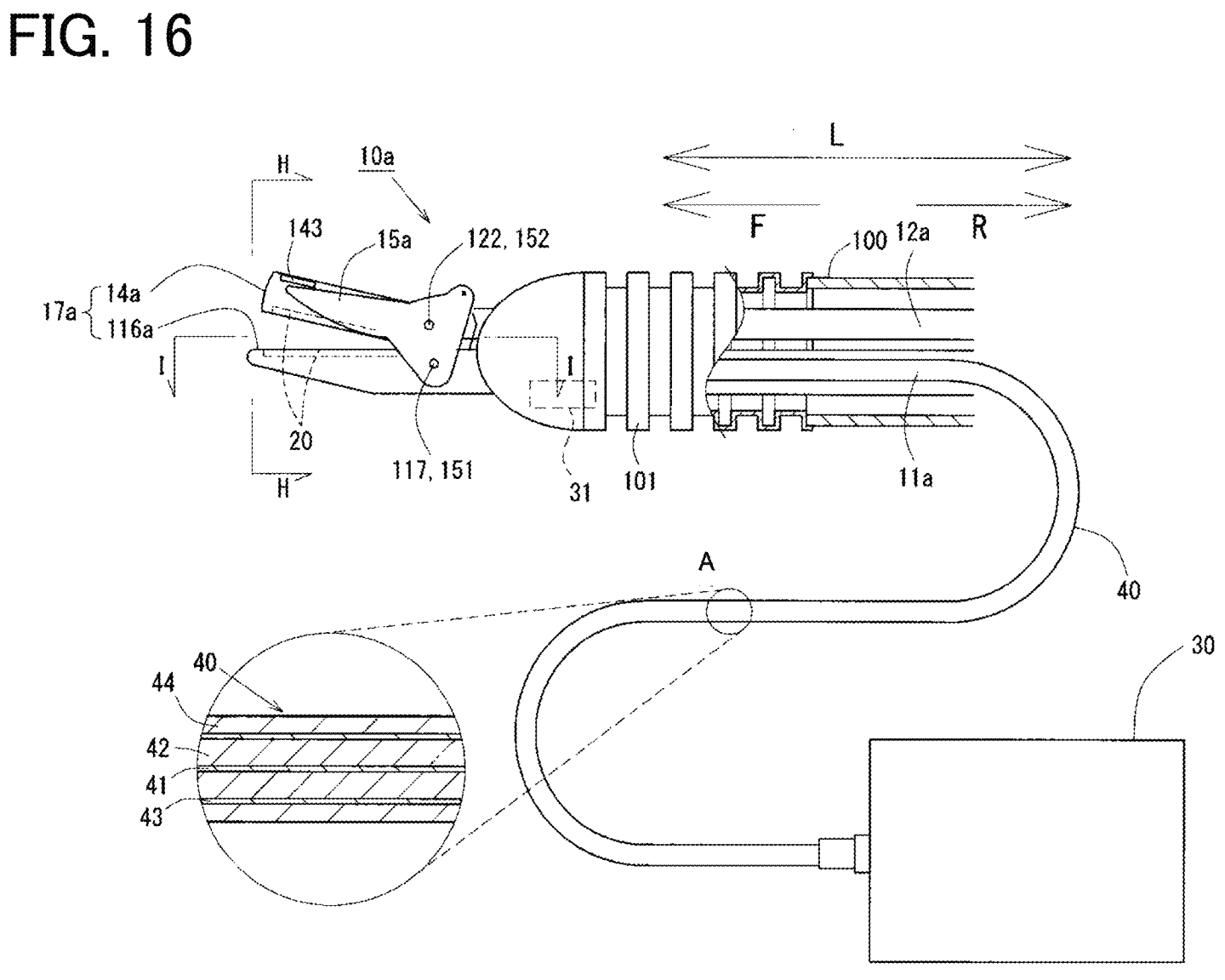
Figure 17:
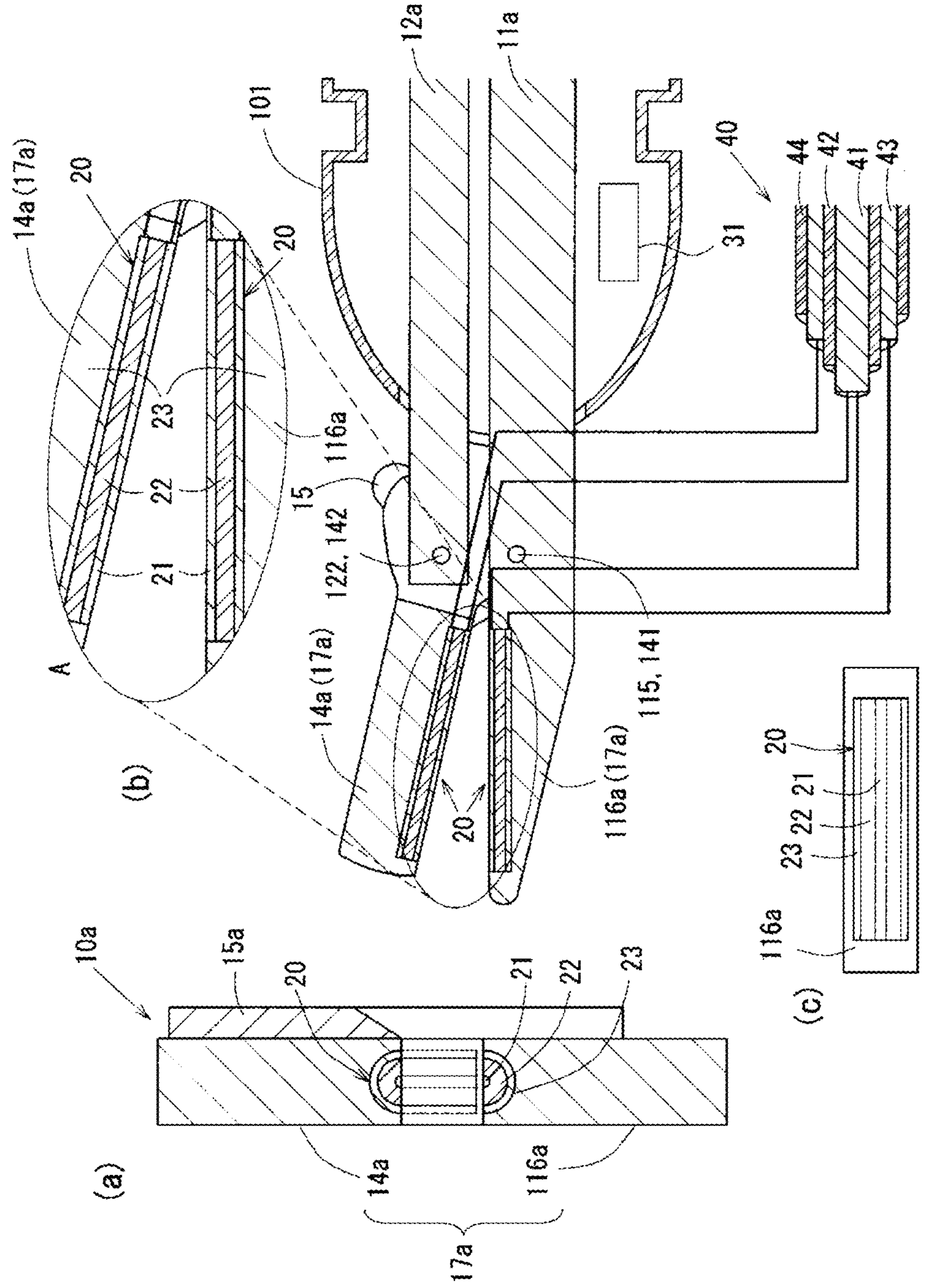
FIG. 17 is a schematic explanatory view of the end effector of FIG. 16.
Figure 20:
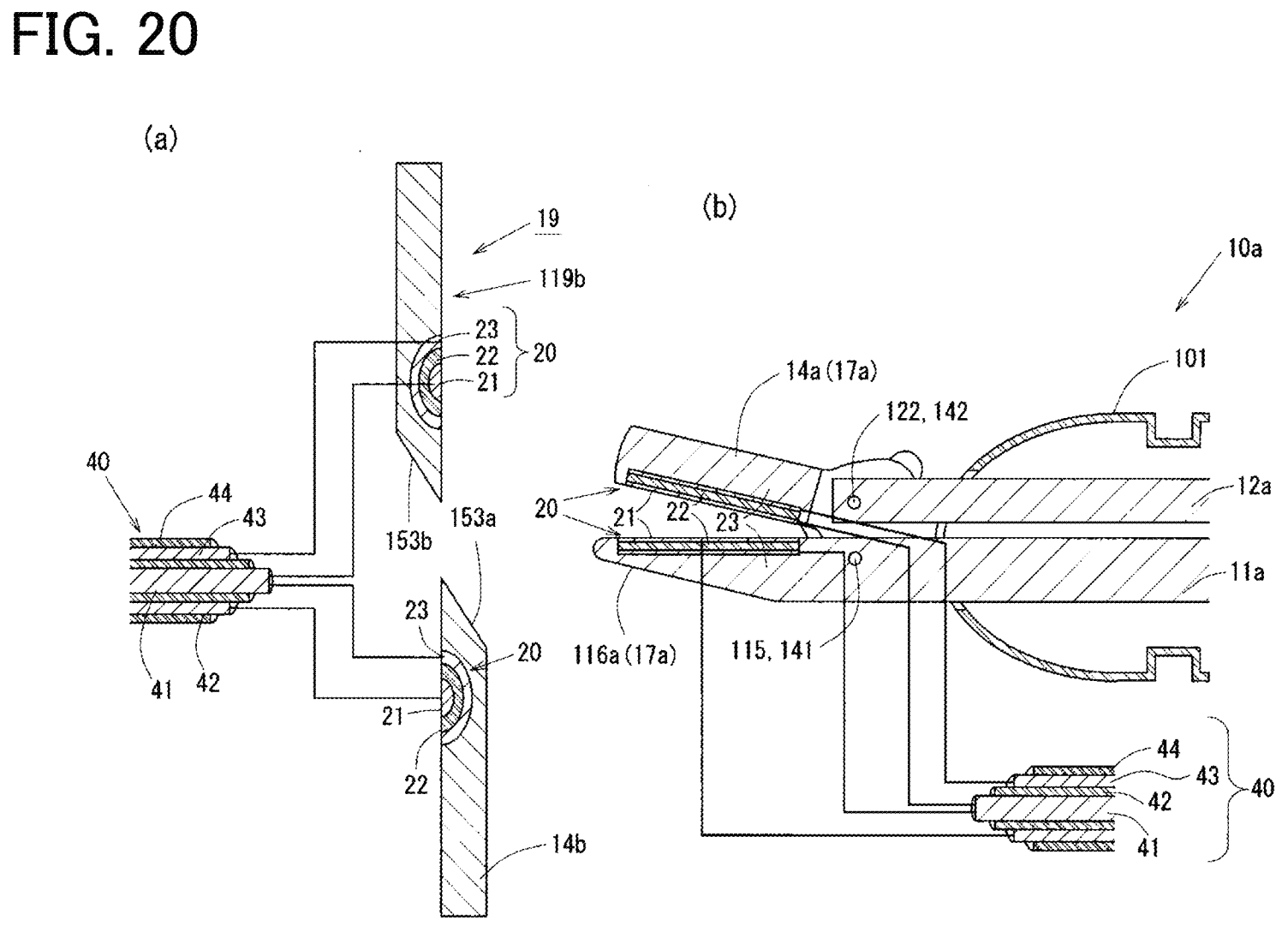

As shown in FIG. 3, the irradiation electrode 24*a* and the irradiation electrode 24*c* are connected to the central conductor 41 of the coaxial cable 40, the irradiation electrode 24*b* is connected to the outer conductor 43, and electromagnetic waves (microwaves) are irradiated from the irradiation electrodes 24*a* and 24*c* to the irradiation electrode 24*b*. Further, the electrode structure may be a coaxial structure as shown in FIGS. 16 and 17, and the polarity of the connection may be a different electrode connection structure as shown in FIG. 20.

One of the first electrode portion of the irradiation electrodes 24*a* and 24*c* of the upper jaw portion 14 and the cutter 15 and the second electrode portion of the irradiation electrode 24*b* provided on the lower jaw portion 116 is connected to the central conductor 41 of the coaxial cable 40. The other will be connected to the outer conductor 43. In this way, the forceps 1 provided with the irradiation electrodes 24*a* and 24*c* irradiate microwaves from one of the first electrode portion of the irradiation electrodes 24*a* and 24*c* and the second electrode portion of the irradiation electrode 24*b* toward the other. can do. As a result, the target site gripped by the gripping mechanism 17 composed of the lower jaw portion 116 and the upper jaw portion 14 can be coagulated by irradiating the target site with microwaves. Further, if necessary, by connecting the radiation electrode 24*c* electrically to radiation electrode 24*b*, a microwave between the upper jaw 14 and the cutter 15 irradiation morphism be configured to to solidify the biological tissue good.

The operation of the forceps 1 in which each element is configured as described above will be described below.

By a user who inserts a finger into the ring portion 113 of the main body frame 11 and the ring portion 131 of the trigger handle 13, the trigger handle 13 is set to the fixed handle frame 111 with the pivot portion 132 pivotally supported by the support shaft 115 as the center of rotation. Rotate in the approaching direction (the direction in which the lower part of the trigger handle 13 moves to the left in FIG. 1).

When the trigger handle 13 rotates around the pivot portion 132 in a direction approaching the fixed handle frame 111, the upper pivot portion 133 protruding upward from the pivot portion 132 moves toward the tip side (right side in FIG. 1). When the upper pivot portion 133 moves to the tip side F, the slide frame 12 that pivotally supports the upper pivot portion 133 with the upper support shaft 121 slides and moves to the tip side F along the reference frame 112.

When the slide frame 12 moves to the tip side F, the tip upper support shaft 122 that pivotally supports the rotary bearing portion 142 of the upper jaw portion 14 also moves to the tip side F. The upper jaw portion 14 in which the lower shafted portion 141 is pivotally supported by the tip support shaft 117 of the main body frame 11 and the rotary bearing portion 142 above it is pivotally supported by the tip upper support shaft 122 is the tip upper support shaft. Since 122 moves to the distal end side F, the distal end side F is pivoted in a direction approaching the lower jaw portion 116 with the distal end support shaft 117 as the center (see FIG. 4).

Further, as described above, in the cutter 15, the lower shafted portion 151 is pivotally supported by the tip support shaft 117 of the main body frame 11, and the upper rotation shaft portion 152 is pivotally supported by the tip upper support shaft 122. There is. Therefore, as the tip upper support shaft 122 moves to the tip side F, the cutter 15 pivots around the tip support shaft 117 in the direction in which the tip side F approaches the lower jaw portion 116 together with the upper jaw portion 14 (See FIG. 4).

At this time, since the upper end of the cutter 15 is regulated by the protrusion restricting portion 143 of the upper jaw portion 14, as described above, the cutter 15 is moved as the tip upper support shaft 122 moves to the tip side F. Although the tip side F pivots in the direction approaching the lower jaw 116 together with the upper jaw 14 around the tip support shaft 117, even if the pivot of the cutter 15 is delayed from the pivot of the upper jaw 14, the protrusion is restricted. The portion 143 causes the upper jaw portion 14 and the cutter 15 to both pivot.

As a result, in the initial state (open state) as shown in FIG. 6 at (a), the blood vessel B, which is the target site in the living tissue, is arranged between the upper jaw portion 14 and the lower jaw portion 116, and as shown in FIG. 6 at (b). By sandwiching the blood vessel B between the upper surface of the lower jaw portion 116 and the bottom surface of the upper jaw portion 14, the blood vessel B can be gripped and seated by the gripping mechanism 17 composed of the lower jaw portion 116 and the upper jaw portion 14. In addition, in order to avoid the problem that the position of the microwave irradiation part and the tissue coagulation is displaced, which may be a problem in the case of a thick blood vessel, an operator grips it with the forceps of the present application, crashes it to perform coagulation, and seal the blood vessel once. By gripping the side of the sealed part again, crashing, coagulating, and cutting, the proximal side of the thick blood vessel is sealed twice, and the peripheral side may be sealed by the blade.

Although the tip upper support shaft 122 is loosely fitted in the rotary bearing portion 142 formed in the elongated hole shape, the upper jaw portion 14 and the cutter 15 are separated from the lower jaw portion 116 by the spring 16. Since it is urged, the upper tip support shaft 122 does not move in the rotary bearing portion 142, and the upper jaw portion 14 and the cutter 15 rotate as described above.

At this time, the click convex portion 118 provided on the upper surface of the reference frame 112 and the click convex portion 123 provided on the bottom surface of the slide frame 12 are separated from each other in the longitudinal direction L in the initial state (open state). As shown in the enlarged view of the portion A in FIG. 4 at (b), the slide frame 12 slides toward the tip end side F with respect to the reference frame 112, so that the slide frame 12 approaches and abuts or contact in the longitudinal direction L.

As described above, the trigger handle 13 is operated to grip the target site such as the blood vessel B in the state shown in FIG. 4 and FIG. 6 at (b) in which the upper jaw portion 14 is close to the lower jaw portion 116 by the gripping mechanism 17. It is called a gripping state.

When the trigger handle 13 is further operated in the direction closer to the fixed handle frame 111 from this gripped state, the slide frame 12 is further moved to the tip side F with respect to the reference frame 112 (crash).

Further, when the slide frame 12 moves to the tip side F, the cutter 15 is pivoted by the cutting blade 153 over the upper surface of the lower jaw portion 116 with the tip support shaft 117 as the center, as shown in FIG. 5 at (b). It will move.

As a result, as shown in FIG. 6 at (c), the cutter 15 moves along the side surface of the upper jaw portion 14, and the blood vessel B gripped by the gripping mechanism 17 can be cut by the cutting blade 153 of the cutter 15.

As described above, by further operating the trigger handle 13, as shown in FIG. 5 at (b), the cutting state in which the cutter 15 is rotated so that the cutting blade 153 exceeds the upper surface of the lower jaw portion 116 is in the cutting state.

However, the upper jaw portion 14 is in contact with the upper surface of the lower jaw portion 116, and cannot rotate even if the slide frame 12 further slides. By that amount, the tip upper support shaft 122 moves in the elongated hole-shaped rotary bearing portion 142, and the slide frame 12 moves relative to the upper jaw portion 14.

As described above, the cutter 15 rotates further due to the further movement of the slide frame 12, but the support shaft 122 on the tip of the rotary bearing portion 142 moves and the upper jaw portion 14 does not rotate, that is, the length. The upper jaw portion 14 and the cutter 15 are differentiated in the rotational direction around the tip support shaft 117 by a differential mechanism in which the tip upper support shaft 122 moves on the hole-shaped rotary bearing portion 142. The spring 16 is deformed in the contracting direction due to the differential between the upper jaw portion 14 and the cutter 15. Therefore, when the force for operating the trigger handle 13 is released, the compression of the compression coil spring 13*a* shown in FIG. 1 is released, the slide frame 12 moves to the proximal end side R, and the urging force of the spring 16 opens the cutter 15. Along with the movement in the direction, the upper jaw portion 14, that is, both members 14 and 15, cooperate to automatically return to the open state of FIG. 1.

Even if the pivot of the cutter 15 in the opening direction is faster than the pivot of the upper jaw 14 in the opening direction due to the urging force of the spring 16, the upper end of the cutter 15 is regulated by the protrusion restricting portion 143. Therefore, both the upper jaw portion 14 and the cutter 15 are pivoted in the opening direction, and it is possible to prevent the upper portion of the cutter 15 from protruding upward from the upper surface of the upper jaw portion 14.

Further, in this cut state, the click convex portion 118 and the click convex portion 123 that are in contact with each other in the above-mentioned gripping state are as shown in the enlarged view of the A portion in FIG. 5 at (b). While the click convex portion 118 and the click convex portion 123 are bent, one of them gets over the other, so that a click feeling is generated. Since this click feeling is transmitted to the user via the main body frame 11 and the trigger handle 13, the user recognizes that the disconnected state has been reached, that is, in a series of operations of the trigger handle 13, the gripped state is changed to the disconnected state. The clicked protrusions 118 and 123 can notify the user.

When the force for operating the trigger handle 13 is released and the slide frame 12 moves to the base end side R and returns to the initial state (open state), the inclination angle exceeds the gentle surface side, so that the slope is steep. There is no click feeling like when the sloped surfaces get over each other.

As described above, the forceps 1 performs gripping of the target site such as the blood vessel B by the upper jaw portion 14 and the lower jaw portion 116 constituting the gripping mechanism 17, and cutting of the target site by the cutter 15 in the gripping/crashing state by a series of operations by the handle 13. Then, during the gripping, crashing, cutting of the target site by a series of operations of the trigger handle 13, the target site can be coagulated by irradiating the target site with a microwave from the irradiation electrode 24.

Further, since the differential mechanism is provided by the elongated hole-shaped rotary bearing portion 142 that loosely fits the support shaft 122 on the tip, in a series of operations of the trigger handle 13, after gripping by the gripping mechanism 17, the target site may be cut by the cutter 15. Further, it is possible to provide a notification unit for notifying the user by the click convex portions 118 and 123 of the transition from the gripping state to the cutting state in the series of operations of the trigger handle 13.

The notification unit may have a structure in which a moving sensor is attached instead of the click protrusions 118 and 123 to notify the user by an electronic signal or an optical signal. According to this embodiment, it is possible to provide a multifunctional forceps for gripping, coagulating, or cutting alone or in combination.

Subsequently, the forceps 1X of another embodiment are shown in FIGS. 7 to 11.

Figure 7:
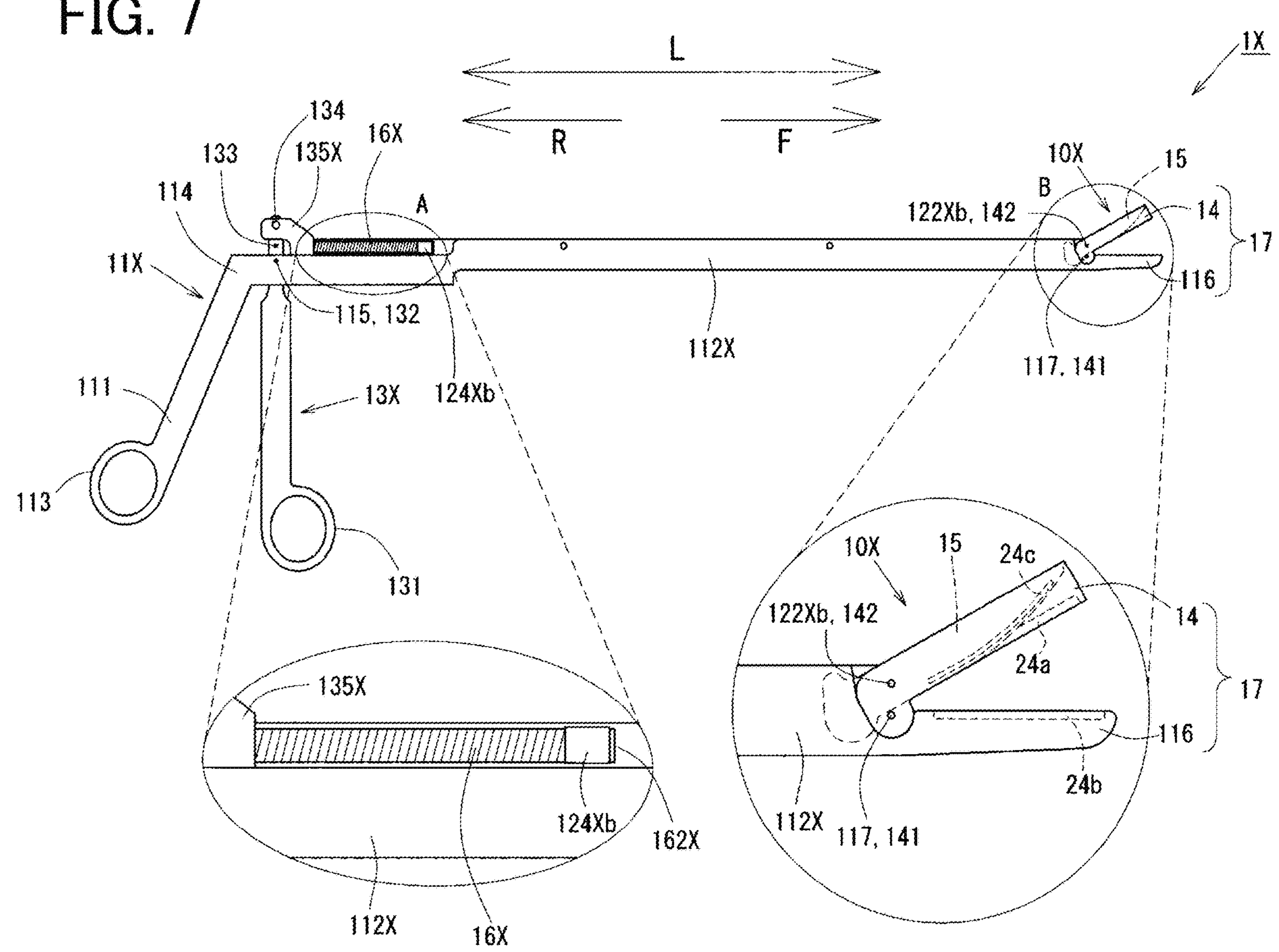
FIG. 7 is a front view of forceps of another embodiment of the present invention.
Figure 8:
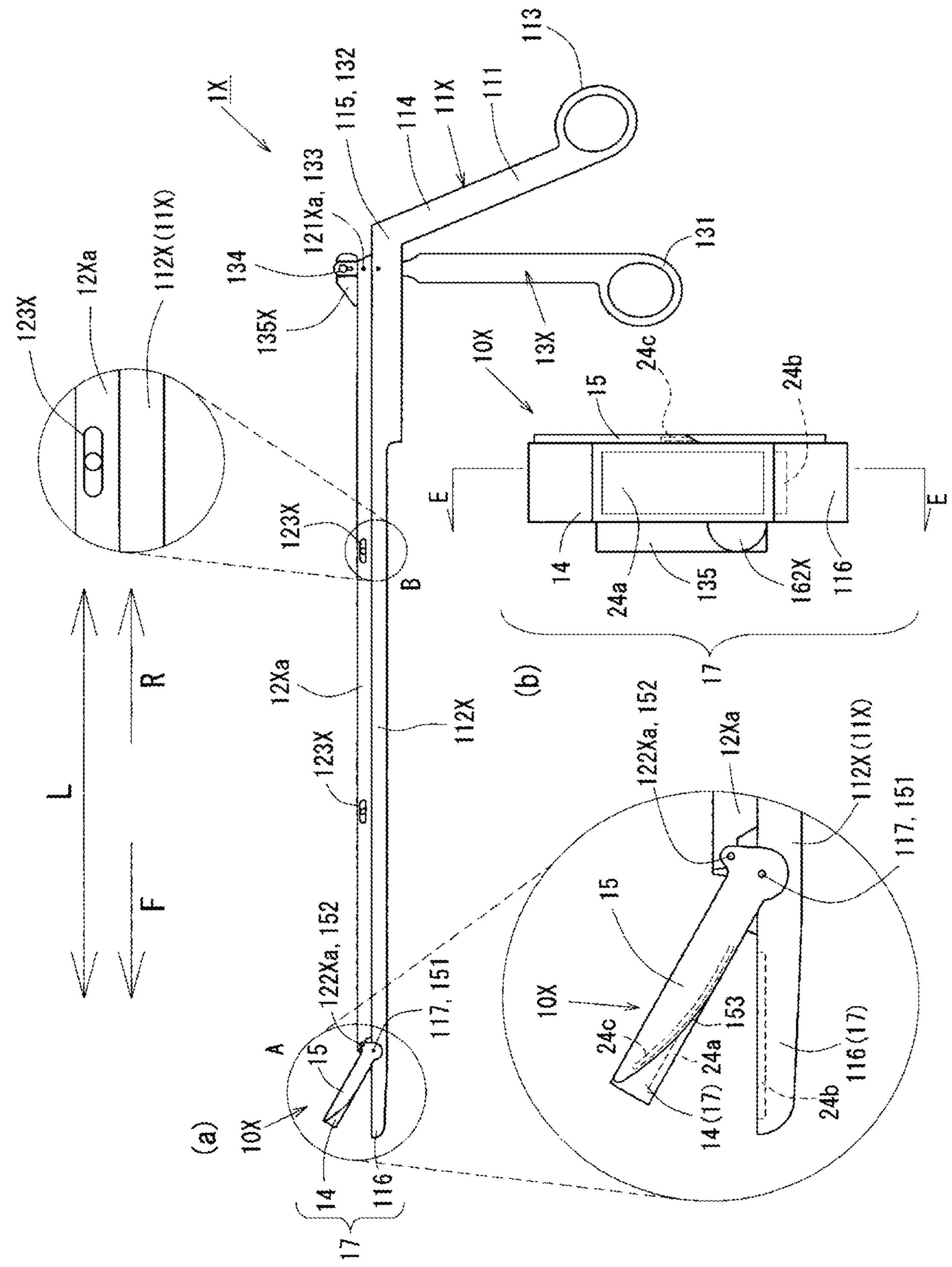
FIG. 8 is an explanatory view of the forceps of FIG. 7.

FIG. 7 shows a front view of the forceps 1X of this embodiment. FIG. 8 shows an explanatory diagram of the forceps 1X of FIG. 8 at (a) shows a rear view of the forceps 1X, and FIG. 8 at (b) shows a side view of the forceps 1X on the cutting mechanism side.

Figure 9:
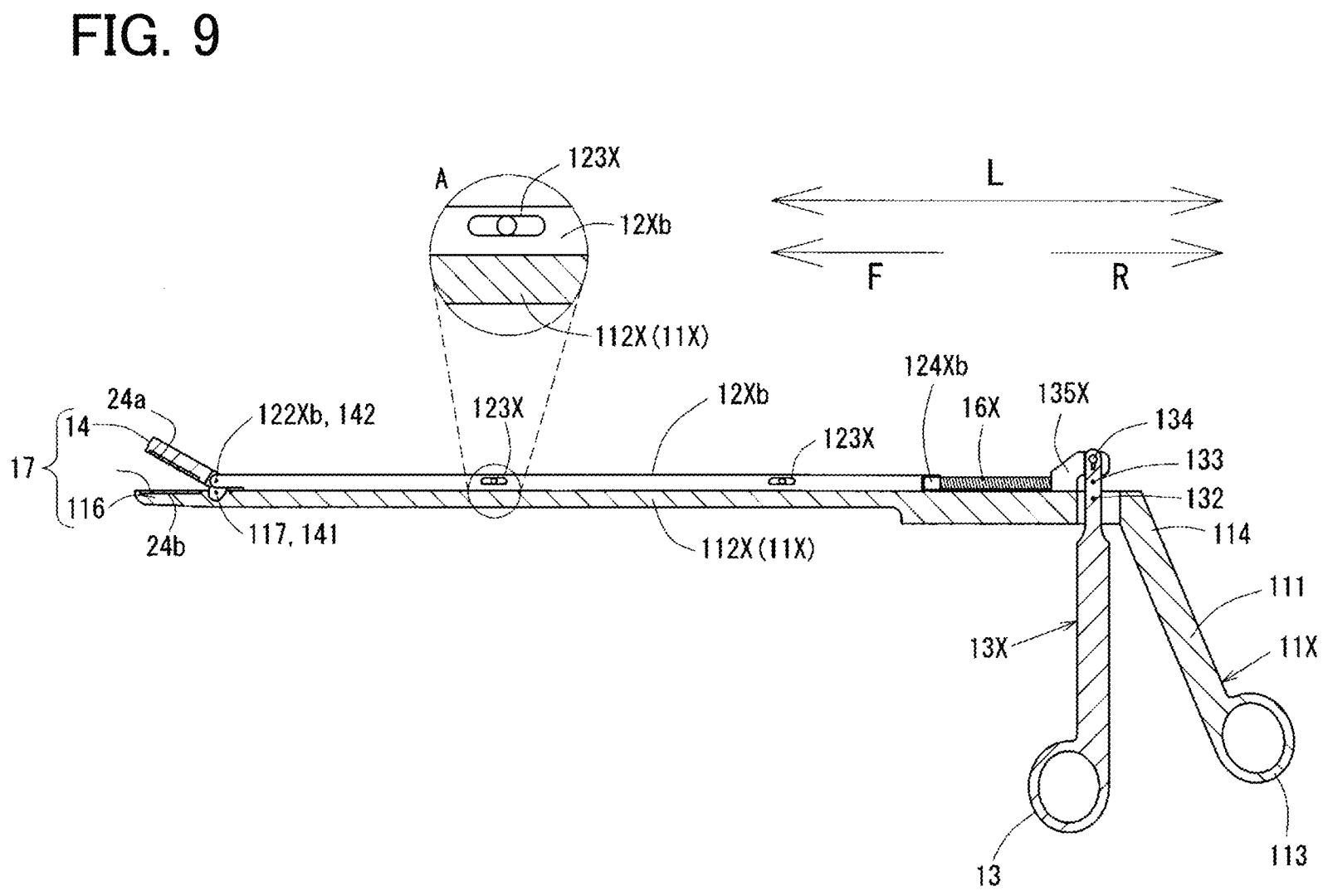

FIG. 9 shows a rear view of the forceps 1X of FIG. FIG. 8 at (b) shows a partial cross-sectional view taken along the line E-E.

Figure 10:
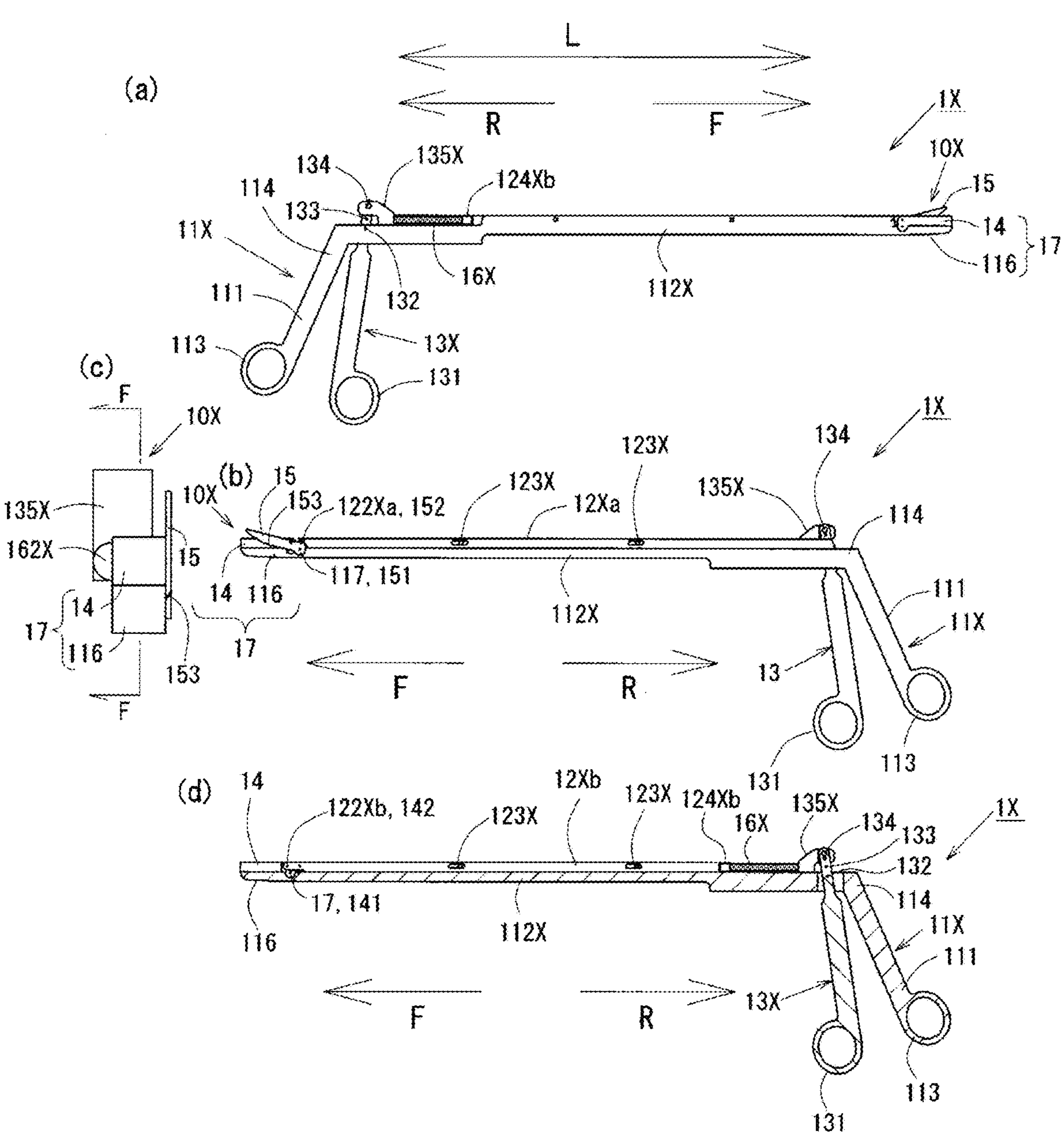
FIG. 10 is an explanatory view of a gripped state of the forceps of FIG. 7.

FIG. 10 shows an explanatory view of the forceps 1X in the gripped state. FIG. 10 at (a) shows a front view of the forceps 1X in the gripped state, FIG. 10 at (b) shows a rear view of the forceps 1X in the same state, and FIG. 10 at (c) shows the cutting mechanism side of the forceps 1X in the same state. A side view is shown, and FIG. 10 at (d) shows a partial cross-sectional view taken along the line F-F in FIG. 10 at (c).

Figure 11:
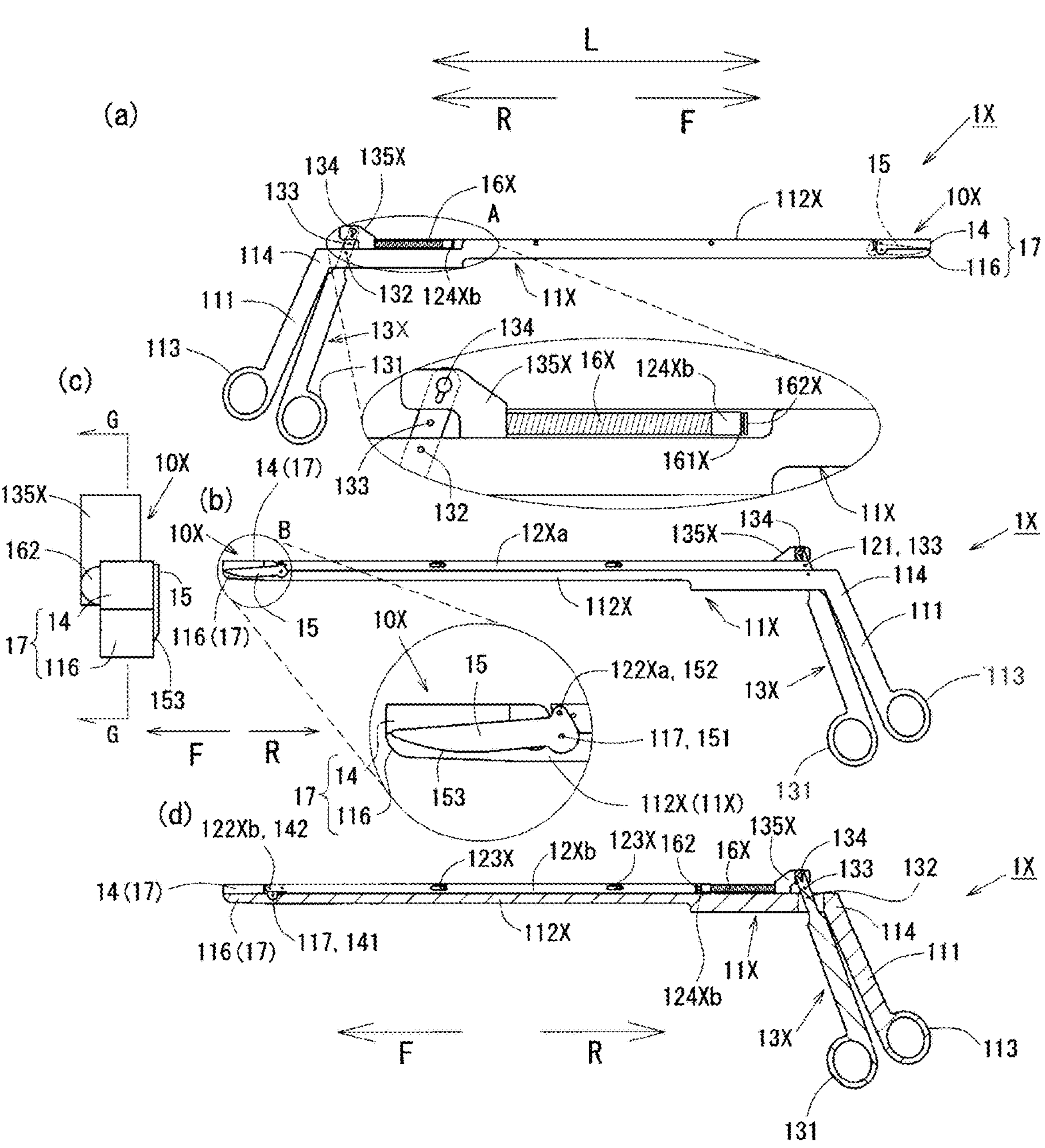
FIG. 11 is an explanatory view of a cut state of the forceps of FIG. 7.

FIG. 11 shows an explanatory diagram of the forceps 1X in the cut state. 11 at (a) shows a front view of the forceps 1X in the cut state, FIG. 11 at (b) shows a rear view of the forceps 1X in the same state, and FIG. 11 at (c) shows the cutting mechanism side of the forceps 1X in the same state. A side view is shown, and FIG. 11 at (d) shows a partial cross-sectional view taken along the line GG in FIG. 11 at (c).

In the following description of the forceps 1X, the same components as those of the forceps 1 are designated by the same reference numerals, and detailed description thereof will be omitted.

The forceps 1X includes a main body frame 11X, a first slide plate 12Xa, a second slide plate 12Xb, a trigger handle 13X, an upper jaw portion 14, a cutter 15, and a coil spring 16X.

In the forceps 1X, the first slide plate 12Xa and the second slide plate 12Xb slide with respect to the reference frame 112 with respect to the forceps 1 in which the slide frame 12 slides on the upper surface of the reference frame 112 of the main body frame 11 in the longitudinal direction L. Then, the upper jaw portion 14 and the cutter 15 are configured to rotate. [0083].

More specifically based on FIG. 7, the main body frame 11X is composed of the fixed handle frame 111 and the reference frame 112X that intersect at an obtuse angle, similarly to the main body frame 11 composed of the fixed handle frame 111 and the reference frame 112 of FIG. 1.

As shown in FIG. 10 at (a) and (b), the reference frame 112X has a first slide plate on the upper half portion on the back side with respect to the reference frame 112 in which the slide frame 12 of FIG. 1 slides along the upper surface. A slide groove at (not shown) is formed in which the 12Xa and the second slide plate 12Xb slide.

The first slide plate 12Xa and the second slide plate 12Xb are formed in a plate shape, are laminated in the slide groove provided in the reference frame 112X in the thickness direction, and are independently slidably stored.

As shown in FIG. 8, the base end side R of the first slide plate 12Xa is provided with a middle support shaft 121Xa that pivotally supports the upper pivot portion 133 provided on the trigger handle 13X, and the tip side F is provided with a middle stage support shaft 121Xa. A support shaft 122Xa on the tip that pivotally supports the cutter 15 is provided.

As shown in FIG. 9, on the distal end side F of the second slide plate 12Xb, a tip upper support shaft 122Xb for supporting the cutter 15 is provided.

In addition, as shown in FIG. 11, a first base end side R is provided with a contact ring portion 124Xb through which the coil spring 16X abuts and the insertion shaft 161X through which the inside of the coil spring 16X is inserted.

The second slide plate 12Xb configured in this way is formed to have a length that is about the length of the coil spring 16X, which will be described later, and a length that the proximal end side R is shorter than that of the first slide plate 12Xa.

Further, the first slide plate 12Xa and the second slide plate 12Xb which are laminated and arranged in the thickness direction in the slide groove provided in the reference frame 112X are arranged so that the first slide plate 12Xa is on the back side. Therefore, the second slide plate 12Xb is sandwiched between the reference frame 112X and the first slide plate 12Xa in the front-back direction.

The first slide plate 12Xa and the second slide plate 12Xb are provided with a long hole-shaped regulation hole 123X long in the longitudinal direction L into which the slide frame 112Xa provided in the slide groove of the reference frame 112X is loosely fitted.

The trigger handle 13X is provided in addition to the axis portion 132 and the axis portion 133, as compared with the axis portion 132 and the trigger handle 13 (FIG. 1) in which the axis portion 133 is provided on the upper end side of the axis portion 132 with the upper axis portion 134 provided above the upper axis portion 133. Further, the upper pivot portion 134 of the trigger handle 13X is rotatably provided with a pressing block 135X having an insertion shaft 161X. The compression coil spring 13*a* described with reference to FIG. 1 may be provided between the fixed handle frame 111 of the main body frame 11X and the trigger handle 13X. The trigger handle 13X is in addition to the axis portion 132 and the axis portion 133, as compared with the axis portion 132 and the trigger handle 13 (see FIG. 1) in which the axis portion 133 is provided on the upper end side of the axis portion 132. The upper axis portion 134 is provided above the upper axis portion 133. Further, the upper pivot portion 134 of the trigger handle 13X is rotatably provided with a pressing block 135X having an insertion shaft 161X. The compression coil spring 13*a* described with reference to FIG. 1 may be provided between the fixed handle frame 111 of the main body frame 11X and the trigger handle 13X.

The insertion shaft 161X is inserted through the inside of the coil spring 16X and is inserted into the contact ring portion 124Xb. A flange portion 162X having a diameter larger than that of the abutting ring portion 124Xb is provided at the end portion of the tip side F of the insertion shaft 161X.

When the trigger handle 13X is operated, the forceps 1X having each element configured in this way moves the upper pivot portion 133X and the upper pivot portion 134 to the tip side F with the pivot portion 132 as the rotation axis.

When the upper pivot portion 133 moves to the tip side F, the first slide plate 12Xa having the middle stage support shaft 121 that pivotally supports the upper pivot portion 133 slides to the tip side F with respect to the reference frame 112X.

As shown in FIG. 10, when the first slide plate 12Xa moves to the tip side F, the cutter 15 that pivotally supports the rotation shaft portion 152 with the tip upper support shaft 122Xa is pivotally supported by the tip support shaft 117. It rotates along the side surface of the upper jaw portion 14 with the portion 151 as an axis.

On the other hand, when the upper pivot portion 134 moves to the tip side F, the pressing block 135X rotatably provided on the upper pivot portion 134 also moves to the tip side F.

When the pressing block 135X moves, the coil spring 16X through which the insertion shaft 161X is inserted is pressed against the tip side F. Since the tip side F of the coil spring 16X pressed against the tip side F by the pressing block 135X is in contact with the contact ring portion 124Xb, the contact ring portion 124Xb is pressed against the tip side F and the second slide plate 12Xb is moved.

When the second slide plate 12Xb moves to the tip side F, the lower shafted portion 141 is pivotally supported by the tip support shaft 117 of the main body frame 11X, and the rotary bearing portion 142 above it is pivotally supported by the tip upper support shaft 122Xb. In the upper jaw portion 14, the tip upper support shaft 122Xb moves to the tip side F. As a result, the tip side F pivots in the direction approaching the lower jaw portion 116 around the tip support shaft 117, and the target site such as the blood vessel B is gripped by the gripping mechanism 17 composed of the lower jaw portion 116 and the upper jaw portion 14. It is in a gripping state (see FIG. 10).

In the first slide plate 12Xa and the second slide plate 12Xb that move to the tip (distal end) side F by operating the trigger handle 13X, the slide amount of the second slide plate 12Xb that pivotally supports the upper stage pivot portion 134 whose distance from the pivot portion 132 is longer than that of the first slide plate 12Xa that pivotally supports the upper pivot portion 133.

When the trigger handle 13X is further operated in the direction closer to the fixed handle frame 111 from this gripped state, the first slide plate 12Xa is further moved to the tip side F with respect to the reference frame 112X.

Further, when the first slide plate 12Xa moves to the tip side F, as shown in the enlarged view of the portion B in FIG. 11 at (b), the cutting blade 153 of the cutter 15 centering on the tip support shaft 117 pivots beyond the upper surface of the lower jaw portion 116.

As a result, the cutter 15 moves along the upper jaw portion 14, and the blood vessel B gripped by the gripping mechanism 17 becomes in a cutting state in which the blood vessel B may be cut by the cutting blade 153 of the cutter 15.

However, the upper jaw portion 14 is in contact with the upper surface of the lower jaw portion 116, and cannot rotate even if the second slide plate 12Xb further slides.

When the trigger handle 13X is further operated in the direction closer to the fixed handle frame 111, the upper pivot portion 134 also moves to the tip (distal end) side F, and the pressing block 135X also moves to the tip side F together with the upper pivot portion 134. However, as described above, since the upper jaw portion 14 cannot be further rotated, the second slide plate 12Xb also cannot slide.

Therefore, the coil spring 16X contracts and comes close to the contact ring portion 124Xb of the second slide plate 12Xb that cannot slide and the pressing block 135X. That is, when the coil spring 16X contracts, the contact ring portion 124Xb and the pressing block 135X are differentiated, and the trigger handle 13X is operated in a direction further closer to the fixed handle frame 111, so that the cutter 15 rotates. However, the upper jaw portion 14 may generate a differential that does not rotate.

As described above, the coil spring 16X is deformed in the contracting direction in the cutting state in which the cutter 15 and the upper jaw portion 14 are differentially operated by the further operation of the trigger handle 13X. Therefore, when the force for operating the trigger handle 13X is released, the trigger handle 13X moves in the expanding direction via the pressing block 135X due to the urging force of the coil spring 16X.

The facing surfaces of the first slide plate 12Xa and the second slide plate 12Xb may be provided with the same configuration as the click convex portion 118 and the click convex portion 123 in the forceps 1 of FIG. 2. Even in this case, one of the click feeling generated when overcoming the other makes the user to recognize cutting state.

As described above, the forceps 1X of this embodiment also has the same gripping state as the forceps 1 of FIG. 1. Gripping the target site such as blood vessel B by the upper jaw portion 14 and the lower jaw portion 116 constituting the grip mechanism 17 and cutting the target site by the cutter 15 in the gripped state may be performed by a series of operations by the trigger handle 13X. Then, during the gripping, crashing, and cutting of the target portion by a series of operations of the trigger handle 13X, the target portion can be coagulated by irradiating the target portion with a microwave from the irradiation electrode 24.

Further, since the coil spring 16X is provided with a differential mechanism by contracting, the target site can be cut by the cutter 15 after gripping and pressing by the gripping mechanism 17 in a series of operations of the trigger handle 13X.

The upper jaw portion 14 of the forceps 1X may be provided with a protrusion restricting portion (see 143 of FIG. 3 at (a)) that restricts the cutter 15 from protruding from the upper surface of the upper jaw portion 14. As a result, the cutter 15 does not protrude from the upper surface of the upper jaw portion 14, and can be used safely.

Subsequently, the forceps 1Y of another embodiment will be described with reference to FIGS. 12 to 15.

Figure 12:
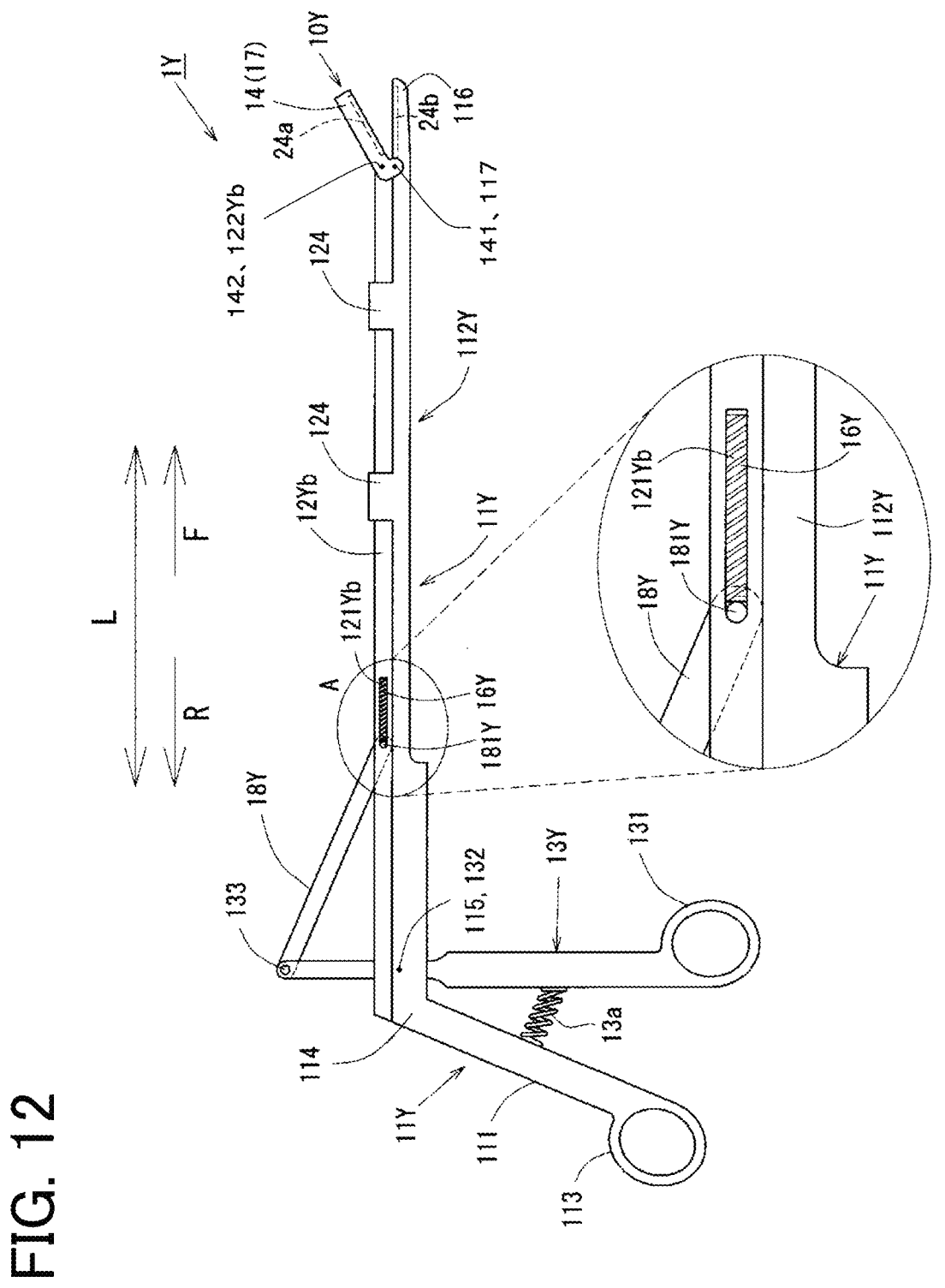
Figure 13:
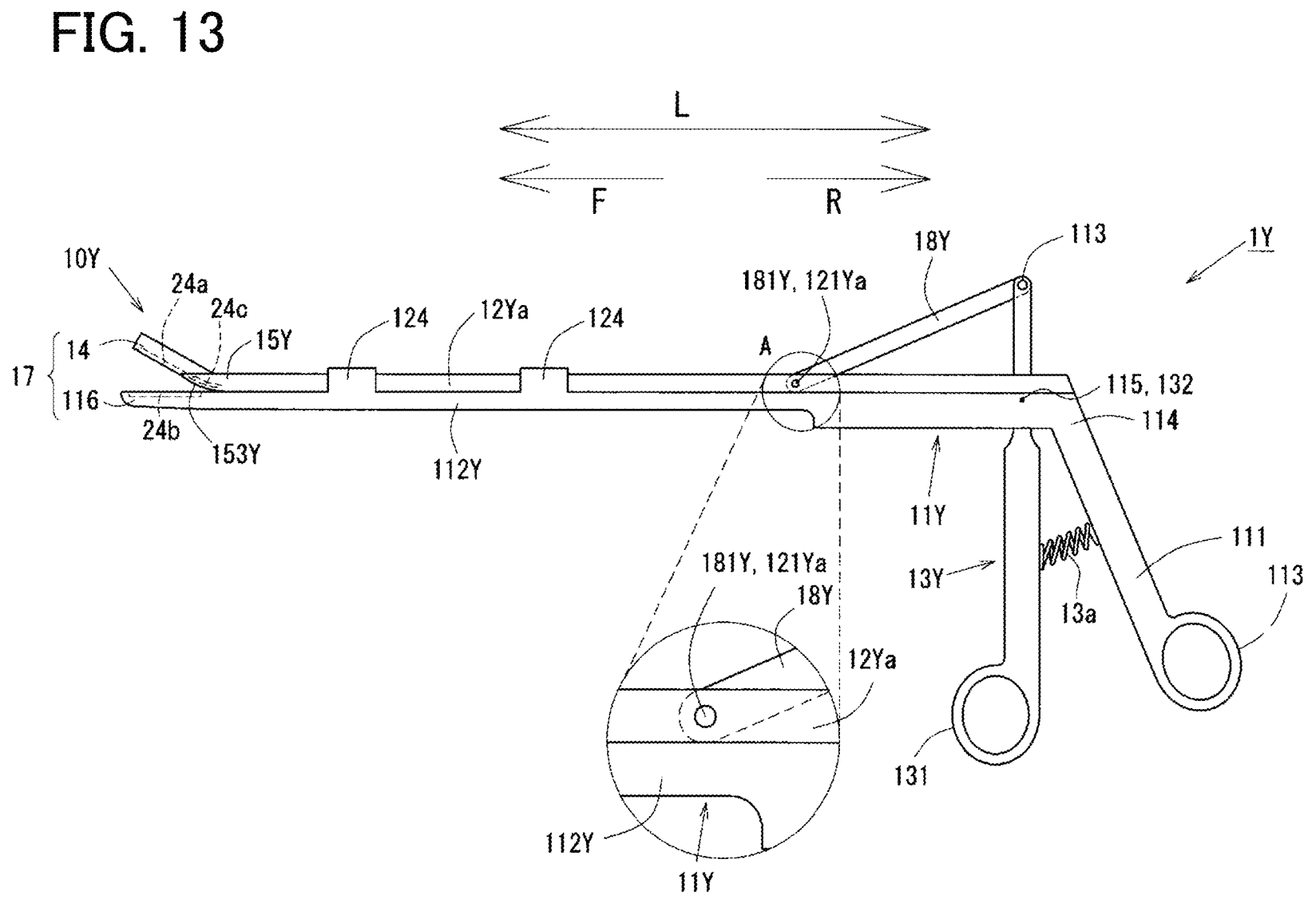

FIG. 12 shows a front view of the forceps 1Y of this embodiment, and FIG. 13 shows a rear view of the forceps 1Y of FIG. 12.

Figure 14:
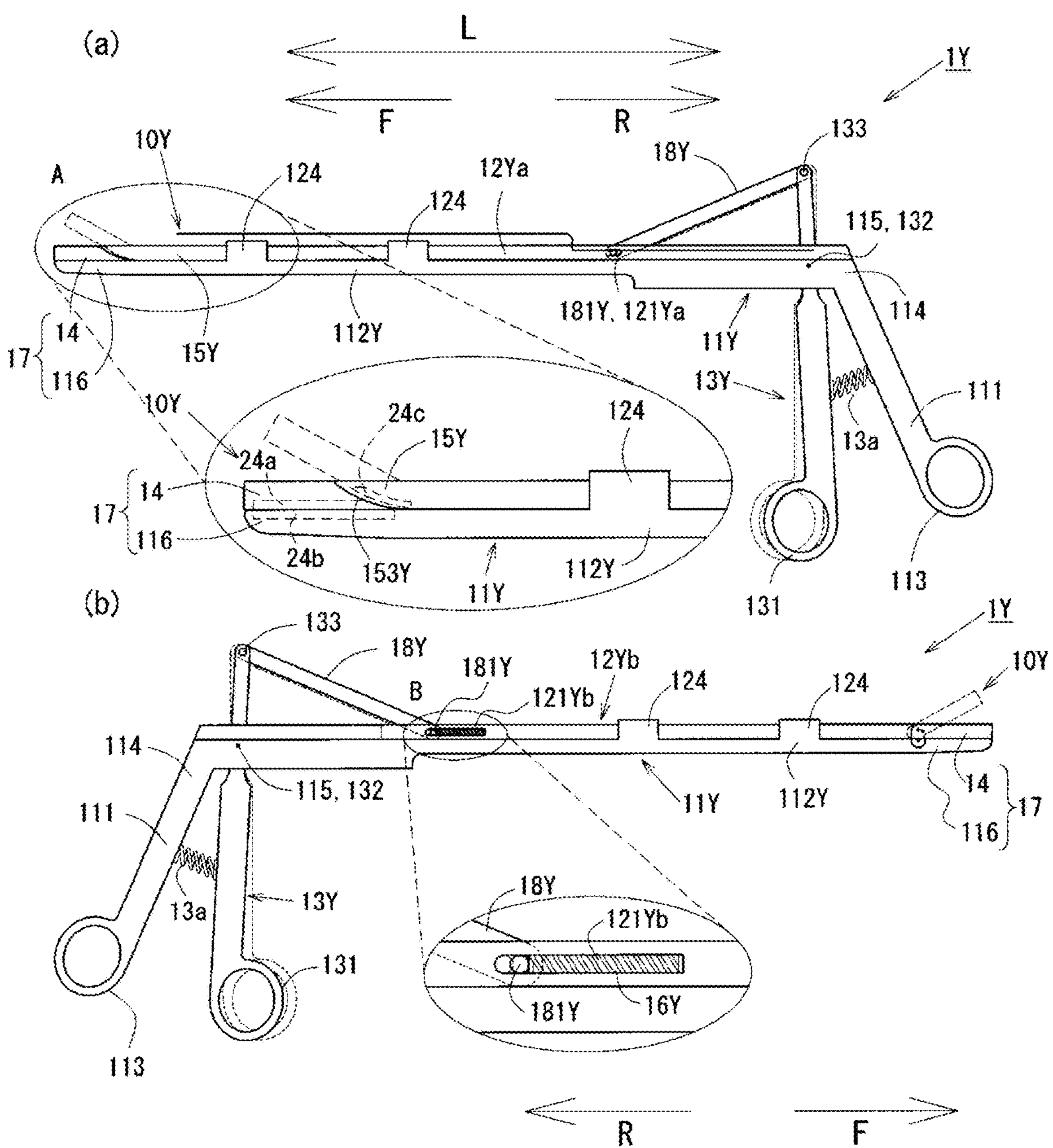
FIG. 14 is an explanatory view of a gripped state of the forceps of FIG. 12.

FIG. 14 shows an explanatory view of the forceps 1Y in the gripped state. FIG. 14 at (a) shows a front view of the forceps 1Y in the gripped state, and FIG. 14 at (b) shows a rear view of the forceps 1Y in the same state.

Figure 15:
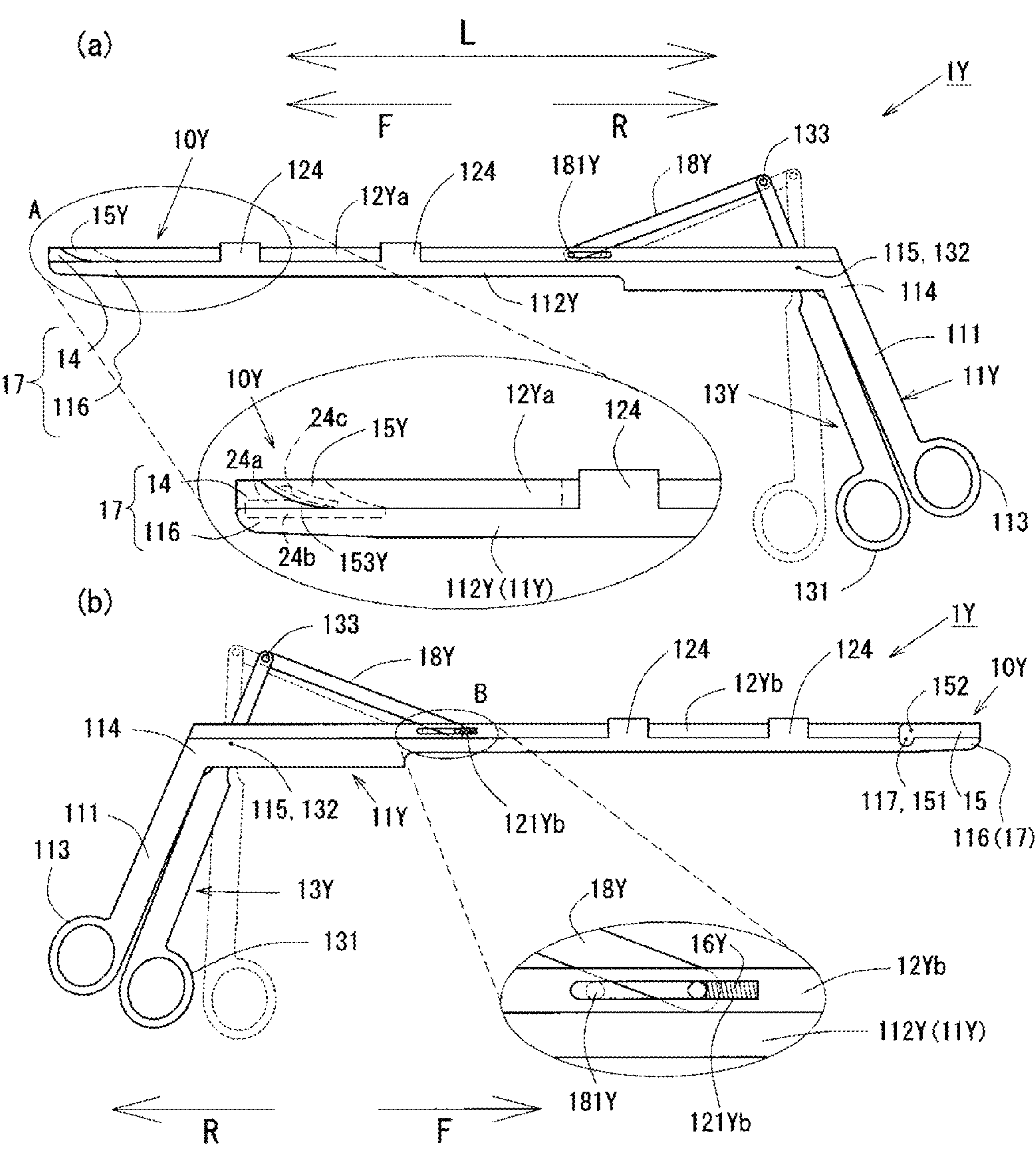
FIG. 15 is an explanatory view of forceps in a cut state.

FIG. 15 shows an explanatory diagram of the forceps 1Y in the cut state. FIG. 15 at (a) shows a front view of the forceps 1Y in the cut state, and FIG. 15 at (b) shows a rear view of the forceps 1Y in the same state.

In the following description of forceps 1Y, the same components as those of forceps 1 in FIG. 1 and forceps 1X in FIG. 7 are designated by the same reference numerals, and detailed description thereof will be omitted.

In FIG. 12, the forceps 1Y includes a main body frame 11Y, a first slide plate 12Ya (see FIG. 13), a second slide plate 12Yb, a trigger handle 13Y, an upper jaw portion 14, and a slide cutter 15Y (see FIG. 13). And a coil spring 16Y.

With respect to the forceps 1 in which the slide frame 12 slides in the longitudinal direction L on the upper surface of the reference frame 112 of the main body frame 11 shown in FIG. 1, the forceps 1Y has the upper jaw in which the second slide plate 12Yb slides with respect to the reference frame 112Y. The portion 14 rotates, and the slide cutter 15Y is configured to slide and cut along with the slide of the first slide plate 12Y provided at the end portion of the tip side F.

More specifically, the main body frame 11Y is composed of the fixed handle frame 111 and the reference frame 112Y that intersect at an obtuse angle, similarly to the main body frame 11 composed of the fixed handle frame 111 and the reference frame 112 shown in FIG. 1.

Similar to the reference frame 112 in which the slide frame 12 shown in FIG. 1 slides along the upper surface, the first slide plate 12Ya and the second slide plate 12Yb are configured to slide along the upper surface of the reference frame 112Y. The reference frame 112Y is provided with a regulation frame 124 that regulates the first slide plate 12Ya and the second slide plate 12Yb that slide along the upper surface so as to be slidable.

The first slide plate 12Ya and the second slide plate 12Yb are formed in a plate shape, are laminated in the thickness direction, and are independently slidable along the upper surface of the reference frame 112Y and are regulated by the regulation frame 124.

In FIG. 13, a slide cutter 15Y is provided at the end of the tip end side F of the first slide plate 12Ya, and an upper support shaft 121Ya for pivotally supporting the drive shaft 181Y of the arm 18Y described later is provided at the intermediate portion.

Returning to FIG. 12, an upper support shaft 121Yb that pivotally supports the drive shaft 181Y of the arm 18Y, which will be described later, is provided in the middle portion of the second slide plate 12Yb to which the upper jaw portion 14 is connected to the tip.

The upper support shaft 121Yb has a long hole shape long in the longitudinal direction L, and the drive shaft 181Y can be pivotally supported in the longitudinal direction L. Further, inside the upper support shaft 121Yb, a coil spring 16Y that urges the drive shaft 181Y to the base end side R (left side in FIG. 12) is arranged on the tip end side F of the drive shaft 181Y.

The trigger handle 13Y is provided with an upper pivot portion 133 above the pivot portion 132 pivotally supported by the reference frame 112Y so as to project upward from the first slide plate 12Ya and the second slide plate 12Yb.

An arm 18Y tilting downward and on the tip side F is connected to the upper pivot portion 133, and the above-mentioned drive shaft 181Y is provided at the tip of the arm 18Y.

When the trigger handle 13Y is operated, the forceps 1Y having each element configured in this way moves the upper pivot portion 133 to the tip end side F with the pivot portion 132 as the rotation axis.

When the upper pivot portion 133 moves to the tip side F, the arm 18Y connected to the upper pivot portion 133 also moves to the tip side F while changing the inclination angle. When the arm 18Y moves to the tip side F while the inclination angle changes, the first slide plate 12Ya (FIG. 13) that pivotally supports the drive shaft 181Y of the arm 18Y with the upper support shaft 121Y slides to the tip side F with respect to the reference frame 112Y.

As shown in the enlarged view of the portion A in FIG. 14 at (a), when the first slide plate 12Ya moves to the tip side F, the slide cutter 15Y provided on the tip side F of the first slide plate 12Ya also moves to the tip side F along the upper surface of the lower jaw portion 116 in the reference frame 112Y. However, the cutting blade 153Y of the slide cutter 15Y moving to the tip side F is moved to the extent that it does not overlap the middle portion of the upper jaw portion 14.

Further, as shown in the enlarged view of the portion B in FIG. 14 at (b), the arm 18Y moves to the tip side F while the inclination angle changes as described above with the movement of the upper pivot portion 133 to the tip side F. When it moves, the drive shaft 181Y is loosely fitted to the upper support shaft 121Yb and is urged to the proximal end side R along the coil spring 16Y, so that the second slide plate 12Yb also moves to the distal end side F.

More specifically, in FIG. 12, when the second slide plate 12Yb moves to the tip side F, similar to the operation as in FIG. 1, the lower shafted portion 141 is pivotally supported by the tip support shaft 117 of the main body frame 11Y, and regarding the upper jaw portion 14 whose upper rotary bearing portion 142 is pivotally supported by the tip upper support shaft 122Yb, the tip upper support shaft 122Yb moves to the tip side F. As a result, the tip side F is pivotally moved in the direction approaching the mandibular portion 116 around the tip support shaft 117 as the center, and as shown in FIG. 14 at (b), the gripping mechanism 17 composed of the lower jaw portion 116 and the upper jaw portion 14 brings the target site such as blood vessel B in a gripping state where the target site may be gripped.

When the trigger handle 13Y is further operated in the direction closer to the fixed handle frame 111 from this gripped state, the first slide plate 12Ya moves further to the tip end side F with respect to the reference frame 112.

As shown in FIG. 15 at (a), when the first slide plate 12Ya is further moved to the tip side F, the slide cutter 15Y provided at the tip of the first slide plate 12Ya moves around the tip support shaft 117, and the blade 153Y moves to the vicinity of the tip surface of the upper jaw portion 14.

Thus, the slide cutter 15Y moves along the reference frame 112Y, and the vessel B gripped by the gripping mechanism 17 is cut by the cutting blade 153Y of the slide cutter 15Y.

However, the upper jaw portion 14 is in contact with the upper surface of the lower jaw portion 116, and cannot rotate even if the second slide plate 12Yb further slides.

When the trigger handle 13Y is further operated in a direction closer to the fixed handle frame 111, the drive shaft 181Y of the arm 18Y pivotally supported by the upper pivot portion 133 also moves to the tip end side F. However, as described above, the second slide plate 12Yb cannot slide to the tip side F. Therefore, the drive shaft 181Y presses the coil spring 16Y toward the tip end side F to contract the drive shaft 181Y against the urging force of the coil spring 16Y that urges the drive shaft 181Y to the proximal end side R. That is, as shown in FIG. 15 at (b), which is an enlarged view of the portion A in FIG. 15 at (a), the trigger handle 13Y is operated in a direction further closer to the fixed handle frame 111, and the coil spring 16Y contracts to slide. The cutter 15Y slides to the tip side F, but the upper jaw portion 14 may generate a differential operation that it does not rotate.

As described above, the coil spring 16Y is deformed in the contracting direction in the cutting state in which the slide cutter 15Y and the upper jaw portion 14 are differentially operated by the further operation of the trigger handle 13Y. Therefore, when the force for operating the trigger handle 13Y is released, the trigger handle 13Y moves in the expanding direction via the arm 18Y due to the urging force of the compression coil spring 13*a*.

The facing surfaces of the first slide plate 12Ya and the second slide plate 12Yb may be provided with the same configuration as the click convex portion 118 and the click convex portion 123 in the forceps 1 of FIG. 4 at (b) described above. Even in this case, the user can be made to recognize that the user has been disconnected by the click feeling generated when one gets over the other.

As described above, the forceps 1Y also grips the target site such as the blood vessel B by the upper jaw portion 14 and the lower jaw portion 116 constituting the gripping mechanism 17 and cuts the target site of the gripped state by the slide cutter 15Y which may be performed by a series of operations by the trigger handle 13, similarly to the forceps 1 in FIG. 1 and the forceps 1X in FIG. 7. Then, during the gripping/crashing/cutting of the target site by a series of operations of the trigger handle 13, the target site can be coagulated by irradiating the target site with a microwave from the irradiation electrode 24.

Further, since the coil spring 16Y is provided with a differential mechanism by contracting, the target site may be cut by the slide cutter 15Y after being gripped by the gripping mechanism 17 in a series of operations of the trigger handle 13.

Next, FIGS. 16 and 17 show an end effector 10*a* for microwave irradiation on a living tissue as another embodiment of the present invention. The forceps 1, 1X, and 1Y of the above-described embodiments all include an irradiation electrode 24 for irradiating an electromagnetic wave, and a specific electrode structure will be described in this embodiment.

FIG. 16 shows a schematic front view of the end effector 10*a* of this embodiment.

FIG. 17 shows a schematic explanatory view of the end effector 10*a* of FIG. 16. FIG. 17 at (a) shows a side by view taken along the line H-H in FIG. 16, FIG. 17 at (b) shows a partial vertical sectional view of the end effector 10*a*, and FIG. 17 at (c) shows an enlarged plane view of electrodes by view taken along the line I-I in FIG. 16. plane view The end effector 10*a* is used for a scissors-type multi-functional surgical instrument, and corresponds to the cutting mechanism 10 in the above-mentioned forceps 1. Therefore, the same components as those in the forceps 1 of the embodiment of FIG. 1 described above are designated by the same reference numerals. Further, the end effector in this embodiment may constitute the above-mentioned cutting device, cutting mechanism, and forceps, and includes other similar configurations.

In addition, in FIGS. 16 and 17, a part of the tip end side F of the end effector 10*a* is shown.

The end effector 10*a* has a reference shaft 11*a* (corresponding to the reference frame 112 in the cutting mechanism 10) that penetrates the bellows-shaped flexible portion 101 provided at the tip of the tubular support 100 attached to the scissors-type multifunctional surgical instrument, and a movable frame 12*a* (corresponding to the slide frame 12 in the cutting mechanism 10) provided with an upper jaw portion 14*a* (corresponding to the upper jaw portion 14 in the cutting mechanism 10) and a cutter 15*a* (corresponding to the cutter 15 in the cutting mechanism 10) at the tip.

In the reference shaft 11*a* and the movable frame 12*a*, the portion corresponding to the inside of the flexible portion 101 is configured to have flexibility that may be deformed following the movable flexible portion 101. However, a wire may be used as a drive.

The operation of the upper jaw portion 14*a* and the cutter 15*a* in the end effector 10*a* configured in this way is the same as that of the upper jaw portion 14 and the cutter 15 of the cutting mechanism 10 in the forceps 1 described above, and is movable with respect to the reference axis 11*a*. By moving the frame 12*a* in the longitudinal direction L, the target site is gripped and pressed by the gripping mechanism 17*a* composed of the lower jaw portion 116*a* and the upper jaw portion 14*a* provided at the end of the tip end side F of the reference shaft 11*a*, and the target site is cut. It may be cut with the cutter 15.

It should be noted that the cutter 15*a*, which protrudes to the back side and rotates along the side surface of the upper jaw portion 14*a* on the back side, is restricted from protruding upward from the upper surface of the upper jaw portion 14*a* on the tip side on the back side of the upper jaw portion 14*a*. It is provided with a protrusion control unit 143. As a result, even if the pivot of the cutter 15*a* in the opening direction is faster than the pivot of the upper jaw 14*a* in the opening direction, the upper end of the cutter 15*a* is regulated by the protrusion restricting portion 143, and the upper jaw portion 14*a* and Together with the cutter 15*a*, it is pivoted in the opening direction, and it is possible to prevent the upper portion of the cutter 15*a* from protruding upward from the upper surface of the upper jaw portion 14*a*.

A coaxial electrode 20 along the longitudinal direction L is provided on the upper surface of the lower jaw portion 116*a* and the bottom surface of the upper jaw portion 14*a* of the end effector 10*a* configured in this way.

Further, in the end effector 10*a*, coaxial cable 40 is connected with microwave generator 30 and the coaxial electrode 20. The microwave generator 30 may be provided inside the end effector 10*a*.

As shown in the enlarged cross-sectional view of the portion A in FIG. 16, the coaxial cable 40 is composed of an insulator 42, an outer conductor 43, and an insulating coating 44 with the central conductor 41 and the central conductor 41 interposed therebetween, from the center to the outer diameter. They are arranged in this order and have appropriate flexibility.

As shown in the enlarged view of the A portion in FIG. 17 at (a), the coaxial electrodes 20 provided on the bottom surface of the upper jaw portion 14*a* and the upper surface of the lower jaw portion 116*a* have the central conductor 21 and the semicircular insulator 22 having a semicircular cross section. It is composed of a semicircular tubular semicircular tube conductor 23 arranged outside the semicircular insulator 22.

As shown in FIG. 17 at (a), the coaxial electrode 20 configured in this way is semi-cylindrical and has a predetermined length, and as shown in FIG. 17 at (c), the bottom surface of the upper jaw portion 14*a*. And on the upper surface of the lower jaw portion 116*a*, the flat surfaces are arranged along the longitudinal direction so as to face each other. Although not shown, the coaxial electrode 20 arranged on the upper jaw portion 14*a* and the lower jaw portion 116*a* has an insulating layer arranged on the outside and is insulated from the upper jaw portion 14*a* and the lower jaw portion 116*a*.

Then, as shown in FIG. 17 at (b), the central conductor 21 of each coaxial electrode 20 provided in the upper jaw portion 14*a* and the lower jaw portion 116*a* is connected to the central conductor 41 of the coaxial cable 40, and the half of the coaxial electrode 20 is connected. The circular conductor 23 and the outer conductor 43 of the coaxial cable 40 are connected to form the same pole connection. If necessary, one of them may be connected in the opposite polarity as shown in FIG. 20.

In this way, the coaxial electrode 20 connected to the microwave transmitter 30 via the coaxial cable 40 may irradiate microwaves between the central conductor 21 of the coaxial electrode 20 and the semicircular conductor 23 via the coaxial cable 40 when the microwave generator 30 activates.

When microwaves are irradiated from the coaxial electrode 20 in a state where the blood vessel B, which is the target site, is gripped and seated by the gripping mechanism 17*a*, the blood vessel B gripped and seated by the gripping mechanism 17*a* is coagulated by the microwave. Then, in the blood vessel B, the portion solidified by the microwave irradiated from the coaxial electrode 20 may be cut by the cutter 15*a*. As a modification of this embodiment, FIG. 16 shows an embodiment in which the electronic module 31 is built in the end effector 10*a*.

Figure 25:
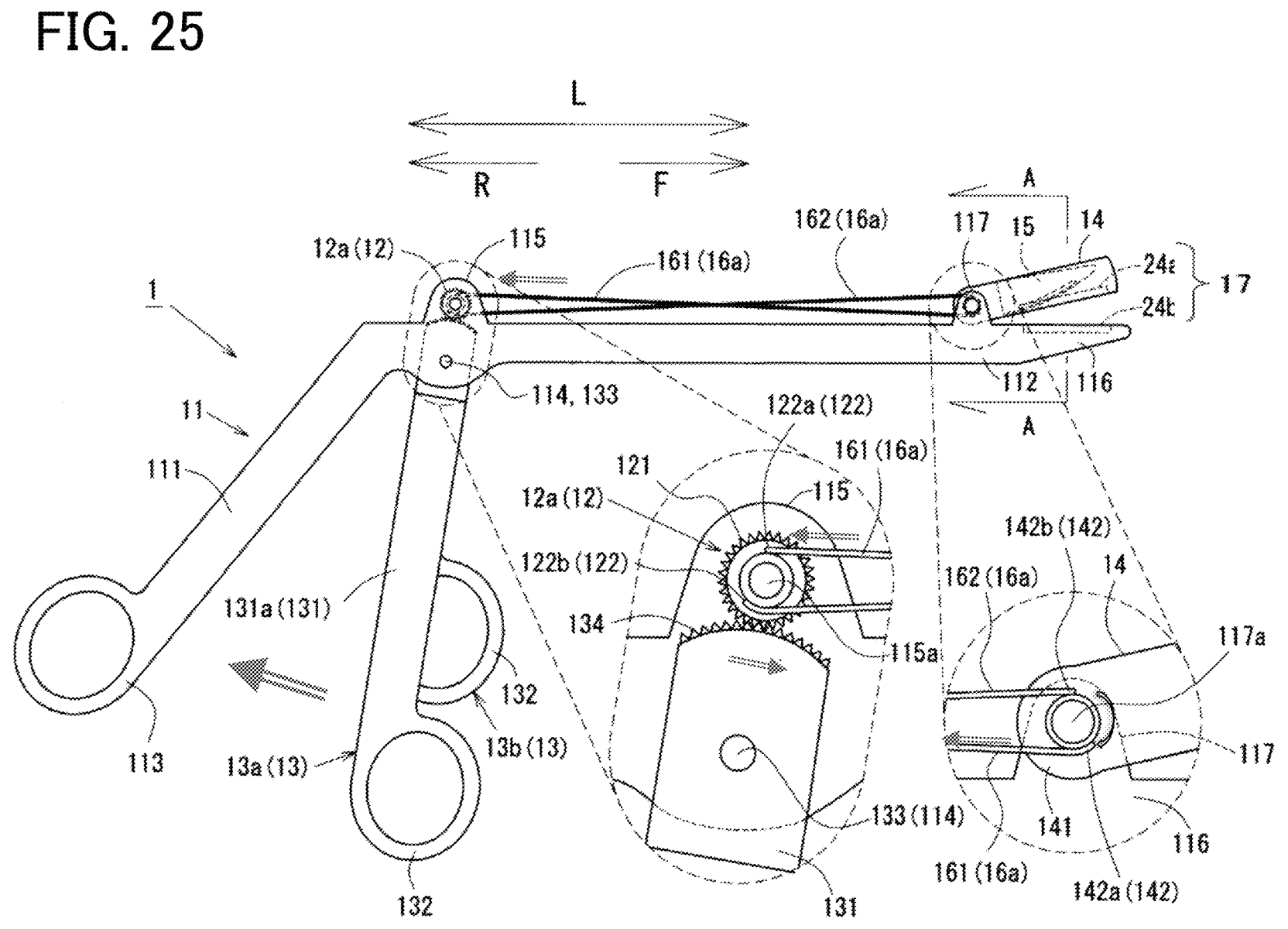
Figure 27:
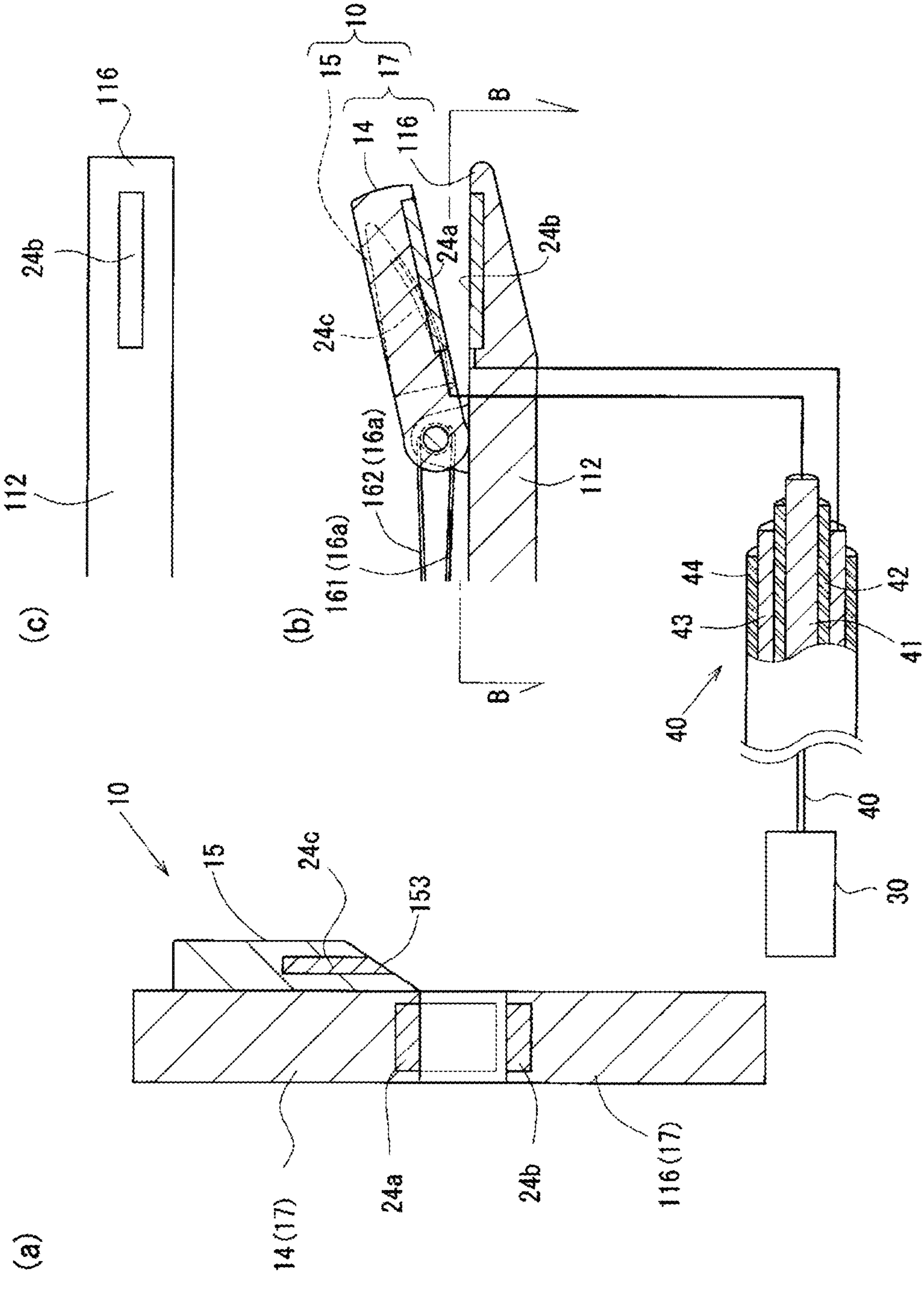
FIG. 27 is a schematic explanatory view of the forceps of FIG. 25.

The above-described microwave generator 30 is an example which is incorporated in the end effector 10*a*, but it may incorporate a microwave irradiation module 222 of FIG. 25, or incorporate appropriate electronic circuitry of the surgical device 221 shown in FIG. 27 (*b*). By providing the electronic module 31 in the end effector 10*a*, the medical device may be miniaturized and the convenience of surgery is enhanced.

Figure 18:
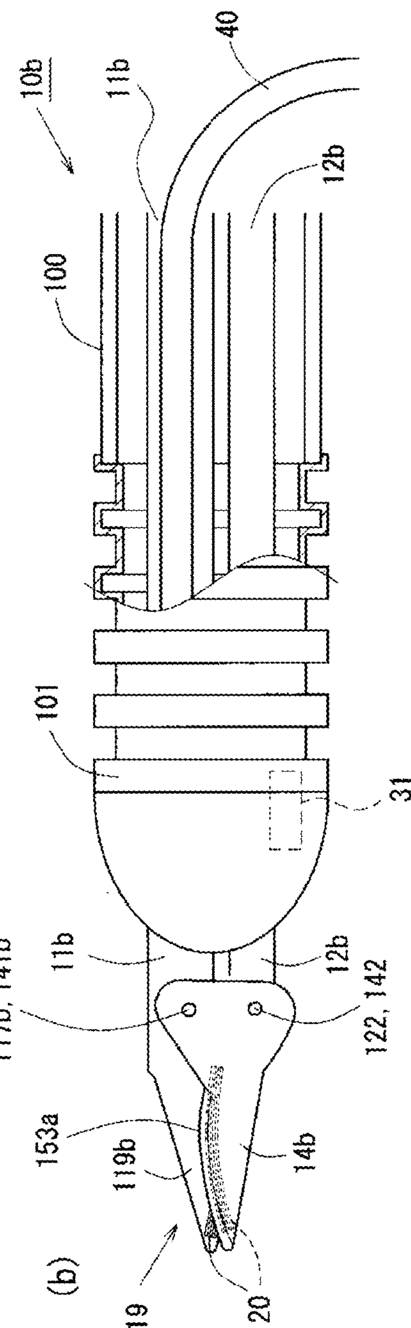
FIG. 18 is a schematic explanatory view of an end effector according to still another embodiment of the present invention.
Figure 19:
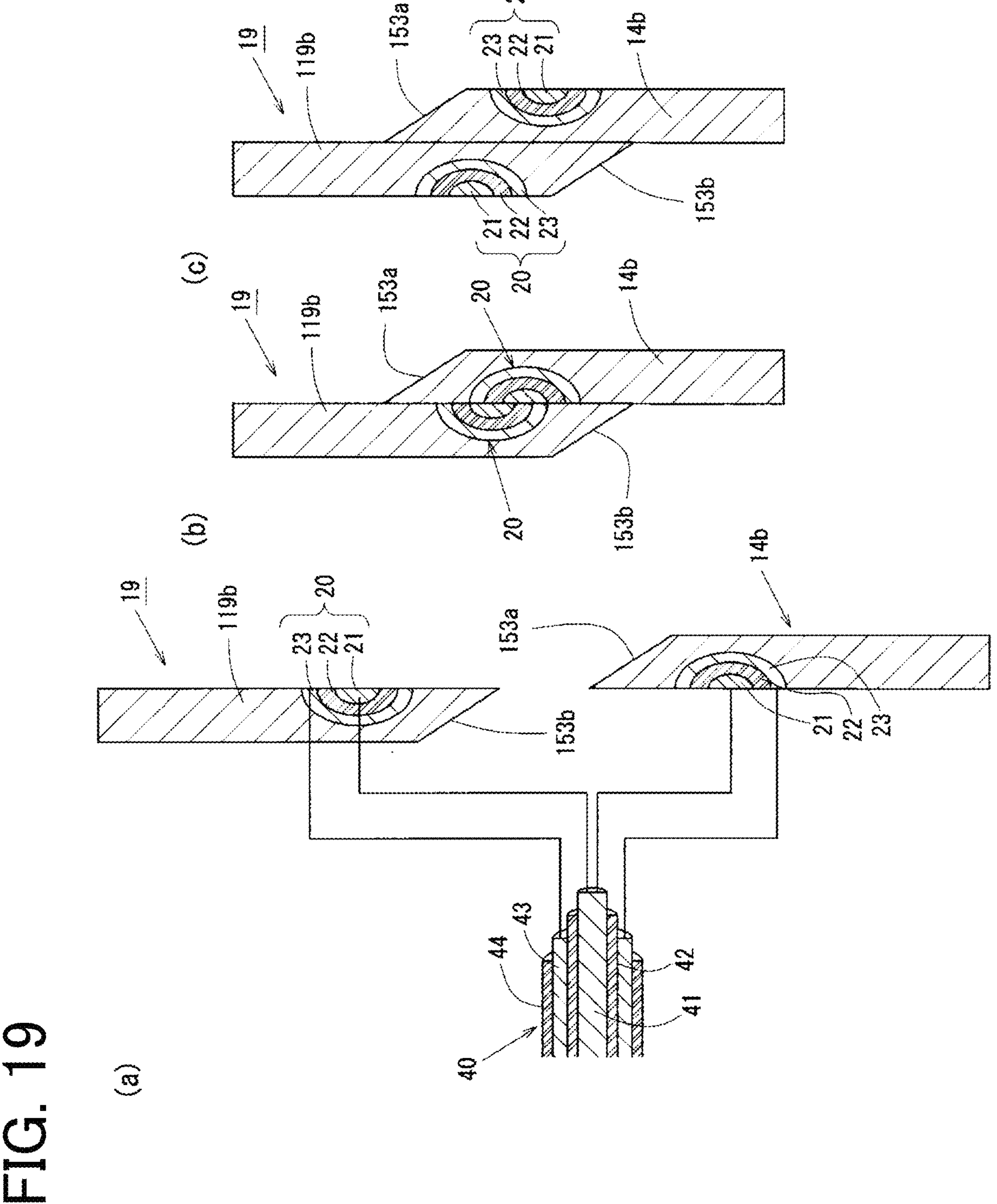
FIG. 19 is a schematic explanatory view of the end effector of FIG. 19 at (a) is a schematic cross-sectional view of a cutting mechanism in an end effector in a normal state, FIG. 19 at (b) is a schematic cross-sectional view of an end effector in a cut state, and FIG. 19 at (c) is schematic cross-sectional view of a cutting mechanism in which the arrangement of coaxial electrodes is different.

Subsequently, FIGS. 18 and 19 show the end effector 10*b* as another embodiment of the present invention.

FIG. 18 shows a schematic explanatory view of the end effector 10*b* of this embodiment. FIG. 18 at (a) shows a schematic front view of the end effector 10*b* in a normal state, and FIG. 18 at (b) shows a schematic front view of the end effector 10*b* in a cut state.

FIG. 19 shows a schematic explanatory view of the end effector 10*b*. FIG. 19 at (a) shows a schematic cross-sectional view of a cutting mechanism in the end effector 10*b* in a normal state, FIG. 19 at (b) shows a schematic cross-sectional view of the end effector 10*b* in a cut state, and FIG. 19 at (c) shows a coaxial electrode. A schematic cross-sectional view of a cutting mechanism with different arrangements is shown.

In FIG. 16, with respect to the end effector 10*a* in which the gripping mechanism 17*a* composed of the lower jaw portion 116*a* and the upper jaw portion 14*a* is further provided with a cutter 15*a*, and the target site gripped by the gripping mechanism 17*a* is cut by the cutter 15*a*, the end effector 10*b* of FIG. 18 is provided with a fixed blade 119*b* instead of the lower jaw portion 116*a* at the tip of the reference shaft 11*b*, and provided with a movable blade 14*b* instead of the upper jaw portion 14*a* to form a cutting mechanism 19.

In the end effector 10*b* configured in this way, the movable frame 12*b* is moved to the tip side F with respect to the reference shaft 11*b*, so that the movable blade 14*b* connected to the movable frame 12*b* supports the tip provided on the reference shaft 11*b*. It rotates around the shafted portion 141*b* pivotally supported by the shaft 117*b* in a direction close to the fixed blade 119*b*. Then, as shown in FIG. 18 at (b) and FIG. 19 at (b), the fixed blade 119*b* and the movable blade 14*b* are closed, and the target site may be cut by the cutting blades 153*b* and 153*a* provided respectively.

A coaxial electrode 20 is provided on the side surface of the end effector 10*b* configured as described above on the opposite side of the fixed blade 119*b* and the movable blade 14*b*. Then, as shown in FIG. 19 at (a), the central conductor 21 of each coaxial electrode 20 provided on the side surfaces of the fixed blade 119*b* and the movable blade 14*b* and the central conductor 41 of the coaxial cable 40 are electrically connected to be coaxial. The semi-circular conductor 23 of the electrode 20 and the outer conductor 43 of the coaxial cable 40 are electrically connected.

Therefore, in the cutting mechanism 19 of the end effector 10*b*, microwaves may be irradiated from the coaxial electrodes 20 provided on the side surfaces of the fixed blade 119*b* and the movable blade 14*b*.

In the end effector 10*b* configured in this way, microwaves are irradiated from each of the fixed blade 119*b* and the movable blade 14*b* in a state where the blood vessel B, which is the target site, is arranged between the fixed blade 119*b* and the movable blade 14*b*. As a result, the blood vessel B arranged between the fixed blade 119*b* and the movable blade 14*b* is coagulated and tied. Then, the coagulated portion in the blood vessel B may be cut by the cutting mechanism 19 by operating the movable blade 14*b*.

Although the blood vessel B may be efficiently coagulated and bound by abutting the blood vessel B on the movable blade 14*b* and the reference shaft 11*b* and irradiating the blood vessel B with microwaves from the coaxial electrode 20, the movable blade 14*b* and the fixed blade 119*b* and blood vessel B may be slightly separated.

Further, in the end effector 10*b*, as shown in FIG. 19 at (a) and (b), the coaxial electrodes 20 are provided on the opposite side surfaces of the fixed blade 119*b* and the movable blade 14*b*, but as shown in FIG. 19C. the coaxial electrode 20 may be arranged on the outer side surface which is the side separated from the fixed blade 119*b* and the movable blade 14*b*.

Further, in the end effector 10*b*, as described above, the central conductor 21 of the coaxial electrode 20 and the central conductor 41 of the coaxial cable 40 provided on the side surfaces of the fixed blade 119*b* and the movable blade 14*b* are electrically connected to each other. The semicircular conductor 23 of the coaxial electrode 20 and the outer conductor 43 of the coaxial cable 40 are electrically connected.

On the other hand, as shown in FIG. 20 at (a), one central conductor 21 of the coaxial electrode 20 provided on each of the side surfaces of the fixed blade 119*b* and the movable blade 14*b* and the outer conductor 43 of the coaxial cable 40 are electrically connected. It may be connected and the semicircular conductor 23 of the coaxial electrode 20 and the central conductor 41 of the coaxial cable 40 may be electrically connected. In this case, the polarities of the coaxial electrodes 20 provided on the side surfaces of the fixed blade 119*b* and the movable blade 14*b* are opposite to each other.

Also in this case, when the microwave transmitter 30 is operated, microwaves may be irradiated between the central conductor 21 and the semicircular conductor 23 at the coaxial electrodes 20 provided on the side surfaces of the fixed blade 119*b* and the movable blade 14*b*, respectively. At the same time, the central conductor 21 of one coaxial electrode 20 and the other central conductor 21 having opposite polarities, and the semicircular conductor 23 of one coaxial electrode 20 and the semicircular conductor 23 of the other coaxial electrode 20 Microwaves will be emitted even in the meantime.

Further, as shown in FIG. 20 at (b), the end effector 10*a* shown in FIG. 17 at (b) may be connected and configured to have coaxial electrodes 20 provided on the facing surfaces of the lower jaw portion 116*a* and the upper jaw portion 14*a* having opposite polarities.

Figure 24:
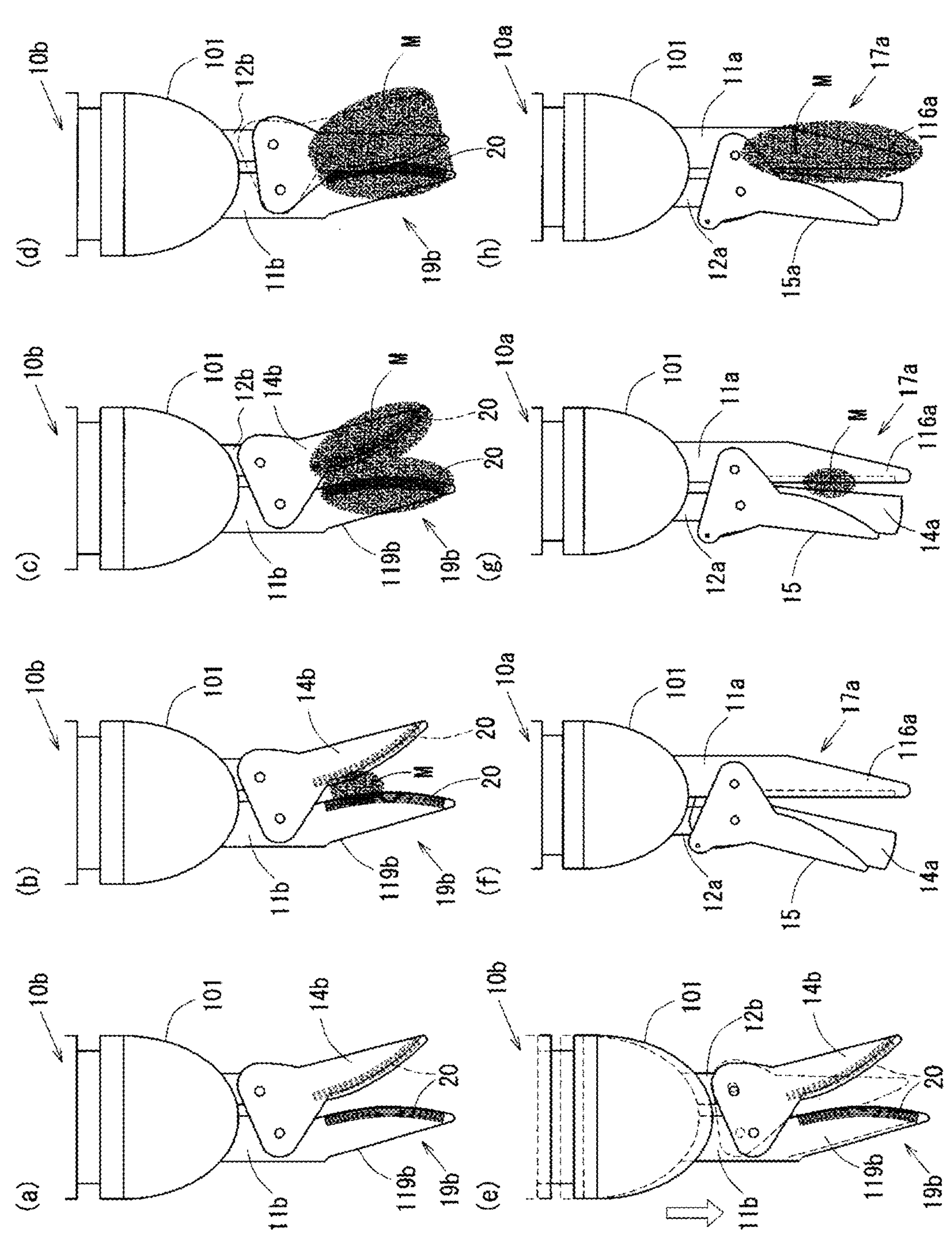
FIG. 24 is an explanatory diagram showing a schematic image of an experimental result by microwave irradiation from an electrode in an end effector.

Further, although not shown, in the end effector 10*a*, a coaxial electrode 20 may be provided on the side surface of the cutter 15*a* in addition to the facing surface between the lower jaw portion 116*a* and the upper jaw portion 14*a*, or the coaxial electrode 20 may be provided on the upper jaw portion 14*a*. The coaxial electrode 20 may be provided on the upper surface of the lower jaw portion 116*a* and the side surface of the cutter 15*a* without providing the 20. Further, as shown in FIG. 24 at (f) to (h), the coaxial electrode 20 may be provided only on one of the facing surfaces of the upper jaw portion 14*a* and the lower jaw portion 116*a*.

Figure 21:
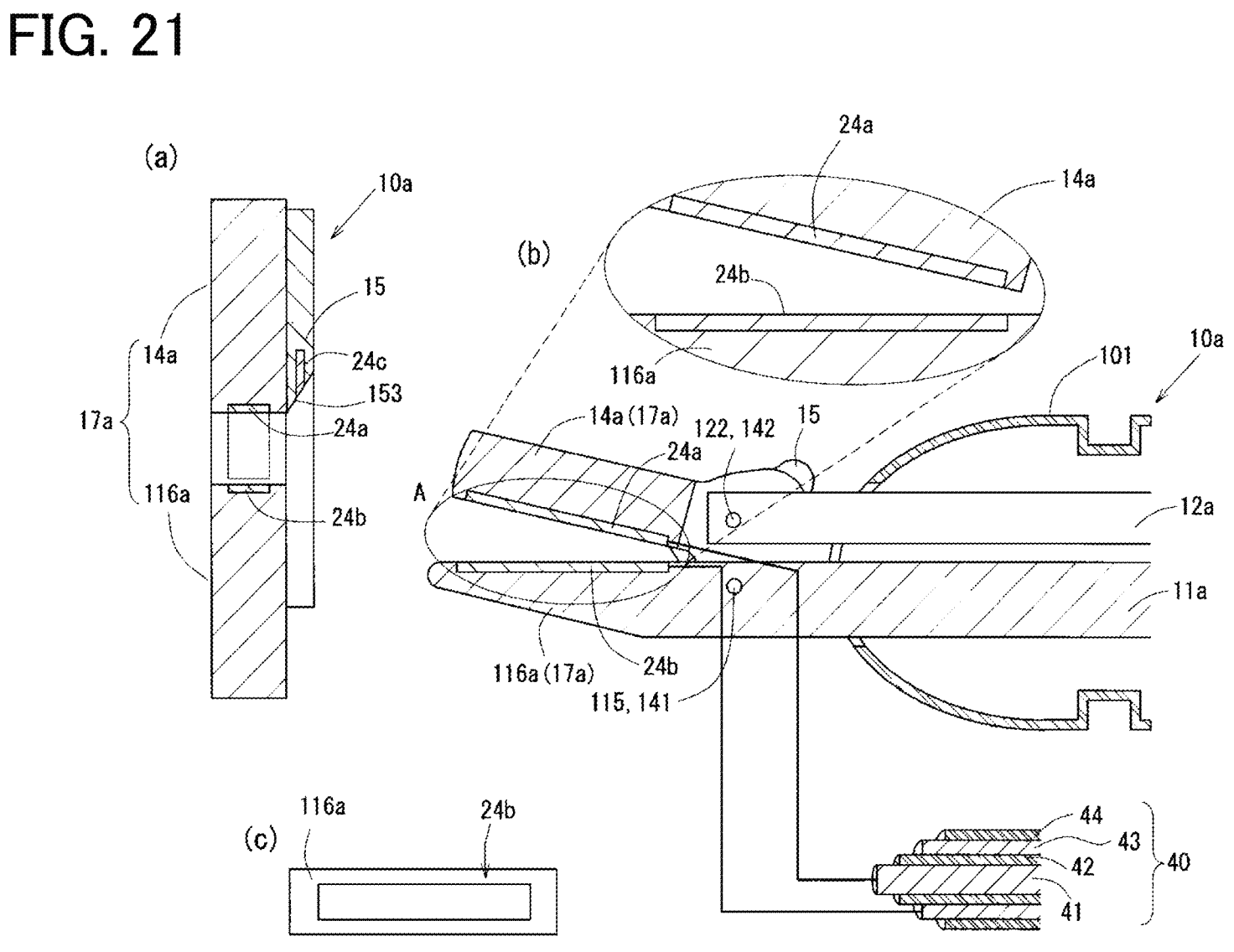

Further, as shown in FIG. 21, instead of the coaxial electrodes 20 provided on the upper jaw portion 14 and the lower jaw portion 116*a* of the end effector 10*a*, the above-mentioned irradiation electrodes 24*a* and 24*b* may be provided. Further, an irradiation electrode 24*c* may be provided on the side surface of the cutter 15. FIG. 21 at (a) shows a vertical cross-sectional view of the end effector 10*a* provided with the irradiation electrode 24 (24*a*, 24*b*, 24*c*), and FIG. 21 at (b) shows a partially enlarged vertical cross-sectional view of the end effector 10*a* provided with the irradiation electrode 24.

Figure 22:
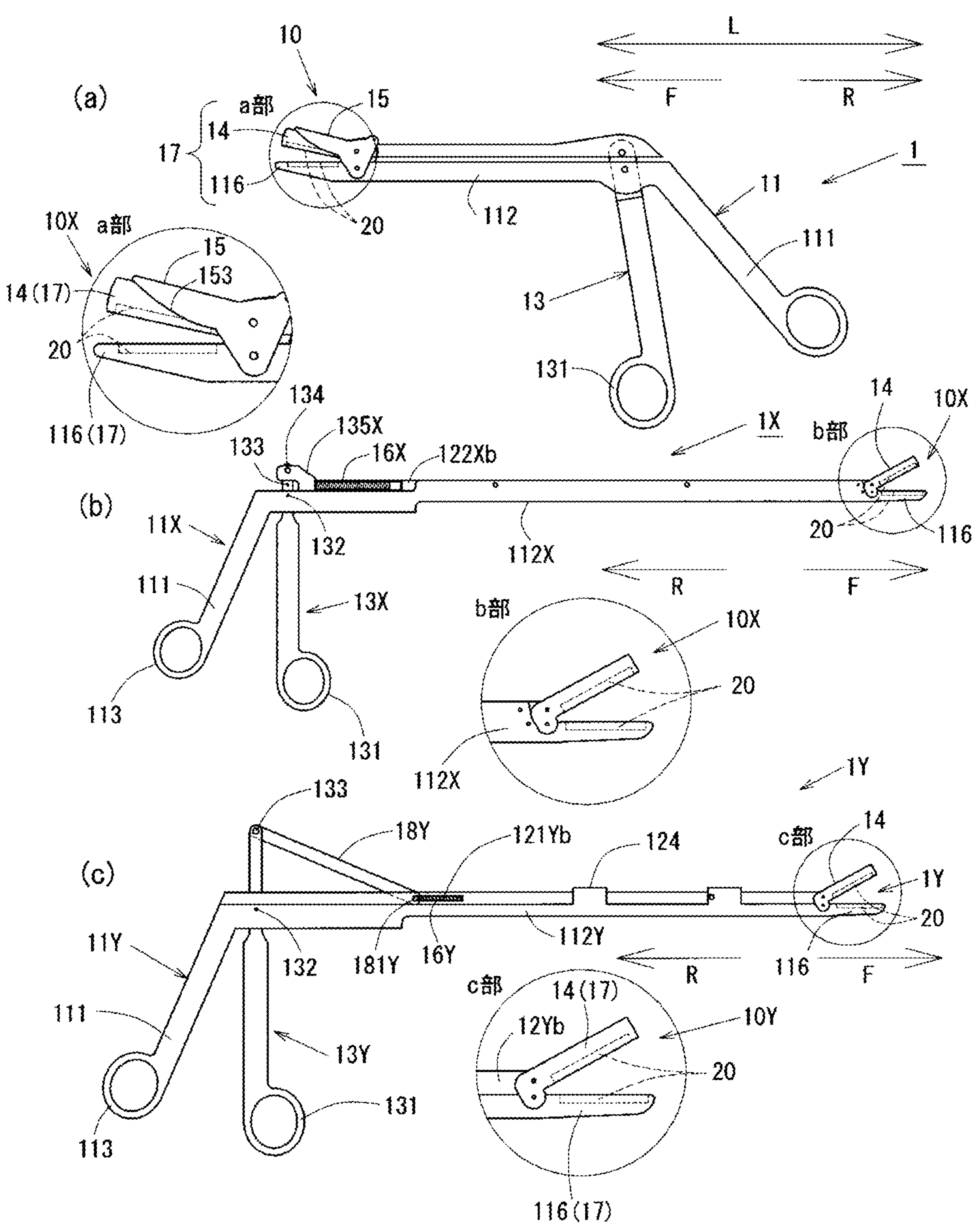
FIG. 22 is a schematic explanatory view of forceps of another embodiment.

Furthermore, as shown in FIG. 22, at least one of the upper jaw portion 14, the cutter 15 and the lower jaw portion 116 in the above-mentioned forceps 1, 1X, 1Y may be provided with a coaxial electrode 20 connected to the microwave generator 30 by a coaxial cable 40.

FIG. 22 at (a) shows a front view of the forceps 1 in which the coaxial electrodes 20 are provided on the upper jaw portion 14 and the lower jaw portion 116. FIG. 22 at (b) shows a front view of the forceps 1X having the coaxial electrodes 20 provided on the upper jaw portion 14 and the lower jaw portion 116, and FIG. 22 at (c) shows the forceps 1Y provided with the coaxial electrodes 20 on the upper jaw portion 14 and the lower jaw portion 116. The front view of is shown. As described above, the forceps 1, 1X and 1Y provided with the coaxial electrode 20 in the gripping mechanism 17 composed of the upper jaw portion 14 and the lower jaw portion 116 operate the trigger handle 13 with respect to the target site gripped by the gripping mechanism 17. After irradiating microwaves from both coaxial electrodes 20 to coagulate, the target site may be cut with the cutters 15 and 15Y.

In FIG. 22, both the upper jaw portion 14 and the lower jaw portion 116 constituting the gripping mechanism 17 are provided with the coaxial electrode 20, but one of the upper jaw portion 14 and the lower jaw portion 116 may be provided with the coaxial electrode 20. The cutters 15 and 15Y may be provided with the coaxial electrode 20.

Figure 23:
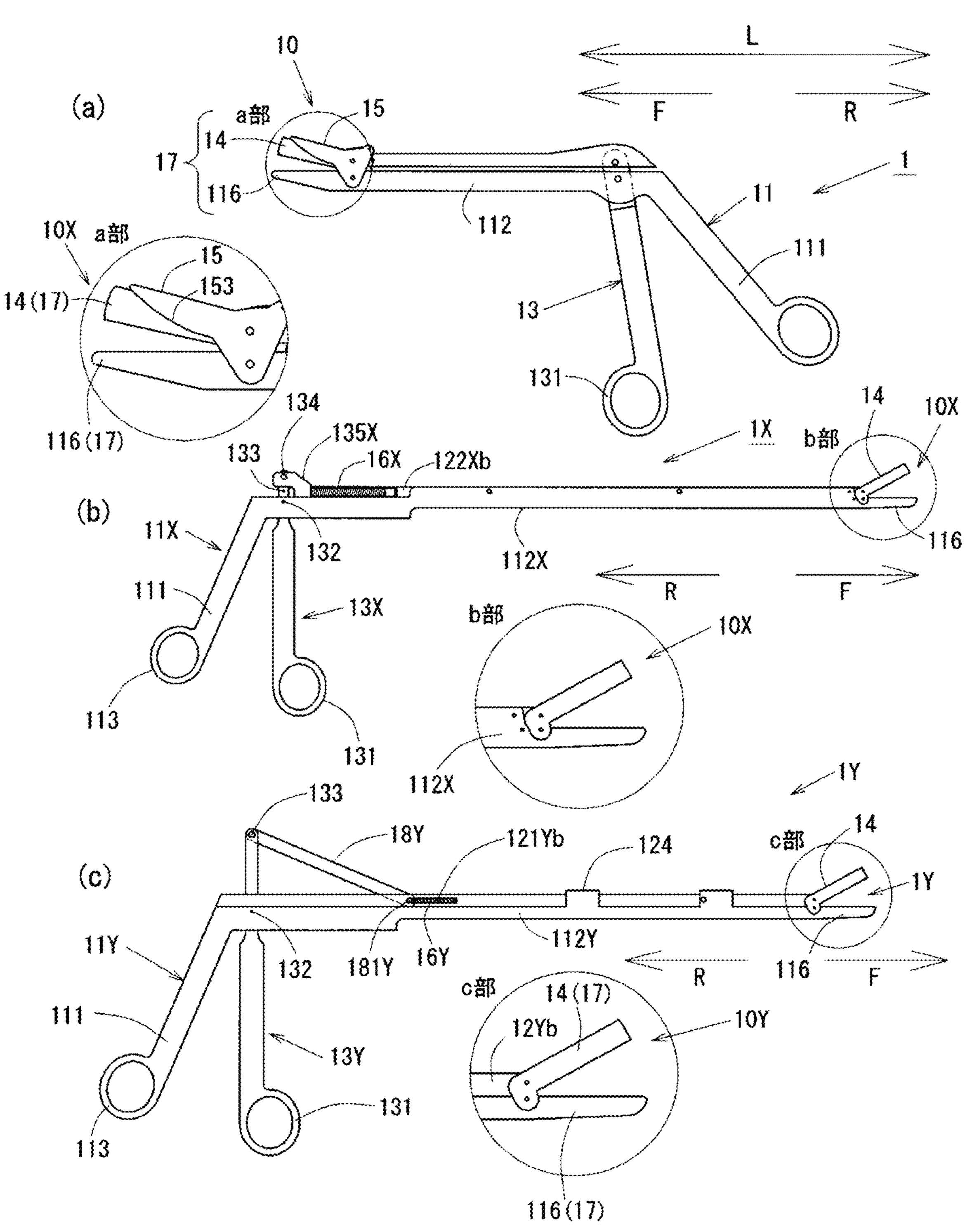
FIG. 23 is a schematic explanatory view of forceps of still another embodiment. 23 at (a) is a rear view of the forceps of FIG. 1 without electrodes, FIG. 23 at (b) is a front view of the forceps of FIG. 7 without electrodes, and FIG. 23 at (c) is a front view of forceps of FIG. 12 without electrodes.

Furthermore, as shown in FIG. 23, depending on the specifications as a cutting device, a coaxial electrode 20 and an irradiation electrode 24 do not have to be provided on the upper jaw portion 14, the cutting cutter 15 and the lower jaw portion 116 in the above-mentioned forceps 1, 1X, 1Y.

FIG. 23 at (a) shows a front view of the forceps 1 in which the upper jaw portion 14, the cutter 15, and the lower jaw portion 116 are not provided with the coaxial electrode 20 or the irradiation electrode 24. FIG. 23 at (b) shows a front view of the forceps 1X in which the upper jaw portion 14, the cutter 15, and the lower jaw portion 116 are not provided with the coaxial electrode 20 and the irradiation electrode 24, and FIG. 23 at (c) shows a front view of the forceps 1Y in which the coaxial electrode 20 and the irradiation electrode 24 are not provided on the upper jaw portion 14, the cutter 15, and the lower jaw portion 116.

FIG. 24 is a schematic diagram of a confirmation test in which solidification due to microwaves irradiated from the coaxial electrode 20 is confirmed. Specifically, FIG. 24 at (a) to (e) shows the test situation in which microwaves were irradiated from the coaxial electrodes 20 provided on the fixed blade 119*b* and the movable blade 14*b* of the end effector 10*b* in the egg white and the coagulated egg white M is cut. FIG. 24 at (f) to (h) shows the test conditions in the case where the coaxial electrode 20 is provided only on the lower jaw portion 116*a* of the end effector 10*a*, that is, the coaxial electrode 20 is provided on the so-called single-edged blade.

FIG. 24 is a schematic diagram of a confirmation test in which solidification due to microwaves irradiated from the coaxial electrode 20 is confirmed. Specifically, FIG. 24 (*a*) to (*e*) shows a test condition in the case where the coaxial electrode 20 is provided only on the lower jaw portion 116*a* of the end effector 10*a*, that is, the coaxial electrode 20 is provided on the so-called single-edged blade. FIG. 24 (*f*) to (*h*) shows at test condition in the case where the coaxial electrode 20 is provided only on the lower jaw portion 116*a* of the end effector 10*a*, that is, the coaxial electrode 20 is provided on the so-called single-edged blade.

As shown in FIG. 24 at (a), an end effector 10*b* having a coaxial electrode 20 on both blades is disposed in egg white, a microwave irradiation from the coaxial electrode 20 is provided on both blades by activating microwave generator 30. Then, as shown in FIG. 24 at (b), coagulation starts from the base side where the distance between the coaxial electrodes 20 is narrow between the fixed blade 119*b* and the movable blade 14*b* constituting the cutting mechanism 19, and the coagulated egg white M is formed.

When microwave irradiation from the coaxial electrodes 20 provided on both blades is continued, as shown in FIG. 24 at (c), the coagulated egg white M expands along the coaxial electrodes 20 provided on the fixed blade 119*b* and the movable blade 14*b*. Then, when the movable blade 14*b* is rotated with respect to the fixed blade 119*b* constituting the cutting mechanism 19, the coagulated egg white M may be cut by the cutting blade provided on the fixed blade 119*b* and the movable blade 14*b* as shown in FIG. 24 at (d).

When cutting the coagulated egg white M with the cutting blade, the coagulated egg white M may be cut while irradiating the microwave from the coaxial electrode 20 provided on the fixed blade 119*b* and the movable blade 14*b*, or the coaxial electrode 20 does not irradiate the microwave.

Then, as shown in FIG. 24 at (e), the movable blade 14*b* constituting the cutting mechanism 19 is opened, the coagulated egg white M is advanced in the direction of the arrow with respect to the cut portion, and the microwave is irradiated again from the coaxial electrode 20. As shown in FIG. 24 at (b), coagulated egg white M is formed. By repeating this, it was confirmed that the cutting mechanism 19 in the end effector 10*b* may cut, for example, the coagulated portion in the blood vessel B. It is presumed that this result will be an operation to strengthen the coagulation function and suppress the deterioration of the hemostatic function in the blood clot due to bleeding.

When the coaxial electrode 20 is provided on both the lower jaw portion 116*a* and the upper jaw portion 14*a* of the end effector 10*a*, or when the coaxial electrode 20 is provided on the lower jaw portion 116*a* and the cutting cutter 15*a*, or further when the coaxial electrode 20 is provided in all of the lower jaw portion 116*a*, the upper jaw portion 14*a*, and the cutting cutter 15*a*, similar to the end effector 10*b* provided with the coaxial electrode 20 on both blades described above, the cutting mechanism 19 in the end effector 10*a* may cut, for example, the coagulated portion of the blood vessel B.

On the other hand, in the case of the end effector 10*a*, which is a single-edged electrode in which the coaxial electrode 20 is provided only on one of the lower jaw portion 116*a* and the upper jaw portion 14*a* constituting the cutting mechanism 19, the end effector 10*a* is as shown in FIG. 24 at (g). The coagulated egg white M is formed by irradiating the coaxial electrode 20 provided on the single-edged blade with microwaves, and the coagulated egg white M enlarged along the coaxial electrode 20 provided on the single-edged blade may be cut by the cutter 15*a*. However, as shown in FIG. 24 at (c), the formation rate of the coagulated egg white M is slower and the size of the coagulated egg white M formed is smaller than that in the case where the coaxial electrode 20 is provided on both blades.

Surgical equipment such as end effectors 10*a* and end effectors 10*b* that irradiate microwaves emit less smoke and mist, have a strong hemostatic function, and are useful for surgical support in closed spaces such as endoscopic surgery and robotic surgery. Optimal. However, when there is a lot of bleeding, hemostasis in the blood pool and hemostasis in the liquid are diminished like other energy devices, so that it is resolved by irradiating both blades with microwaves.

In the above-mentioned effect confirmation test, although not shown, the center conductor 21 of the coaxial electrode 20 and one of the semicircular conductors 23 are arranged on one of the double-edged blades to form an electrode, and the other of the double-edged blades is the center of the coaxial electrode 20. In the case of an end effector in which the other conductor of the conductor 21 and the semicircular conductor 23 is arranged and used as an electrode, the microwave is emitted from one electrode of the double-edged blade toward the electrode provided on the other, so that the end effector opens in the air. Although coagulation starts from the middle part of the tissue sandwiched between the blades, coagulation proceeds only to the electrode part on the side irradiated with microwaves in the egg white, and the rate of coagulation of the surrounding egg white at the other electrode is considerably delayed. It has been also confirmed that the blood-stopping power is weakened.

On the other hand, as described above, when the coaxial electrodes 20 provided on each of the double-edged blades of the end effector 10*b* irradiate microwaves, solidification proceeds from the coaxial electrodes 20 provided on the double-edged blades (see FIG. 24 at (b) and (c)), The egg white coagulated and the coagulated egg white M could be formed after twice the time in the air. Further, in the case of the end effector 10*a* having the coaxial electrode 20 on only one of the two blades, the coagulated egg white M was formed, but the formation of the coagulated egg white M on the entire surface was not completed even after taking three times as long. As described above, the arrangement of the coaxial electrode 20 that affects the formation of the coagulated egg white M may be selected according to the usage environment and the treatment target.

For example, FIG. 25 shows a front view of the open forceps 1 according to an embodiment of the present invention.

Figure 26:
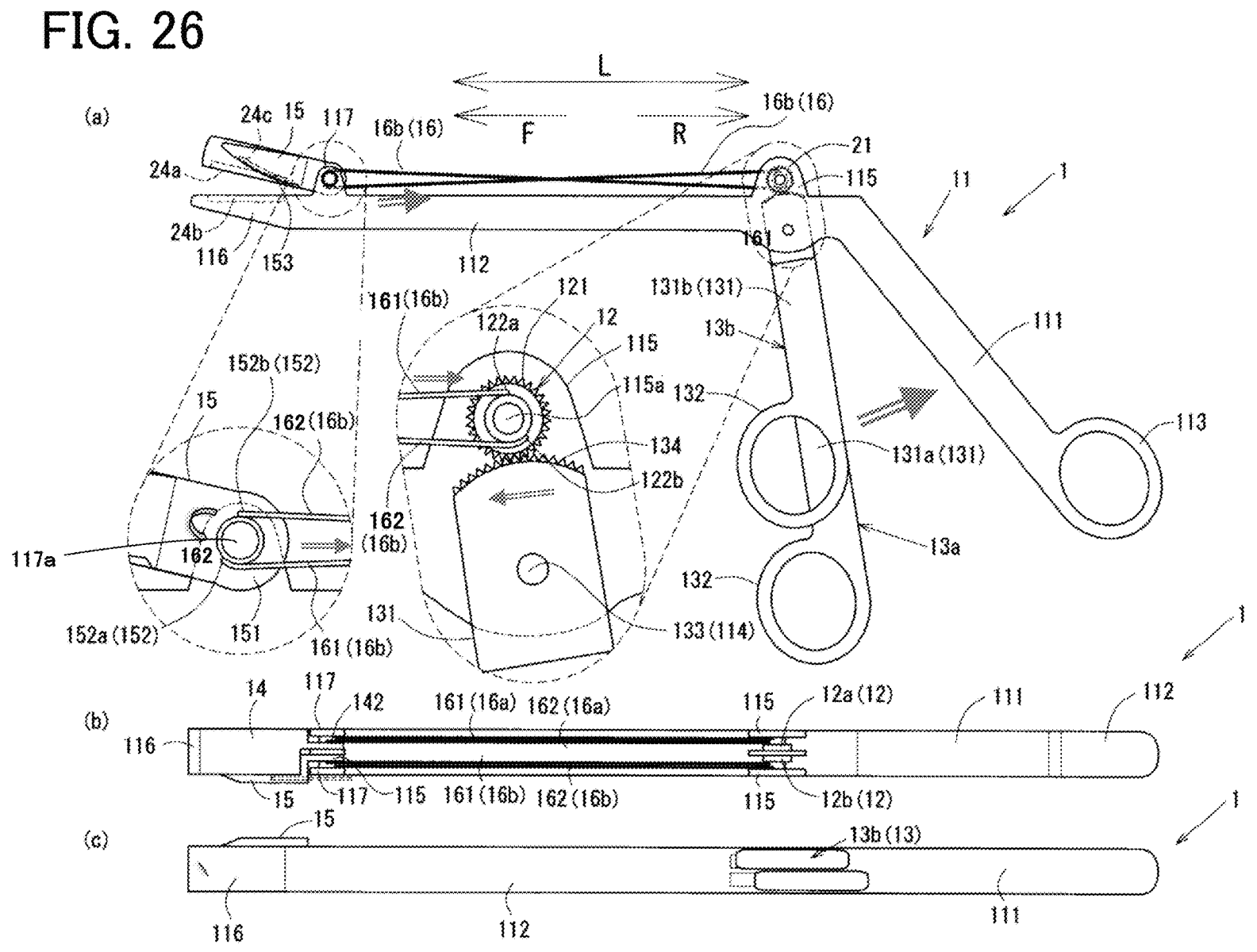

FIG. 26 shows an explanatory view of the forceps 1 in the open state of this embodiment. Specifically, FIG. 26 at (a) shows a rear view of the forceps 1. FIG. 26 at (b) shows a plane view of the forceps 1, and FIG. 26 at (c) shows a bottom view of the forceps 1 of FIG. 26 at (b).

FIG. 27 shows a schematic explanatory view of the forceps 1 of FIG. 25. Specifically, FIG. 27 at (a) shows a side sectional view taken along the line A-A in FIG. 27 at (c) is a diagram. An enlarged view of the electrode part of the B-B arrow view in FIG. 27 at (b) is shown.

Figure 28:
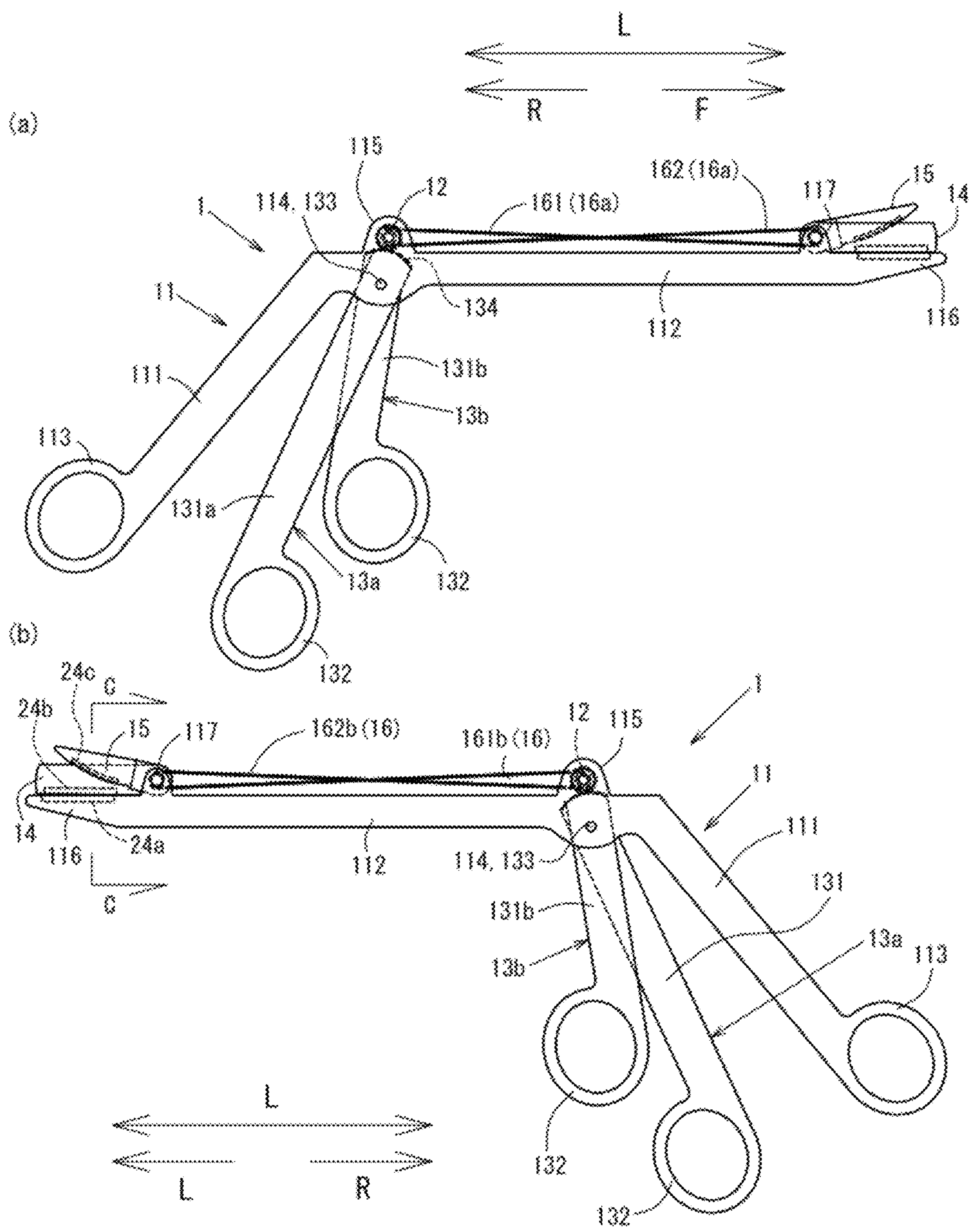
FIG. 28 is an explanatory view of a gripped state of the forceps of FIG. 25.

FIG. 28 shows an explanatory diagram of the gripped state of the forceps 1 of FIG. 25. Specifically, FIG. 28 at (a) shows a front view of the forceps 1 in a gripped state with the gripping mechanism 17 closed, and FIG. 28 at (b) shows a rear view of the forceps 1 in the same state.

Figure 29:
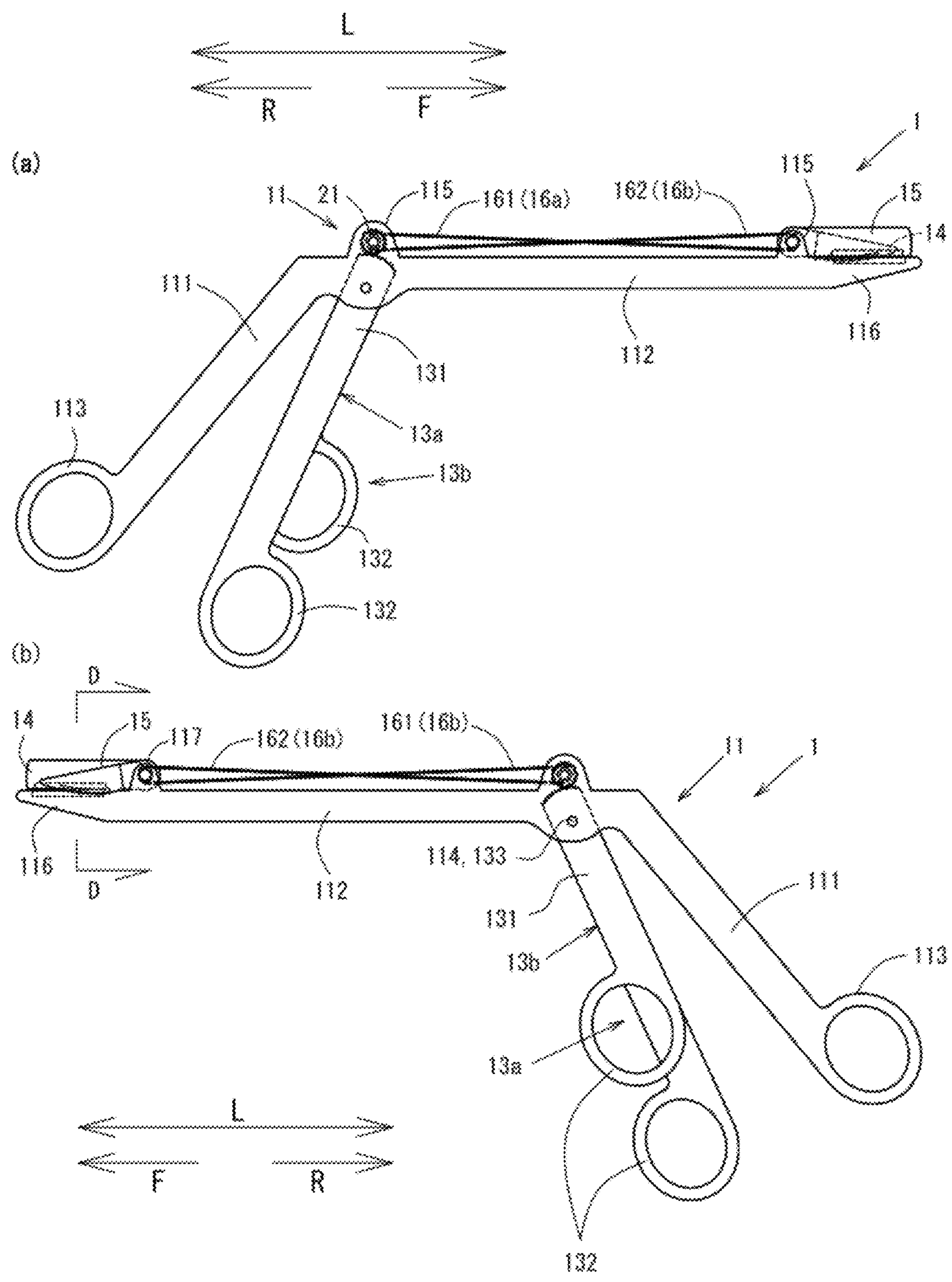
FIG. 29 is an explanatory view of a cut state of the forceps of FIG. 25.

FIG. 29 shows an explanatory diagram of the cut state of the forceps 1 of FIG. 25. Specifically, FIG. 29 at (a) shows a front view of the cutter 15 of the cutting mechanism 10 in the forceps 1 in a closed state, and FIG. 29 at (b) shows a rear view of the forceps 1 in the same state.

Figure 30:
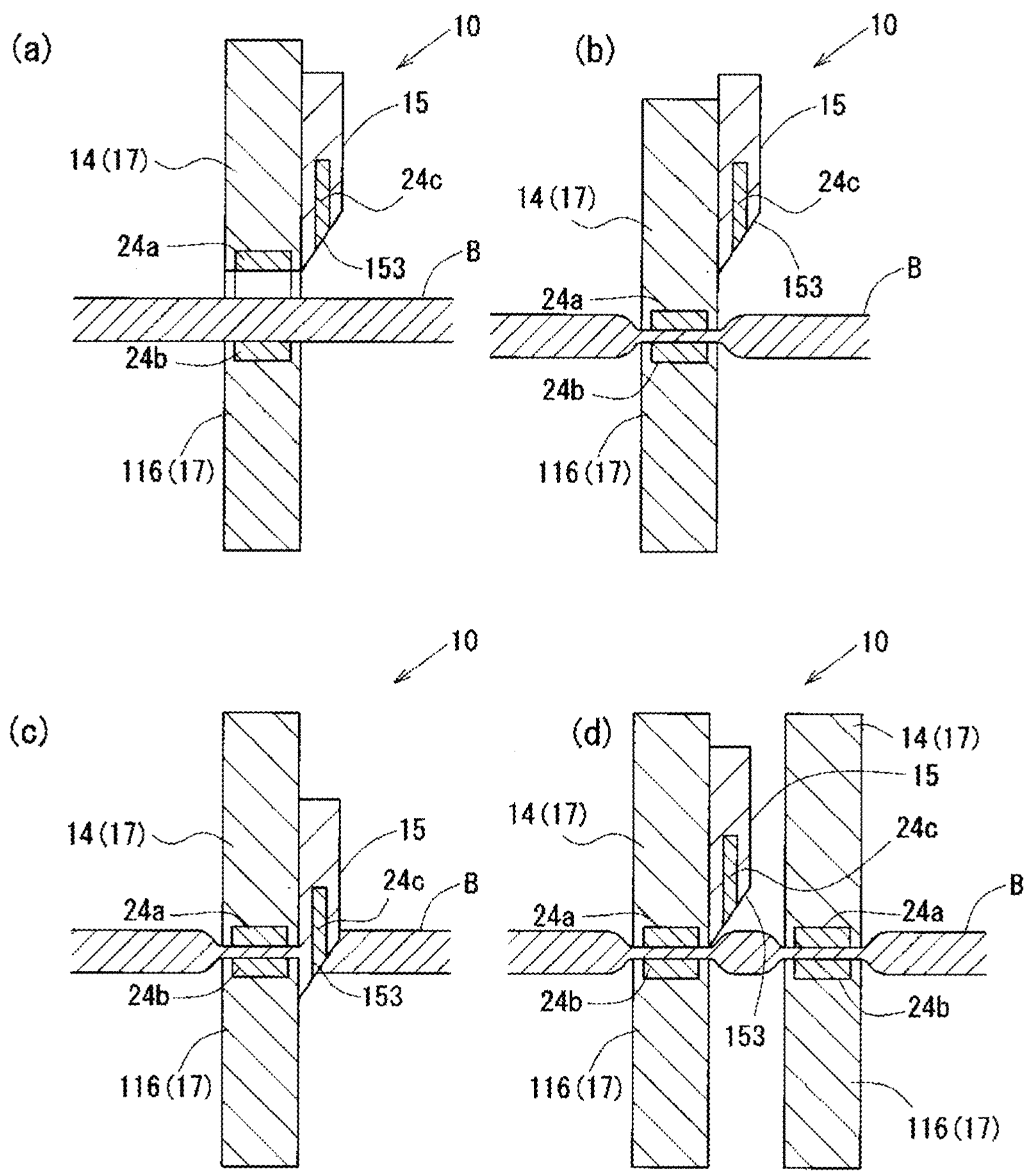
FIG. 30 is an explanatory view of a gripping state and a cutting state of the cutting mechanism in forceps.

FIG. 30 shows an explanatory diagram of the gripping state of the gripping mechanism 17 and the cutting state of the cutting mechanism 10 in the forceps 1. Specifically, FIG. 30 at (a) shows a side sectional view taken along the line A-A in FIG. 25 before gripping by the gripping mechanism 17, and FIG. 30 at (b) shows a state in which the target site is gripped by the gripping mechanism 17. A side sectional view taken along the line C-C in 28 at (b) is shown. Further, FIG. 30 at (c) shows a side sectional view taken along the line D-D in FIG. 29 at (b) in a state where the target site is cut by the cutter 15, and FIG. 30 at (d) shows a schematic right side view of a state in which the cutting mechanism 10 is gripped by the gripping mechanism 17 of another aspect of the cutting mechanism 10.

In FIGS. 25 to 30, the forceps 1 includes a main body frame 11, a pinion gear 12, a trigger handle 13 (13*a* and 13*b*), a upper jaw portion 14, a cutter 15, and an opening/closing wire 16 (16*a* and 16*b*).

The direction along the longitudinal direction of the main body frame 11 of the forceps 1 is the longitudinal direction L, the side of the main body frame 11 where the upper jaw portion 14 and the cutter 15 are arranged is the tip side F, and the side where the trigger handle 13 is arranged is the side. The base end side R is used.

Returning to FIG. 25, the main body frame 11 is roughly composed of two sides that intersect in an obtuse angle, and one of the two sides is a fixed handle frame 111 that functions as an operation member together with the trigger handle 13, and the other is a reference frame 112. There is. The main body frame 11 configured in this way may be made of a metal such as stainless steel.

At the end of the fixed handle frame 111, a ring portion 113 for inserting a user's finger for operating the forceps 1 is provided.

Further, in the vicinity of the base portion of the reference frame 112, a support shaft 114 that pivotally supports the trigger handle 13 described later is provided, and a gear support portion 115 that pivotally supports the pinion gear 12 described later is provided above the support shaft 114.

Further, a lower jaw portion 116 constituting the mechanism 17 is provided the end portion of the distal end side F of the reference frame 112, in cooperation with the at gripping trigger handle 13*a* of the trigger handle 13, grip the target site, such as the treatment target vessel B (see FIG. 30). The lower jaw portion 116 is configured to have a tapered shape toward the tip end side F in front view. The lower jaw portion 116 is also referred to as "mandibular".

Further, on the base end side R of the lower jaw portion 116 of the reference frame 112, a support shaft 117*a* is provided on the tip support portion 117 that rotatably supports the upper jaw portion 14 and the cutter 15.

The pinion gear 12, which functions as a gripping member rotating (moving) mechanism and a cutting member rotating (moving) mechanism in cooperation with the opening/closing wire 16 described later, is pivotally supported by the above-mentioned gear support portion 115 and is supported by the trigger handle 13. The operation is converted into the movement of the opening/closing wire 16. Specifically, the upper jaw gear 12*a* (FIG. 25) that converts the operation of the gripping trigger handle 13*a* into the movement of the upper jaw wire 16*a*, and the cutter that converts the operation of the cutting trigger handle 13*b* into the movement of the cutter wire 16*b*. There is a gear 12*b* (FIG. 26), the upper jaw gear 12*a* is arranged on the front side, and the cutter gear 12*b* is arranged on the back side.

The upper jaw gear 12*a* and the cutter gear 12*b* have the same configuration, and have gear teeth 121 that mesh with the rack gear 134 of the trigger handle 13 described later on the outer peripheral surface of the gripping trigger handle 13*a*, and the base of the opening/closing wire 16 described later. A wire attachment portion 122 to which an end is attached is provided.

Specifically, as shown in FIG. 25, the near-side mounting is arranged at the axis center 115*a* of the gear support portion 115, and the tip of the near-side wire 161 (16*a*) close to the reference frame 112 is attached to the tip support portion 117. There is a portion 122*a* and an open side mounting portion 122*b* that is arranged below the shaft center 115*a* and to which the tip of the open side wire 162 is mounted. The wire mounting portion 122 is arranged at a predetermined distance in the radial direction with respect to the axis center 115*a* of the gear support portion 115.

Further, as shown in FIG. 26, around the axis center 115*a* of the gear support portion 115, there are disposed a proximity side attachment portion 152*a* to which the tip of the proximity side wire 161 of the cutter wire 16*b* is attached, and an open side mounting portion 152*b* to which the tip of the open side wire 162 of the cutter wire 16*b* is mounted. The wire mounting portion 152 is arranged at a predetermined distance in the radial direction with respect to the axis center 115*a* of the gear support portion 115.

The trigger handle 13 (13*a* and 13*b*) is an operation member operating the opening/closing wire 16 described later to rotate the upper jaw portion 14 and the cutter 15. There are provided a gripping trigger handle 13*a* for rotating the upper jaw portion 14 and a cutting trigger handle 13*b* that rotates the cutter 15.

The trigger handle 13 is provided with a ring portion 132 for inserting a user's finger into the lower end of the handle body 131 extending downward, and axis unit 133 pivotally supported by a support shaft 114 of the main body frame 11 in the vicinity of the upper end of the handle body 131.

Further, at the upper end of the handle body 131, rack gears 134 arranged in an upwardly convex circular hole shape are formed. The rack gear 134 is configured to mesh with the gear teeth 121 of the pinion gear 12.

The gripping trigger handle 13*a* and the cutting trigger handle 13*b* are similarly configured as described above, except that the length of the handle body 131 is different. Specifically, the handle body 131*a* of the gripping trigger handle 13*a* is the handle of the cutting trigger handle 13*b* so that the ring portion 132 of the cutting trigger handle 13*b* is arranged above the ring portion 132 of the gripping trigger handle 13*a*. The handle body 131*a* of the gripping trigger handle 13*a* is formed longer than the main body 131*b*.

The upper jaw portion 14 has a proximal end side R pivotally supported on the tip support portion 117 of the main body frame 11 (indicated by a broken line for convenience in the partially enlarged views of FIGS. 25 and 26), and the lower jaw of the main body frame 11 is supported. The gripping mechanism 17 is configured together with the portion 116. The upper jaw portion 14 maybe also referred to as maxilla.

The base end portion (left side in FIG. 25) of the upper jaw portion 14 is provided with a shafted portion 141 rotatably supported by a support shaft 117*a* of the tip support portion 117 of the main body frame 11.

The shaft-mounted portion 141 is provided with a pair of wire mounting portions 142 (142*a*, 142*b*) on the outer periphery of a tubular protruding column protruding outward from the shaft-mounted portion 141 to which the tip of the opening/closing wire 16 described later is attached. Specifically, the proximity-side mounting portion 142*a*, which is arranged below the shaft-mounted portion 141 (lower part of the wire mounting portion 142) and to which the tip of the proximity-side wire 161 of the upper jaw wire 16*a* is attached, and above the shaft-mounted portion 141. There is an open side mounting portion 142*b* that is arranged (upper part of the wire mounting portion 142) and to which the tip of the open side wire 162 of the upper jaw wire 16*a* is mounted. The wire mounting portion 142 is arranged at a predetermined distance in the radial direction with respect to the center of the support shaft 117*a* of the tip support portion 117 pivotally supported by the shaft-mounted portion 141.

As shown in FIG. 26, the cutter 15 is disposed on the back side of the upper jaw portion 14 (FIG. 25), The shaft portion 151 is rotatably supported the support shaft 117*a* of the tip support portion 117 of the main frame 11.

The shaft-mounted portion 151 is provided with a pair of wire mounting portions 152 (152*a* and 152*b*) on the outer periphery of a tubular protruding outward from the shaft-mounted portion 151 to which the tip of the opening/closing wire 16 described later is attached. Specifically, the proximity-side mounting portion 152*a*, which is arranged below the shaft-mounted portion 151 (lower part of the wire mounting portion 152) and to which the tip of the proximity-side wire 161 of the cutter wire 16*b* is attached, and above the shaft-mounted portion 151. There is an open side mounting portion 152*b* that is arranged (upper part of the wire mounting portion 152) and to which the tip of the open side wire 162 of the cutter wire 16*b* is mounted. The wire mounting portion 152 is arranged at a predetermined distance in the radial direction with respect to the center of the support shaft 117*a* of the tip support portion 117 pivotally supported by the shafted portion 151.

Further, in the present embodiment, the shafted portions 141 and 151 are not provided with the protrusion columns, but the shafted portions 141 are provided with holes for passing the support shaft 117*a*, and the shafted portions 141 and 151 are provided with holes around the holes, respectively. A structure may be provided in which wire mounting portions 142*a*, 142*b*, 152*a*, and 152*b* are provided.

In the cutter 15 configured as described above, a cutting blade 153 is formed along the lower end portion. Further, the cutter 15 has a plate shape and is configured to rotate along the side surface of the upper jaw portion 14 with the support shaft 117*a* as the axis.

The opening/closing wire 16 that functions as a gripping member rotating (moving) mechanism and a cutting member rotating (moving) mechanism in cooperation with the above-mentioned pinion gear 12 has a predetermined strength on which a pulling force may act and is flexible. There are an upper jaw wire 16*a* that rotates the upper jaw portion 14 and a cutter wire 16*b* that rotates the cutter 15. As shown in FIG. 26B, the upper jaw wire 16*a* that rotates the upper jaw portion 14 is arranged on the front side, and the cutter wire 16*b* that rotates the cutter 15 is arranged on the back side.

The opening/closing wire 16 has a predetermined strength on which a pulling force may act, and may be plate-shaped or strip-shaped as long as it has flexibility.

The opening/closing wire 16 (16*a* and 16*b*) includes a proximity side wire 161 that rotates the upper jaw portion 14 and the cutter 15 in a proximity direction to grip or cut, and an opening side wire 162 that rotates to the opening side. That is, the opening/closing wire 16 includes a proximity side wire 161 and an open side wire 162 as a upper jaw wire 16*a*, and a proximity side wire 161 and an open side wire 162 as a cutter wire 16*b*, and includes a total of four wires. The opening/closing wire 16 is hung in a state where tension is applied between the upper jaw portion 14 or the cutter 15 and the pinion gear 12.

Specifically, the proximity side wire 161 of the upper jaw wire 16*a* is arranged so that the wire attachment portion 122*a* of the pinion gear 12 and the proximity side attachment portion 142*a* of the upper jaw portion 14 are inclined downward toward the tip end side F. The open side wire 162 of the upper jaw wire 16*a* is arranged so that the wire attachment portion 122*b* of the pinion gear 12 and the open side attachment portion 142*b* of the upper jaw portion 14 are inclined upward toward the tip end side F. Therefore, when viewed from the front side, the proximity side wire 161 and the open side wire 162 of the upper jaw wire 16*a* intersect near the center of the longitudinal direction L in the reference frame 112.

Further, the proximity side wire 161 of the cutter wire 16*b* is also arranged so that the wire attachment portion 122*a* of the pinion gear 12 and the proximity side attachment portion 152*a* of the cutter 15 are inclined downward toward the tip side F, and the cutter is arranged. The open side wire 162 of the wire 16*b* is also arranged so that the wire attachment portion 122*b* of the pinion gear 12 and the open side attachment portion 152*b* of the cutter 15 are inclined upward toward the tip end side F. Therefore, when viewed from the front side, the proximity side wire 161 and the open side wire 162 of the cutter wire 16*b* intersect near the center of the longitudinal direction L in the reference frame 112.

In the forceps 1 configured in this way, the lower jaw portion 116 provided at the end of the tip end side F of the main body frame 11 and the upper jaw portion 14 whose base is pivotally supported by the tip support portion 117 with respect to the main body frame 11 constitute a gripping mechanism 17 that grips the target site.

Further, the cutter 15 that rotates and cuts the target site gripped by the gripping mechanism 17 along the side surface of the upper jaw portion 14 constitutes the cutting mechanism 10 together with the lower jaw portion 116.

The forceps 1 is provided with irradiation electrodes 24 (24*a*, 24*b*, and 24*c*), and a coaxial cable 40 for connecting the microwave generator 30 for oscillating microwaves and the irradiation electrodes 24 is connected to the forceps 1.

Specifically, the upper jaw portion 14 is provided with an irradiation electrode 24*a*, the lower jaw portion 116 is provided with an irradiation electrode 24*b*, and the inside of the cutter 15 is provided with an irradiation electrode 24*c*, and a coaxial cable 40 is connected to the irradiation electrode 24*c*. Although not shown, the irradiation electrodes 24 (24*a*, 24*b*, and 24*c*) arranged on the upper jaw portion 14, the cutter 15, and the lower jaw portion 116 have an insulating layer arranged on the outside, and the upper jaw portion 14, the cutter. Insulated from 15 and the lower jaw 116.

As shown in the enlarged cross-sectional view of FIG. 27 at (b), the coaxial cable 40 is composed of an insulator 42, an outer conductor 43, and an insulating coating 44 with the central conductor 41 and the central conductor 41 interposed therebetween, from the center to the outer diameter. They are arranged in this order.

The central conductor 41 is a linear conductor arranged at the center of the coaxial cable 40, and may be a single conductor having an appropriate diameter, or may be composed of a plurality of core wires.

The insulator 42 is made of a resin that surrounds the outside of the central conductor 41 and insulates the central conductors 41 and 43, and has a cylindrical shape having a predetermined wall thickness.

The outer conductor 43 is composed of braided wires provided along the outer peripheral surface of the insulator 42.

The insulating coating 44 is a coating having an insulating property and surrounds the outside of the outer conductor 43.

As described above, the coaxial cable 40 in which the central conductor 41, the insulator 42, the outer conductor 43, and the insulating coating 44 are arranged in this order from the center side has appropriate flexibility.

As shown in FIG. 27, the irradiation electrode 24*a* and the irradiation electrode 24*c* are connected to the central conductor 41 of the coaxial cable 40, the irradiation electrode 24*b* is connected to the outer conductor 43, and electromagnetic waves (microwaves) are transmitted from the irradiation electrodes 24*a* and 24*c*. Is configured to irradiate the irradiation electrode 24*b*. Further, the electrode structure may be a coaxial structure as shown in FIG. 17, and the polarity of the connection may be the same pole connection structure or the different pole connection structure.

One of the first electrode portion of the irradiation electrodes 24*a* and 24*c* of the upper jaw portion 14 and the cutter 15 and the second electrode portion of the irradiation electrode 24*b* provided on the lower jaw portion 116 is connected to the central conductor 41 of the coaxial cable 40. The other will be connected to the outer conductor 43. In this way, the forceps 1 provided with the irradiation electrodes 24*a* and 24*c* irradiate microwaves from one of the first electrode portion of the irradiation electrodes 24*a* and 24*c* and the second electrode portion of the irradiation electrode 24*b* toward the other.

As a result, the target site gripped by the gripping mechanism 17 composed of the lower jaw portion 116 and the upper jaw portion 14 can be coagulated by irradiating the target site with microwaves. Further, if necessary, the irradiation electrode 24*c* may be electrically connected to the irradiation electrode 24*b*, and microwaves may be irradiated between the upper jaw portion 14 and the cutter 15 to coagulate the living tissue.

The operation of the forceps 1 configured as described above will be described below with reference to FIGS. 28 to 30.

Similar to the embodiments of Application, in FIG. 28, the pivot portion 133 pivotally supported by the support shaft 114 by a user who inserts a finger into the ring portion 113 of the main body frame 11 and the ring portion 132 of the gripping trigger handle 13*a*. As the center of rotation, the gripping trigger handle 13*a* is rotated in a direction closer to the fixed handle frame 111 (a direction in which the lower portion of the gripping trigger handle 13*a* moves to the left in FIG. 25).

FIG. 6 shows a upper jaw gear 12*a* in which a rack gear 134 projecting upward from the pivot portion 133 and a gear tooth 121 mesh with each other by rotating the gripping trigger handle 13*a* around the pivot portion 133 in a direction close to the fixed handle frame 111. Rotate counterclockwise at 25. When the upper jaw gear 12*a* rotates counterclockwise, the near-side wire 161 of the upper jaw wire 16*a* whose proximal end is attached to the wire attachment portion 122*a* is pulled toward the proximal end side R and moves.

When the proximity side wire 161 of the upper jaw wire 16*a* moves toward the proximal end side R, the tip of the proximity side wire 161 is fixed to the proximity side attachment portion 142*a*, and the upper jaw pivotally supported by the support shaft 117*a* of the tip support portion 117. The portion 14 is pivoted in a direction in which the tip end side F is close to the lower jaw portion 116 with the support shaft 117*a* as the center of rotation (see FIG. 28).

At this time, since the cutter 15 does not rotate, it remains in the initial position as shown in FIG. 28.

As a result, in the initial state (open state) as shown in FIG. 30 (*a*), the blood vessel B, which is the target site in the living tissue, is arranged between the upper jaw portion 14 and the lower jaw portion 116, and as shown in FIG. 30 at (b). By sandwiching the blood vessel B between the upper surface of the lower jaw portion 116 and the bottom surface of the upper jaw portion 14, the blood vessel B can be gripped by the gripping mechanism 17 composed of the lower jaw portion 116 and the upper jaw portion 14.

As described above, in the state shown in FIGS. 28 and 30B in which the upper jaw portion 14 is close to the lower jaw portion 116 by operating the gripping trigger handle 13*a*, the target site such as the blood vessel B is gripped by the gripping mechanism 17. It is a gripping state to be gripped by.

When the cutting trigger handle 13*b* is further operated in the direction closer to the fixed handle frame 111 from this gripped state, the cutting trigger handle 13*b* rotates in the direction closer to the fixed handle frame 111 around the pivot portion 133, and the pivot portion The cutter gear 12*b* in which the rack gear 134 protruding upward from 133 and the gear teeth 121 mesh with each other is rotated clockwise in FIG. 26. When the cutter gear 12*b* rotates clockwise, the near-side wire 161 of the cutter wire 16*b* whose base end is attached to the wire attachment portion 122*a* is pulled toward the base end side R and moves.

When the proximity side wire 161 of the cutter wire 16*b* moves toward the proximal end side R, the tip of the proximity side wire 161 is fixed to the proximity side mounting portion 152*a*, and the cutting is axially supported by the support shaft 117*a* of the tip support portion 117. The cutter 15 pivots with the support shaft 117*a* as the center of rotation, with the tip end side F pivoting in a direction close to the lower jaw portion 116, and the cutting blade 153 pivoting beyond the upper surface of the lower jaw portion 116.

As a result, as shown in FIG. 30 at (c), the cutter 15 moves along the side surface of the upper jaw portion 14, and the blood vessel B gripped by the gripping mechanism 17 may be cut by the cutting blade 153 of the cutter 15.

As described above, by further operating the cutting trigger handle 13*b*, as shown in FIG. 29 at (b), the cutter 15 is rotated so that the cutting blade 153 exceeds the upper surface of the lower jaw portion 116 which means a cut or disconnected state.

As described above, the forceps 1 grips the target site such as the blood vessel B by the upper jaw portion 14 and the lower jaw portion 116 constituting the gripping mechanism 17, and cuts the target site by the cutter 15 together with the gripping trigger handle 13*a*. This can be done by operating with the cutting trigger handle 13*b*. Then, during the gripping/cutting of the target site by the operation of the gripping trigger handle 13*a* and the cutting trigger handle 13*b*, the target site can be condensed by irradiating the target site with a microwave from the irradiation electrode 24.

When the cutting trigger handle 13*b* is operated in the direction away from the fixed handle frame 111 from the above-mentioned cutting state, the cutting trigger handle 13*b* rotates around the pivot portion 133 in the direction away from the fixed handle frame 111. The cutter gear 12*b* in which the rack gear 134 protruding upward from the pivot portion 133 and the gear teeth 121 mesh with each other is rotated counterclockwise in FIG. 26. When the cutter gear 12*b* rotates counterclockwise, the open side wire 162 of the cutter wire 16*b* whose base end is attached to the wire attachment portion 122*b* is pulled toward the base end side R and moves.

When the open side wire 162 of the cutter wire 16*b* moves toward the base end side R, the tip of the open side wire 162 is fixed to the open side mounting portion 152*b*, and the cutting is axially supported by the support shaft 117*a* of the tip support portion 117. The cutter 15 pivots in a direction in which the tip end side F is separated (opened) from the lower jaw portion 116 with the support shaft 117*a* as the center of rotation.

As a result, the cutter 15 can be returned to the initial position shown in FIG. 26.

Further, when the gripping trigger handle 13*a* is operated in the direction away from the fixed handle frame 111 from the above-mentioned gripping state, the gripping trigger handle 13*a* rotates around the pivot portion 133 in the direction away from the fixed handle frame 111. The upper jaw gear 12*a* in which the rack gear 134 protruding upward from the pivot portion 133 and the gear teeth 121 mesh with each other is rotated clockwise in FIG. 25. When the upper jaw gear 12*a* rotates clockwise, the open side wire 162 of the upper jaw wire 16*a* whose base end is attached to the wire attachment portion 122*b* is pulled toward the base end side R to move.

When the open side wire 162 of the upper jaw wire 16*a* moves toward the proximal end side R, the tip of the open side wire 162 is fixed to the open side mounting portion 142*b*, and the upper jaw portion 14 pivotally supported by the tip support portion 117 With the axis center 117*a* as the center of rotation, the tip side F is pivoted in a direction away from the lower jaw portion 116.

As a result, the upper jaw portion 14 may be returned to the initial position shown in FIG. 25.

As described above, the forceps 1 grips the target site by the gripping mechanism 17 by moving the upper jaw portion 14 and the cutter 15 by the upper jaw wire 16*a* and the cutter wire 16*b*, respectively, and the target site is gripped by the cutting mechanism 10 so as to be cut.

Further, the upper jaw wire 16*a* made of a flexible elongated member is connected to the proximity side mounting portion 142*a* at a predetermined distance from the center of the support shaft 117*a* in the upper jaw portion 14, and moves in the tensile direction in the longitudinal direction L. It has a proximity side wire 161 to be moved, and an open side wire 162 connected to the open side mounting portion 142*b* and moved in the pulling direction in the longitudinal direction L.

The cutter wire 16*b* made of a flexible elongated member is connected to the proximity side mounting portion 152*a* separated from the center of the support shaft by a predetermined distance in the cutter 15, and is moved in the tensile direction in the longitudinal direction L. It has 161 and an open side wire 162 that is connected to the open side mounting portion 152*b* and is moved in the pulling direction in the longitudinal direction L.

Therefore, by moving the proximity side wire 161 in the pulling direction in the longitudinal direction L at a predetermined position, the upper jaw portion 14 and the cutter 15 are rotated in the pulling direction with respect to the lower jaw portion 116, and the open side wire 162 is formed. By moving the predetermined location in the tensile direction in the longitudinal direction L, the predetermined portion can be rotated in the tensile direction. Therefore, for example, when the upper jaw portion 14 (cutter 15) is rotated in the gripping direction (cutting direction) with respect to the lower jaw portion 116 by moving the proximity side wire 161 in the pulling direction, the opening side wire 162 is in the pulling direction. By moving, the upper jaw portion 14 (cutter 15) can be opened. That is, the upper jaw portion 14 (cutter 15) can be rotated with respect to the lower jaw portion 116 in the gripping direction (cutting direction) and in the opening direction by moving the opening/closing wire 16.

In this embodiment, the support shaft (117*a*) is fixed to the base of the second grip member (lower jaw portion 116), and the first grip member (upper jaw portion 14) and the cutting member (cutter) are supported by the stationary support shaft (117*a*). A tubular protrusion protruding from each of 15) is provided, and a pair of attachment points (142, 152) are provided on the outer periphery thereof. A pair of rotating shafts that rotate independently may be used.

Figure 31:
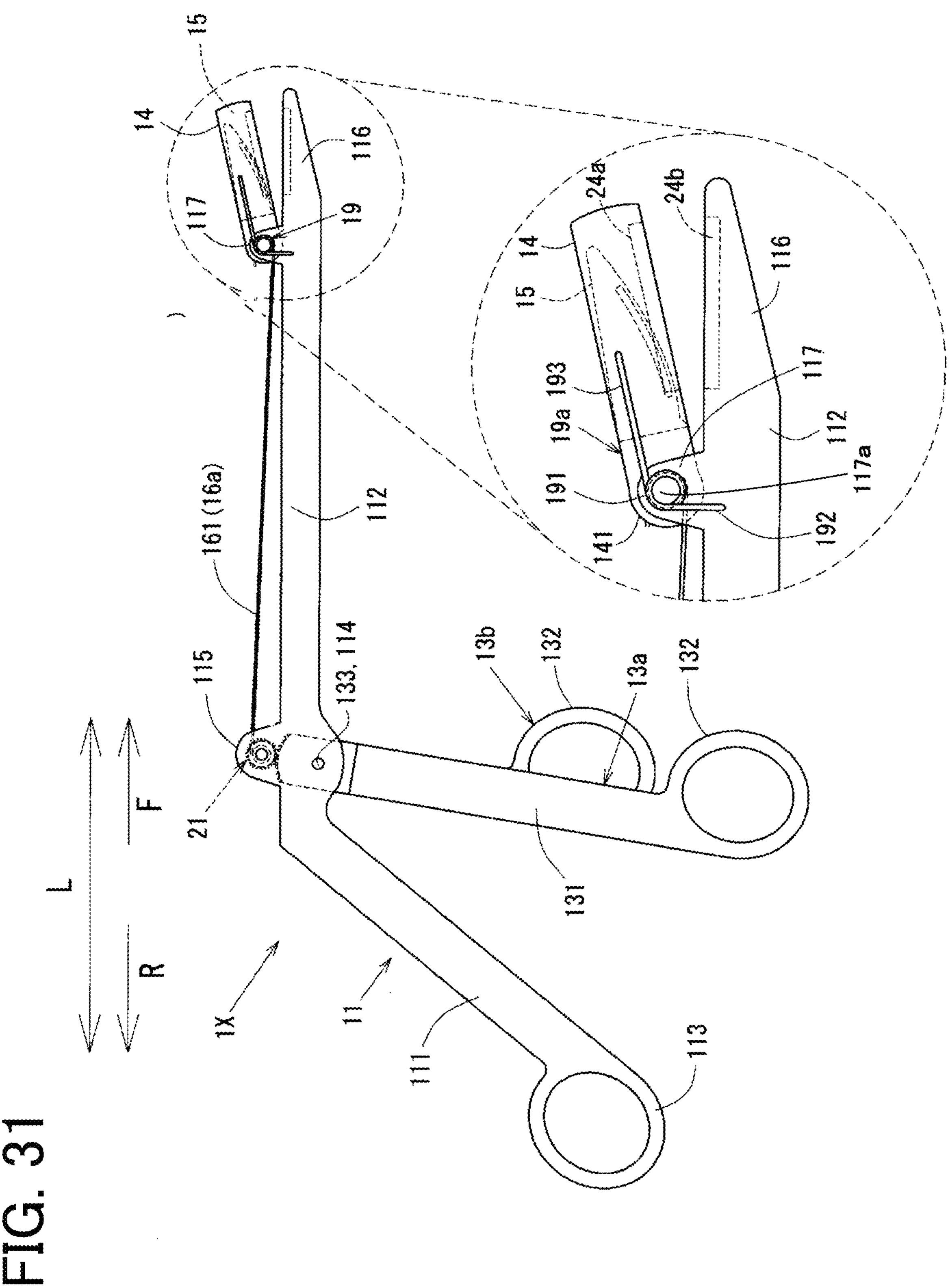
FIG. 31 is a front view of the open state forceps of another embodiment.
Figure 32:
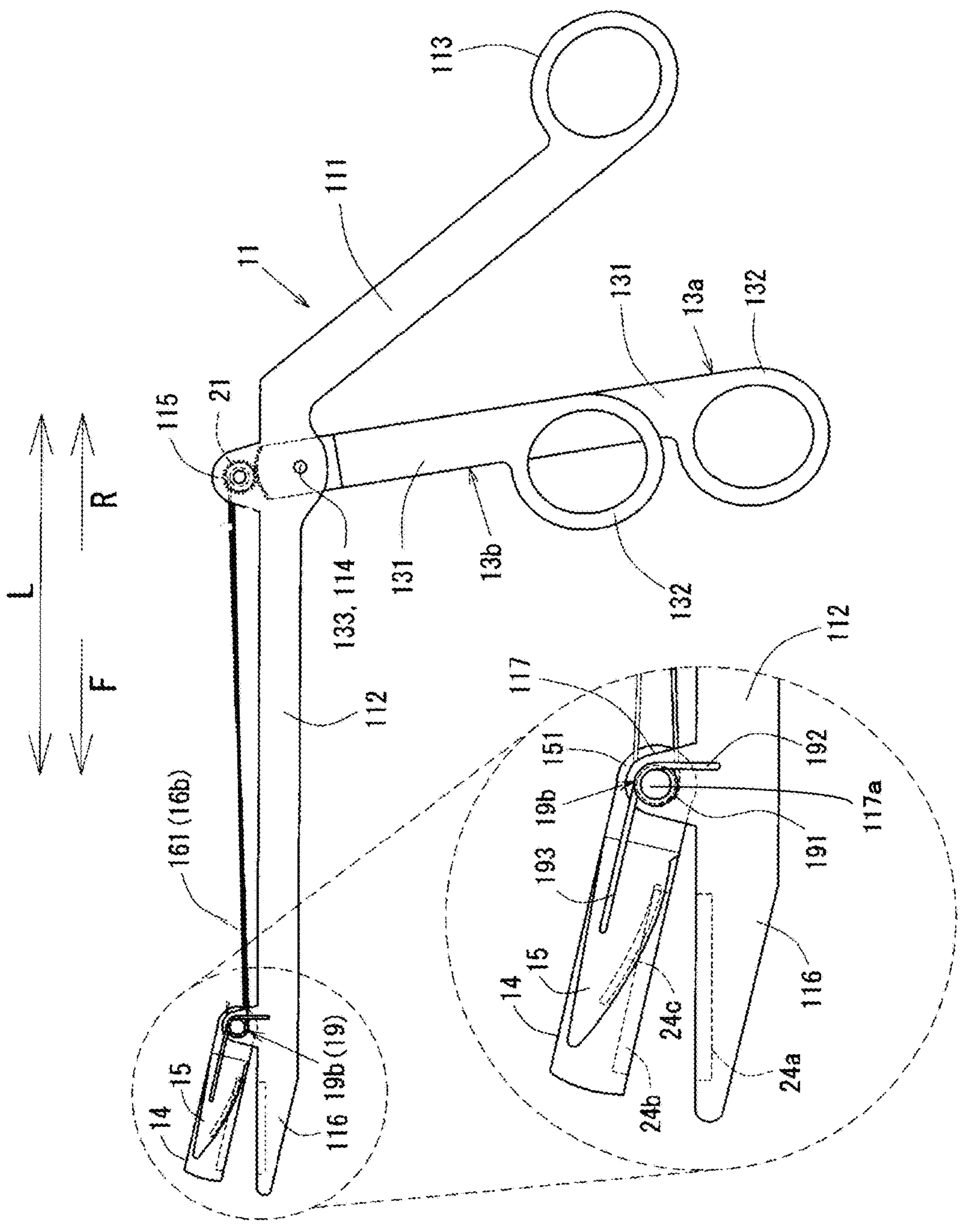
FIG. 32 is a bottom view of the open forceps of this embodiment.

Subsequently, the forceps 1X of another embodiment is shown in FIGS. 31 to 34. FIG. 31 shows a front view of the forceps 1X open state of the embodiment, FIG. 32 is the forceps 1X open state in this embodiment the back shows its side view.

Figure 33:
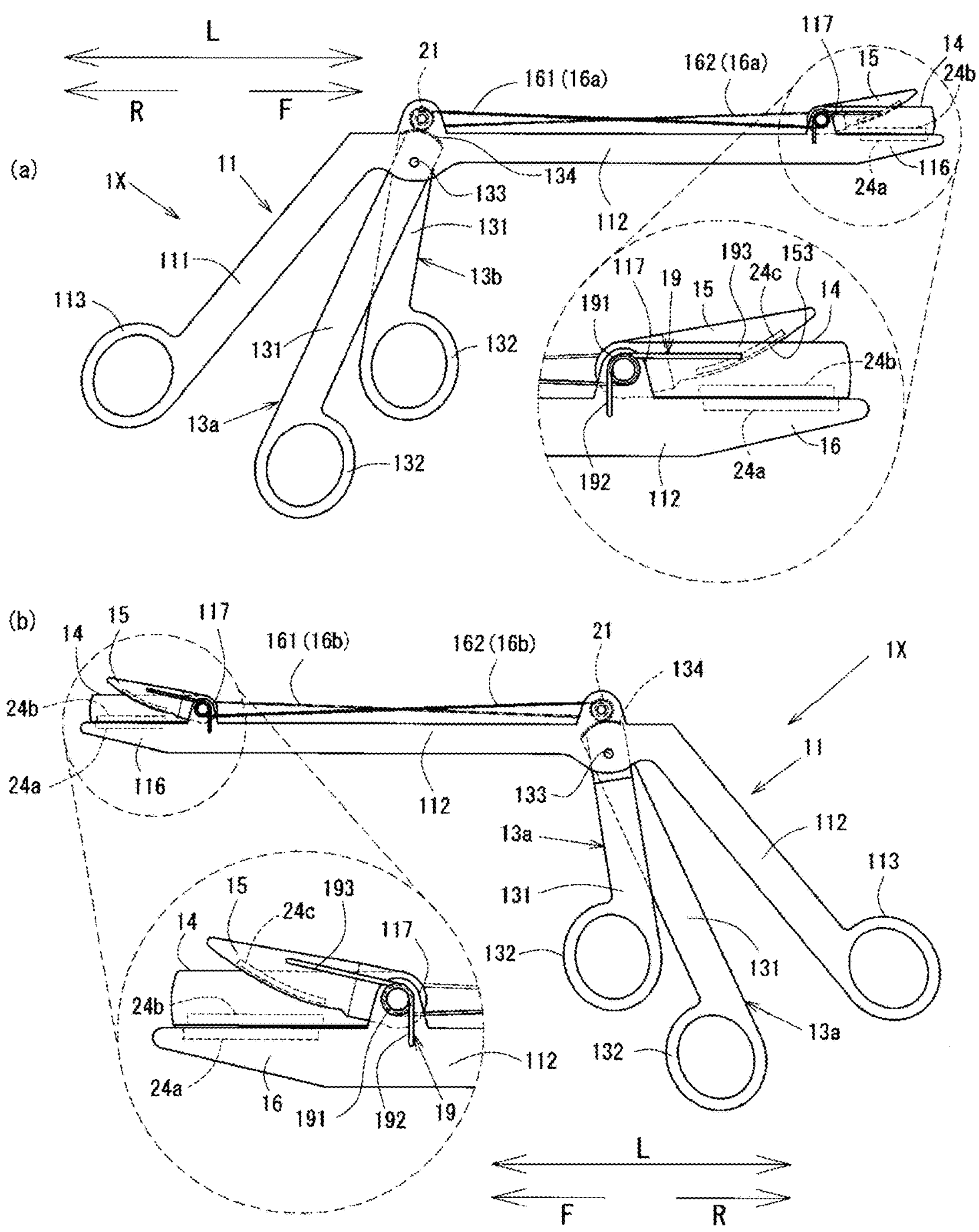
FIG. 33 is an explanatory view of a gripped state of the forceps of FIG. 31.

FIG. 33 shows an explanatory diagram of the gripped state of the forceps 1X of FIG. 31. Specifically, FIG. 33 at (a) shows a front view of the gripping mechanism 17 in the forceps 1X in a closed state, and FIG. 33 at (b) shows a rear view of the forceps 1X in the same state.

Figure 34:
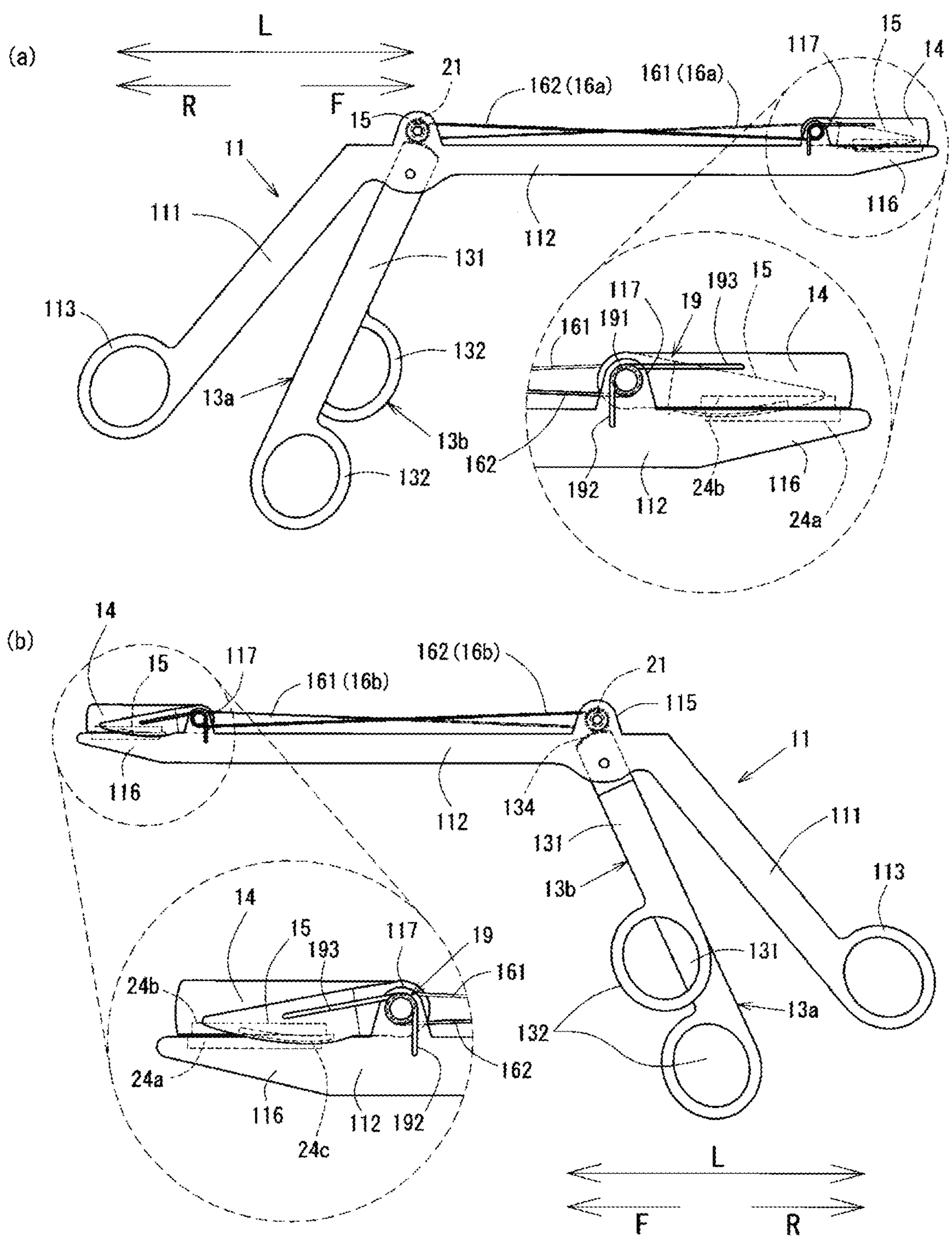
FIG. 34 is an explanatory view of a cut state of the forceps of FIG. 31.

FIG. 34 shows an explanatory diagram of the cut state of the forceps 1X of FIG. 31. Specifically, FIG. 34 at (a) shows a front view of a cutting state in which the cutter of the cutting mechanism 10 in the forceps 1X is closed, and FIG. 34 (*b*) shows a rear view of the forceps 1X in the same state.

In the following description of the forceps 1X, the same components as those of the forceps 1 are designated by the same reference numerals, and detailed description thereof will be omitted.

The forceps 1X of this embodiment does not include the open side wire 162, and the opening/closing wires 16*a* and 16*b* (16) are only the proximity side wires 161, the trigger handles 13*a* and 13*b* (13) are operated in a direction close to the fixed handle frame 111 to pull the proximity side wire 161 of the opening/closing wire 16 to the base end side R, the tip of the wire 161 is pulled and rotated toward the proximal end side R at a position where the tip of the wire 161 is fixed to the lower side around the support shaft 117*a* of the upper jaw portion 14 and the cutting cutter 15, so that the upper jaw portion 14 and the cutting cutter 15 rotate to be brought closer to the lower jaw portion 116. Then, regarding the rotation of the upper jaw portion 14 and the cutting cutter 15 in the direction in which they are separated from each other, it is rotated and released by the urging force of the spring 19.

Specifically, springs 19 (19*a* (FIG. 31) and 19*b* (FIG. 32)) are provided on the lateral side and the outer side of the upper jaw portion 14 and the cutting cutter 15, respectively. The spring 19 extends from a coil portion 191 that fits outside the support shaft 117*a* of the tip support portion 117 and one end of the coil portion 191 to provide the first arm 192 fixed to the reference frame 112 and the second arm 193 fixed to the upper jaw 14 and the cutting cutter 15.

Then, the operation of the forceps 1X configured as described above will be described below.

The operation of bringing the upper jaw portion 14 and the cutter 15 close to the lower jaw portion 116 to grip and cut is the same as the operation of the forceps 1. However, in order to operate the trigger handle 13 to bring the upper jaw portion 14 and the cutter 15 closer to each other for gripping and cutting, the spring 19*b* rotates while resisting the urging force of the spring 19*b*.

Then, in order to release the above-mentioned cutting state or the gripping state, the spring 19 is obtained by loosening the operating force of the gripping trigger handle 13*a* and the cutting trigger handle 13*b* operated in the direction close to the fixed handle frame 111. It may be automatically rotated in the opening direction and released by the urging force.

Specifically, in FIG. 31, by relaxing the operating force on the side where the gripping trigger handle 13*a* is brought close to the fixed handle frame 111 against the urging force of the spring 19*a*, the upper jaw portion 14 in the gripped state is the spring 19 The urging force of the upper jaw portion 14 rotates in a direction away from the lower jaw portion 116 and is released. [0232].

Further, in FIG. 32, by relaxing the operating force on the side where the cutting trigger handle 13*b* is brought close to the fixed handle frame 111 against the urging force of the spring 19*a*, the cutter 15 in the gripped state has the urging force of the spring 19. The tip of the cutter 15 is rotated in a direction away from the lower jaw portion 116 and is released.

As described above, the forceps 1X of the second embodiment has the same effect as the forceps 1 described above, and the upper jaw portion 14 and the cutting in the gripped state are cut without operating the trigger handle 13 in the direction away from the fixed handle frame 111. The cutter 15 in the state can be rotated in the opening direction.

Specifically, the upper jaw wire 16*a* and the cutter wire 16*b* made of a flexible long member move a predetermined portion in the pulling direction in the longitudinal direction L, and the predetermined portion moves in the pushing direction in the longitudinal direction L. Since the spring 19*a* for urging the upper jaw portion 14 in the direction of urging and the spring 19*b* for urging the cutter 15 in the direction in which the predetermined portion moves in the pushing direction are provided, the wire 16*a* for the upper jaw and the wire 16*b* for the cutter are provided. By moving a predetermined position in the tensile direction in the longitudinal direction L, the upper jaw portion 14 and the cutter 15 are rotated in the pulling direction with respect to the lower jaw portion 116, and the pushing direction is pushed by the urging force of the spring 19*a* or the spring 19*b*. Can be rotated to. Therefore, for example, when the upper jaw portion 14 (cutter 15) is rotated in the gripping direction (cutting direction) with respect to the lower jaw portion 116 by moving in the pulling direction, the urging force of the spring 19*a* (spring 19*b*) causes the upper jaw portion 14 (cutter 15) to be opened.

In the above description of the forceps 1X, only the proximity side wire 161 is provided, and the upper jaw portion 14 and the cutter 15 are rotated in a direction closer to the lower jaw portion 116 by operating the trigger handle 13, and the urging force of the spring 19 is used. The upper jaw portion 14 in the gripped state and the cutter 15 in the cutting state are rotated in the opening direction.

On the other hand, the spring 19 is configured in a direction in which the tip end side of the upper jaw portion 14 and the cutter 15 is urged toward the side closer to the lower jaw portion 116, and the trigger handle 13 is configured on the side closer to the fixed handle frame 111. By operating toward, the upper jaw portion 14 and the cutter 15 are rotated in a direction away from the lower jaw portion 116, and the tip side of the upper jaw portion 14 and the cutter 15 approaches the lower jaw portion 116 due to the urging force of the spring 19. It may be configured to be urged to the side to grip or cut.

Further, only one of the spring 19*a* and the spring 19*b* may be provided, and both the proximity side wire 161 and the open side wire 162 may be provided on the other side which is not provided. In this case, one of the cutting mechanism 10 and the gripping mechanism 17 is automatically restored by the spring 19, but the other is configured to be restored by the operation of the trigger handle 13.

Figure 35:
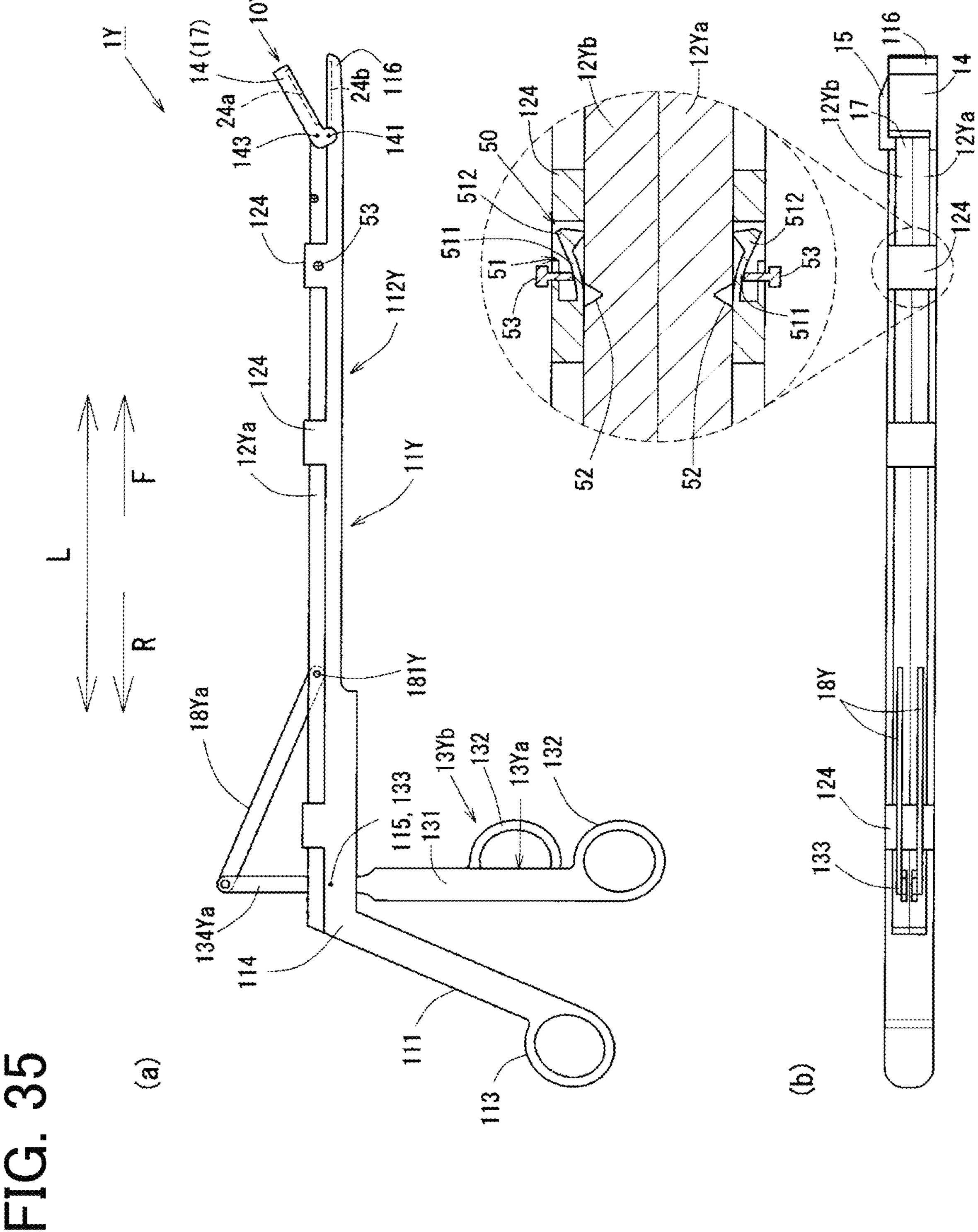
FIG. 35 is an explanatory view of open forceps of another embodiment. 35 at (a) is a front view of the forceps of the third embodiment, and FIG. 35 at (b) is a plane view of the forceps.
Figure 36:
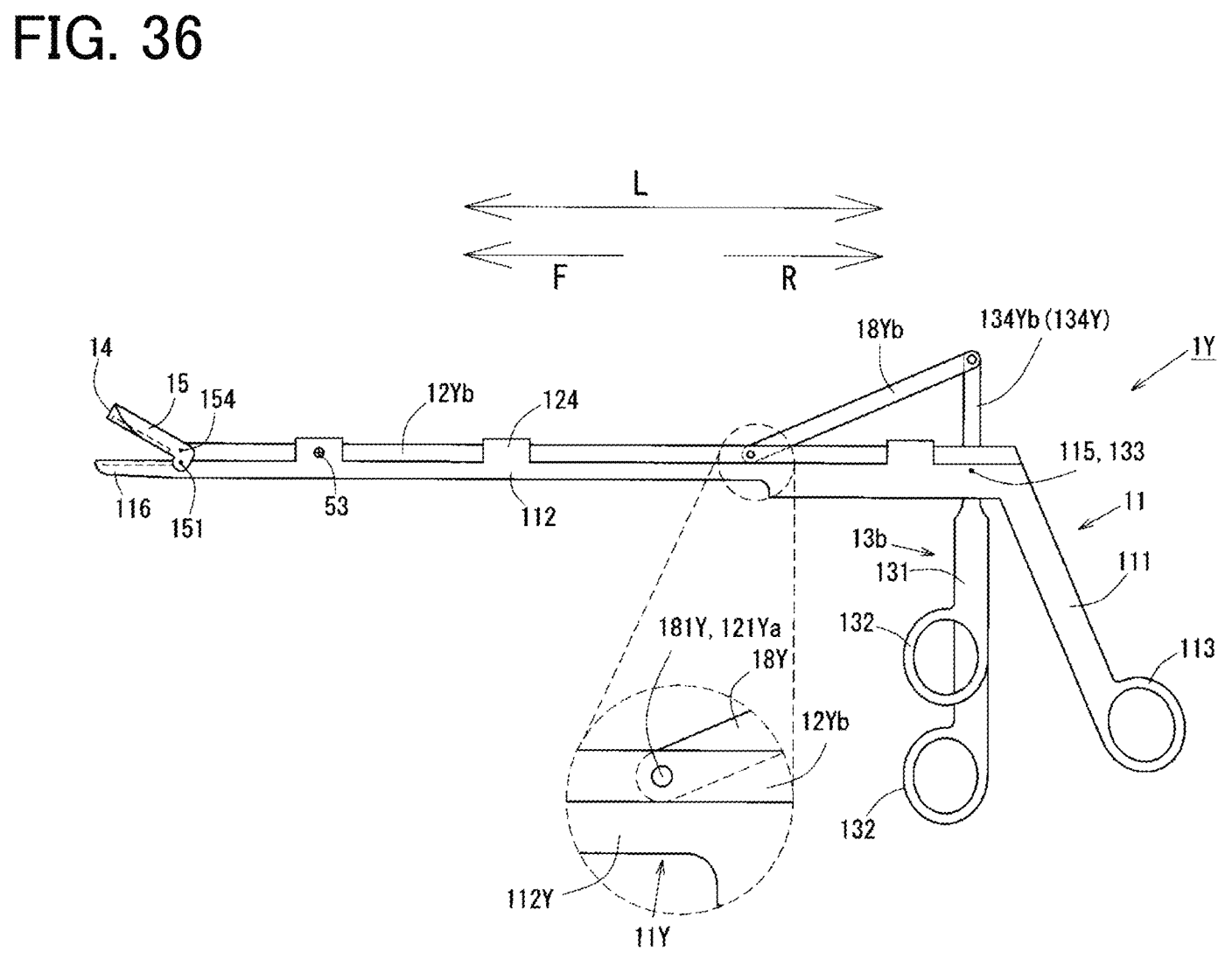
Figure 37:
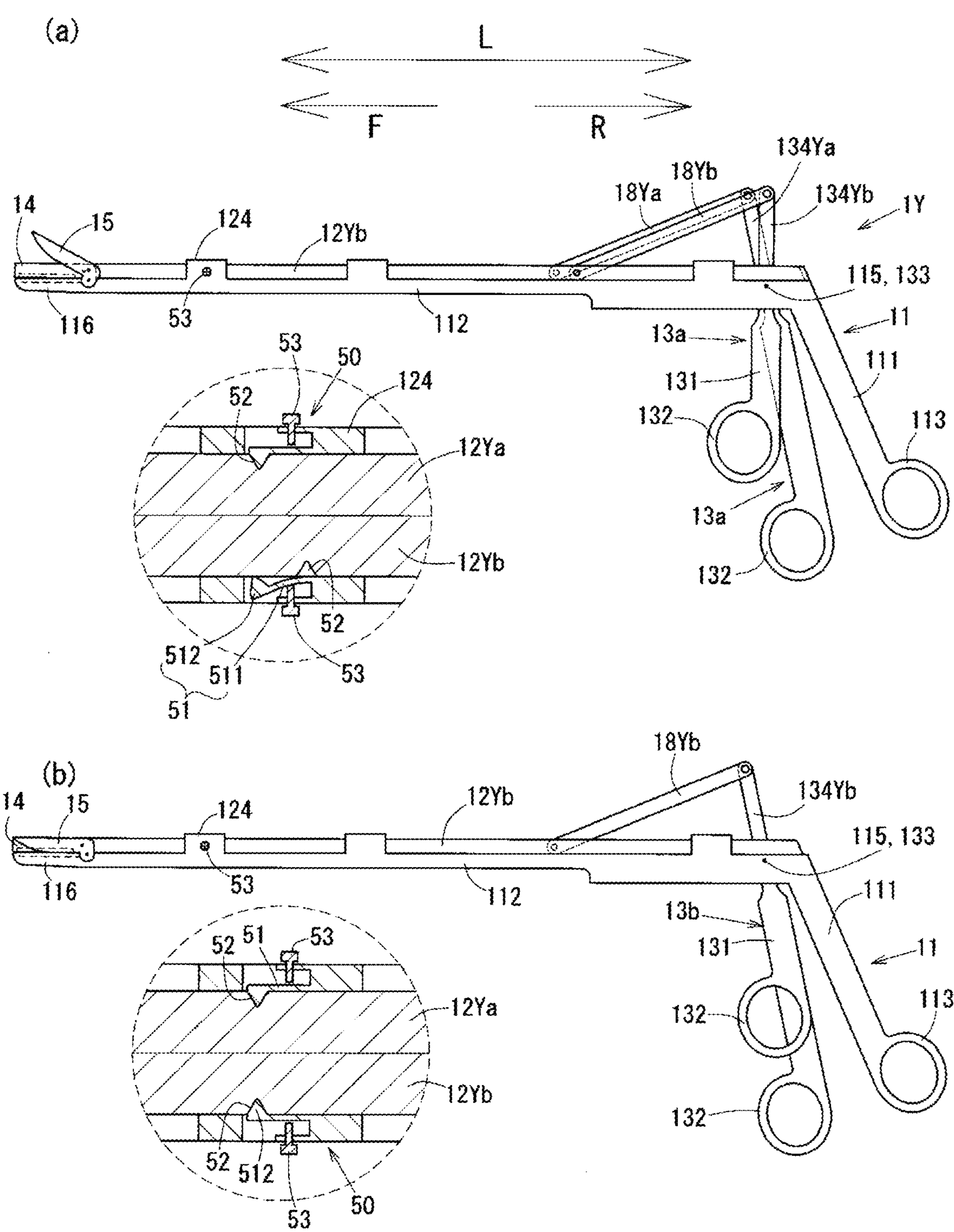
FIG. 37 is an explanatory view of the forceps of FIG. 37 at (a) is a front view of the gripping state in which the gripping mechanism of the forceps is closed, and FIG. 37 at (b) is a front view of the cutting state of the cutting mechanism of the forceps in a closed state.

Subsequently, the forceps 1Y another embodiment is shown in FIGS. 35 to 37. FIG. 35 shows an explanatory diagram of the forceps 1Y in the open state of the third embodiment. Specifically, FIG. 35 at (a) shows a front view of the forceps 1Y of this embodiment, and FIG. 35 at (b) shows a plane view of the forceps 1Y.

FIG. 36 shows a rear view of the forceps 1Y in the open state of this embodiment, and FIG. 37 shows an explanatory view of the forceps 1Y of FIG. 35. Specifically, FIG. 37 at (a) shows a front view of the gripping state in which the gripping mechanism in the forceps 1Y is closed, and FIG. 37 at (b) shows a front view of the cutting state in which the cutter of the cutting mechanism in the forceps 1Y is closed.

The enlarged views in FIG. 35 at (b) and FIG. 37 show a cross-sectional view of the regulation frame 124 near the center in the height direction.

In the following description of forceps 1Y, the same components as those of forceps 1 and 1X are designated by the same reference numerals, and detailed description thereof will be omitted.

Unlike the forceps 1 in which the operation of the trigger handle 13 is transmitted by the opening/closing wire 16 and the upper jaw portion 14 and the cutter 15 are rotated, the forceps 1Y operates the trigger handle 13Y on a rod-shaped slide plate 12Y (12Ya, 12Yb). It is configured to rotate the upper jaw portion 14 and the cutter 15 by transmitting with.

Specifically, the forceps 1Y includes a main body frame 11Y, a slide plate 12Y (12Ya, 12Yb), a trigger handle 13Y (13Ya, 13Yb), an upper jaw portion 14Y, and a cutter 15Y.

In the forceps 1Y, the first slide plate 12Y slides in the longitudinal direction L with respect to the reference frame 112Y, the upper jaw portion 14 rotates, and the second slide plate 12Yb slides in the longitudinal direction L with respect to the reference frame 112Y. The cutter 15 is configured to rotate and cut.

More specifically, the main body frame 11Y is composed of the fixed handle frame 111 and the reference frame 112Y that intersect at an obtuse angle, similarly to the main body frame 11 composed of the fixed handle frame 111 and the reference frame 112.

The first slide plate 12Ya and the second slide plate 12Yb are configured to slide along the upper surface of the reference frame 112Y. The reference frame 112Y is provided with a regulation frame 124 that regulates the first slide plate 12Ya and the second slide plate 12Yb that slide along the upper surface so as to be slidable.

The first slide plate 12Ya and the second slide plate 12Yb are formed in a plate shape, are laminated in the thickness direction, and are independently slidable along the upper surface of the reference frame 112Y and are regulated by the regulation frame 124.

An upper support shaft 121Ya that pivotally supports the drive shaft 181Ya of the arm 18Ya, which will be described later, is provided in the middle portion of the first slide plate 12Ya to which the upper jaw portion 14 is connected to the tip.

An upper support shaft 121Yb that pivotally supports the drive shaft 181Yb of the arm 18Yb, which will be described later, is provided in the middle portion of the second slide plate 12Yb to which the cutter 15 is connected to the tip.

As the trigger handle 13Y, a gripping trigger handle 13Ya that slides the first slide plate 12Ya to rotate the upper jaw portion 14, and a cutting trigger handle 13Yb that slides the second slide plate 12Yb to rotate the cutter 15. There is.

The trigger handle 13Y (13Ya, 13Yb) projects upward from the first slide plate 12Ya and the second slide plate 12Yb above the pivot portion 133 pivotally supported by the reference frame 112Y, and the upper pivot portion 134Y (134Ya, 134Yb) is provided.

An arm 18Y (18Ya, 18Yb) inclined downward and on the tip side F is connected to the upper pivot portion 134Y (134Ya, 134Yb), and the above-mentioned drive shaft 181Y (181Ya) is connected to the tip of the arm 18Y (18Ya, 18Yb). 181Yb).

Further, the forceps 1Y is provided with a click mechanism 50. For example, as shown in the enlarged view of FIG. 35, the click mechanism 50 includes a ratchet hook 51 on the inner surface of the side wall of the regulation frame 124, and a ratchet recess 52 on the side surface of the slide plate 12Y arranged inside the regulation frame 124.

The ratchet hook 51 is provided with a locking convex portion 512 at the tip of an arm 511 extending in the longitudinal direction L, and the locking convex portion 512 is pressed against the slide plate 12Y by the urging force of the arm 511. Further, an adjusting screw 53 for adjusting the pressing amount of the locking convex portion 512 by the arm 511 is provided.

When the cutting mechanism 10 and the gripping mechanism 17 are in the open state, the locking convex portion 512 of the ratchet hook 51 is not locked to the ratchet concave portion 52, and the slide plate 12Y moves to the tip side F, so that the ratchet concave portion 52 moves to the tip side F, and the slide plate 12Y moves, that is, grips by the gripping mechanism 17, by the click sound or click feeling when the locking convex portion 512 is locked to the ratchet recess 52 moved to the tip side F. It is possible to notify the cutting by the cutting mechanism 10.

Then, the urging force of the arm 511 that presses the locking convex portion 512 against the slide plate 12Y can be adjusted by screwing in and out the adjusting screw 53, and the locking convex portion 512 can be adjusted by adjusting the urging force of the arm 511. It is possible to adjust the increase/decrease of the click sound and the click feeling when locking to the ratchet recess 52.

The click mechanism 50 may be provided with a ratchet hook 51 on the side surface of the slide plate 12Y, and may be provided with a ratchet recess 52 on the inner surface of the regulation frame 124.

Further, a ratchet hook 51 and a ratchet recess 52 may be provided on the inner surface of the upper plate of the regulation frame 124 and the upper surface of the slide plate 12Y, or the ratchet hook 51 and the ratchet recess 52 may be provided on the bottom surface of the slide plate 12Y and the upper surface of the reference frame 112.

Further, the click mechanism 50 shown in FIG. 35 includes ratchet hooks 51 on both side surfaces of the regulation frame 124, and ratchet recesses 52 on both side surfaces of the first slide plate 12Ya and the second slide plate 12Yb. It may be provided only on the side surface of the slide plate 12Y corresponding to one of the side surfaces of the regulation frame 124.

When the gripping trigger handle 13Ya is operated in the direction approaching the fixed handle frame 111, the forceps 1Y configured in this way moves the upper pivotal portion 134Ya to the tip end side F with the pivotal shaft portion 133 as the rotation axis.

When the upper pivot portion 134Ya moves to the tip side F, the arm 18Y connected to the upper pivot portion 134Ya also moves to the tip side F while changing the inclination angle. When the arm 18Ya moves to the tip side F while the inclination angle changes, the first slide plate 12Ya that pivotally supports the drive shaft 181Ya of the arm 18Ya with the upper support shaft 121Yab slides to the tip side F with respect to the reference frame 112Y.

When the first slide plate 12Ya moves to the tip end side F, the lower shafted portion 141 is pivotally supported by the tip support portion 117 of the main body frame 11Y, and the rotary bearing portion 143 above it is pivotally supported by the tip upper support shaft 122Ya. In the upper jaw portion 14, the tip upper support shaft 122Y moves to the tip side F. As a result, the tip side F pivots in the direction close to the lower jaw 116 with the tip support 117 as the center, and the gripping mechanism 17 composed of the lower jaw 116 and the upper jaw 14 presses the target site such as the blood vessel B. It is in a gripping state where it can be gripped (see FIG. 40).

At this time, as shown in the enlarged view of FIG. 37 at (a), the ratchet recess 52 formed on the side surface of the moved first slide plate 12Y by the locking convex portion 512 of the ratchet hook 51 provided on the side wall of the regulation frame 124. Will be locked to. The user is notified that the ratchet recess 52 formed on the side surface of the first slide plate 12Y is in the gripped state by the click sound or click feeling when the locking convex portion 512 of the ratchet hook 51 is locked.

When the cutting trigger handle 13Yb is operated in the direction approaching the fixed handle frame 111 in the forceps 1Y in the gripped state, the upper pivot portion 134Yb moves to the tip end side F with the pivot portion 133 as the rotation axis.

When the upper pivot portion 134Yb moves to the tip side F, the arm 18Yb connected to the upper pivot portion 134Yb also moves to the tip side F while changing the inclination angle. When the arm 18Yb moves to the tip side F while the inclination angle changes, the second slide plate 12Yb that pivotally supports the drive shaft 181Yb of the arm 18Yb with the upper support shaft 121Yb slides to the tip side F with respect to the reference frame 112Y.

When the second slide plate 12Yb moves to the tip end side F, the lower shafted portion 151 is pivotally supported by the tip support portion 117 of the main body frame 11Y, and the rotary bearing portion 154 above it is pivotally supported by the tip upper support shaft 122Yb. In the cut cutter 15, the support shaft 122Yb on the tip moves to the tip side F. As a result, the tip side F pivots in the direction close to the lower jaw portion 116 with the tip support 117 as the center, and the cutting mechanism 10 composed of the lower jaw portion 116 and the cutter 15 controls the target site such as the blood vessel B. It is in a cutting state where it can be cut (see FIG. 40).

At this time, as shown in the enlarged view of FIG. 37 at (b), the locking convex portion 512 of the ratchet hook 51 provided on the side wall of the regulation frame 124 is engaged with the ratchet recess 52 formed on the side surface of the moved second slide plate 12Yb. The user is notified that the ratchet recess 52 formed on the side surface of the second slide plate 12Yb has been in a cutting state by a click sound or a click feeling when the locking convex portion 512 of the ratchet hook 51 is engaged with the ratchet recess 52 formed on the side surface of the second slide plate 12Yb.

When the cutting trigger handle 13Yb is operated in the direction away from the fixed handle frame 111 in the cutting state, the upper pivot portion 134Yb moves to the proximal end side R with the pivot portion 133 as the rotation axis.

When the upper pivot portion 134Yb moves to the proximal end side R, the arm 18Yb connected to the upper pivotal portion 134Yb also moves to the proximal end side R while changing the inclination angle. When the arm 18Yb moves to the base end side R while the inclination angle changes, the second slide plate 12Yb that pivotally supports the drive shaft 181Yb of the arm 18Yb with the upper support shaft 121Yb moves to the base end side R with respect to the reference frame 112Y. Move the slide.

When the second slide plate 12Yb moves to the base end side R, the lower shafted portion 151 is pivotally supported by the tip support portion 117 of the main body frame 11Y, and the rotary bearing portion 154 above it is pivoted to the tip upper support shaft 122Yb. In the supported cutter 15, the support shaft 122Yb on the tip moves to the proximal end side R. As a result, the proximal end side R is pivotally moved in a direction away from the lower jaw portion 116 with the tip support portion 117 as the center, and the cutting mechanism 10 composed of the lower jaw portion 116 and the cutter 15 can be opened.

Further, when the gripping trigger handle 13Ya is operated in the direction away from the fixed handle frame 111 in the gripping state, the upper pivotal shaft portion 134Ya moves to the proximal end side R with the pivotal shaft portion 133 as the rotation axis.

When the upper pivot portion 134Ya moves to the proximal end side R, the arm 18Y connected to the upper pivotal portion 134Ya also moves to the proximal end side R while changing the inclination angle. When the arm 18Ya moves to the base end side R while the inclination angle changes, the first slide plate 12Ya that pivotally supports the drive shaft 181Ya of the arm 18Ya with the upper support shaft 121Ya moves to the base end side R with respect to the reference frame 112Y. Move the slide.

When the first slide plate 12Ya moves to the base end side R, the lower shafted portion 141 is pivotally supported by the tip support portion 117 of the main body frame 11Y, and the rotary bearing portion 143 above it is pivoted to the tip upper support shaft 122Ya. In the supported upper jaw portion 14, the tip upper support shaft 122Y moves to the proximal end side R. As a result, the gripping mechanism 17 composed of the lower jaw portion 116 and the upper jaw portion 14 can be opened by pivoting in the direction in which the proximal end side R is separated from the lower jaw portion 116 with the tip support portion 117 as the center.

As described above, like the forceps 1 and 1X, the forceps 1Y also grips the target site such as the blood vessel B by the upper jaw portion 14 and the lower jaw portion 116 constituting the gripping mechanism 17, and the gripping cutter of the gripped target site. The disconnection by 15 can be performed by the operation by the trigger handles 13 (13*a*, 13*b*). Then, during the gripping/cutting of the target site by operating the trigger handles 13 (13*a*, 13*b*), the target site can be condensed by irradiating the target site with a microwave from the irradiation electrode 24.

Next, as another embodiment, the forceps 1A provided with the cutting mechanism 10 will be described with reference to FIG. 38.

Figure 38:
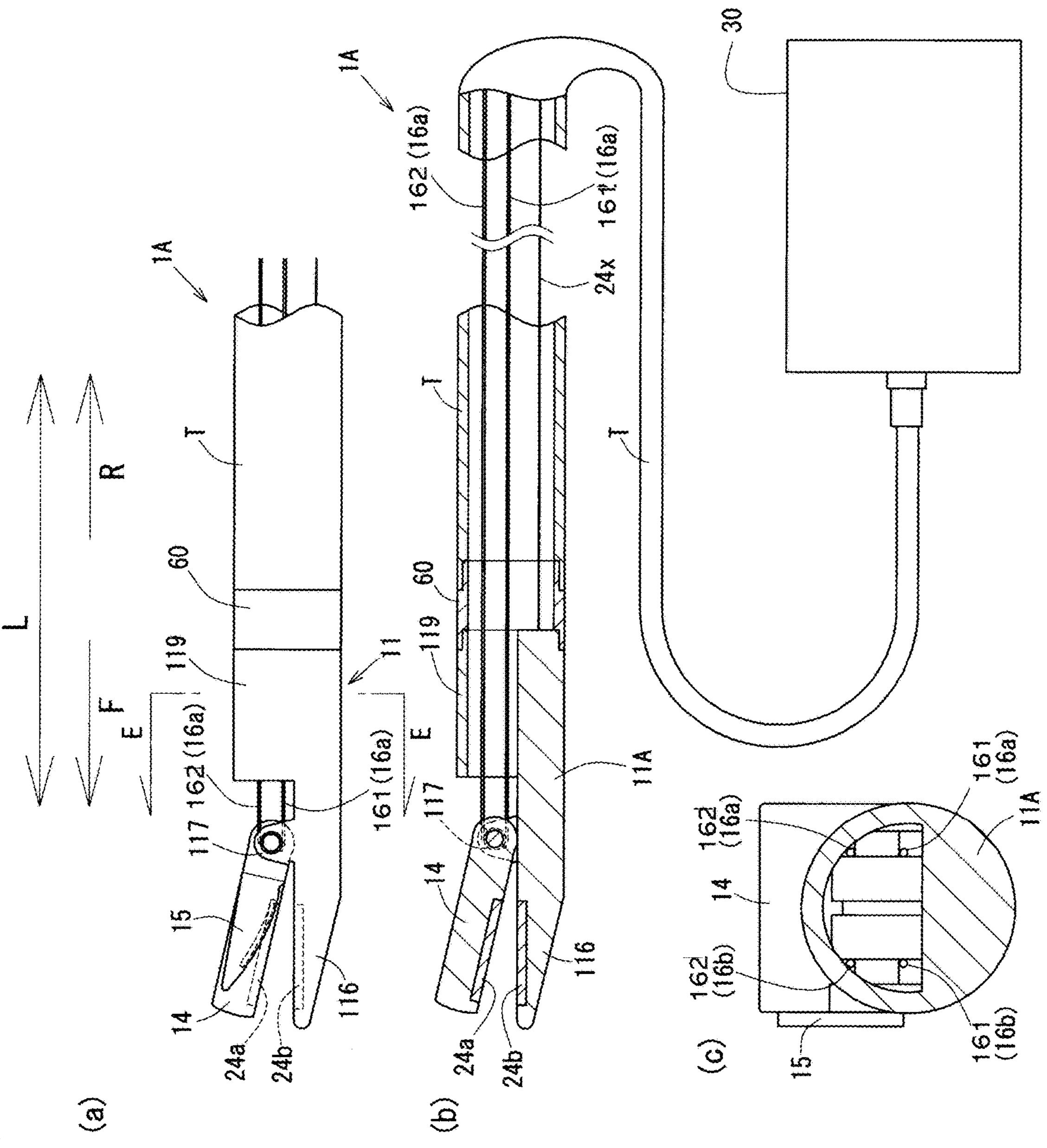
FIG. 38 is an explanatory view of an open forceps provided with a cutting mechanism of another embodiment.

FIG. 38 shows an explanatory view of the open forceps 1A provided with the cutting mechanism 10 of this embodiment. Specifically, FIG. 38 at (a) shows a rear view of the forceps 1A including the cutter 15, FIG. 38 at (b) shows a partial vertical cross-sectional view of the forceps 1A, and FIG. 38 at (c) shows a side sectional view of the E-E arrow in FIG. 38 at (a).

In the following description of the forceps 1A, the same components as those of the forceps 1, 1X, 1Y are designated by the same reference numerals, and detailed description thereof will be omitted.

Although the forceps 1A includes a cutting mechanism 10 and a gripping mechanism 17, the base of the main body frame 11A provided with the lower jaw portion 116 is configured to be attached to the attachment 60 provided at the tip of the tube T.

Specifically, the lower half of the main body frame 11A has a semicircular cross-sectional shape that is convex downward, and the base end side R is provided with an anti-arc-shaped roof 119 that is convex upward. Therefore, the base end side R of the main body frame 11A is formed in a circular cross section by the lower half portion having a semicircular cross-sectional shape convex downward and the anti-arc-shaped roof 119 convex upward, and the base end side R is formed. A fastening portion to be fastened to the fixture 60 is formed at the end portion.

The tube T to which the forceps 1A is connected via the fitting 60 may be a flexible hollow tube.

Further, in the forceps 1A, the four opening/closing wires 16 having tips attached to the upper jaw portion 14 and the cutter 15 pass through the inside of the roof 119 and insert the inside of the tube T to the opposite end to form a tube. It is connected to an operation member (not shown) provided on the opposite side of T.

The maxillary wire 16*a* and the cutter wire 16*b* move a predetermined position to the tip end side F or the proximal end side R in the longitudinal direction L, so that the predetermined portion is moved to the tip end side F or the base end side R. Thereby, the upper jaw portion 14 and the cutting cutter 15 may be rotated in the proximity direction or the opening direction with respect to the lower jaw portion 116.

Therefore, for example, by moving the open side wire 162 in the pulling direction, the upper jaw portion 14 (cutting cutter 15) is rotated with respect to the lower jaw portion 116 from the gripped state (cutting state) in the opening direction, and by moving the nearby wire 161 in the pulling direction, so that the upper jaw portion 14 (cutter 15) may be rotated in the gripping direction (cutting direction).

A coaxial cable 24*x* that supplies electricity to the irradiation electrode 24 provided on the forceps 1A is also inserted inside the tube T and connected to a microwave transmitter 30 provided on the opposite side of the tube T.

The forceps 1A configured in this way is used, for example, in a state of being inserted into a channel of an endoscope in endoscopic surgery, and is provided on the opposite side of the tube T (the root side of the endoscope). By operating (not shown), the proximity side wire 161 and the open side wire 162 of the opening/closing wire 16 are pulled, and the upper jaw portion 14 of the gripping mechanism 17 and the cutter 15 of the cutting mechanism 10 are rotated, respectively, in the living tissue. A target site can be griped, cut, and opened.

As described above, the above-mentioned forceps 1A can exert the same effect as the forceps 1, 1X, 1Y provided with the gripping mechanism 17 and the cutting mechanism 10.

Figure 45:
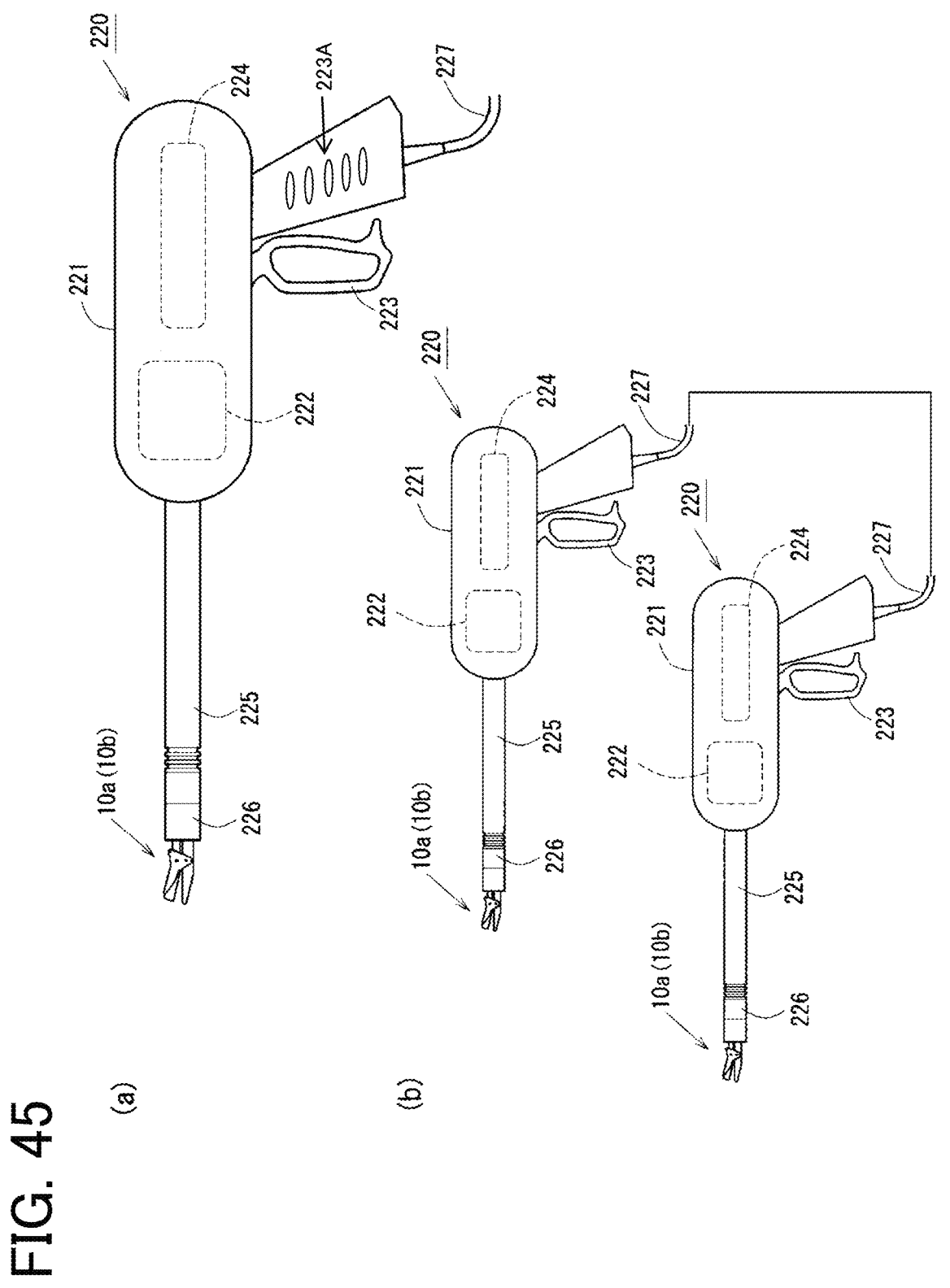
Figure 47:
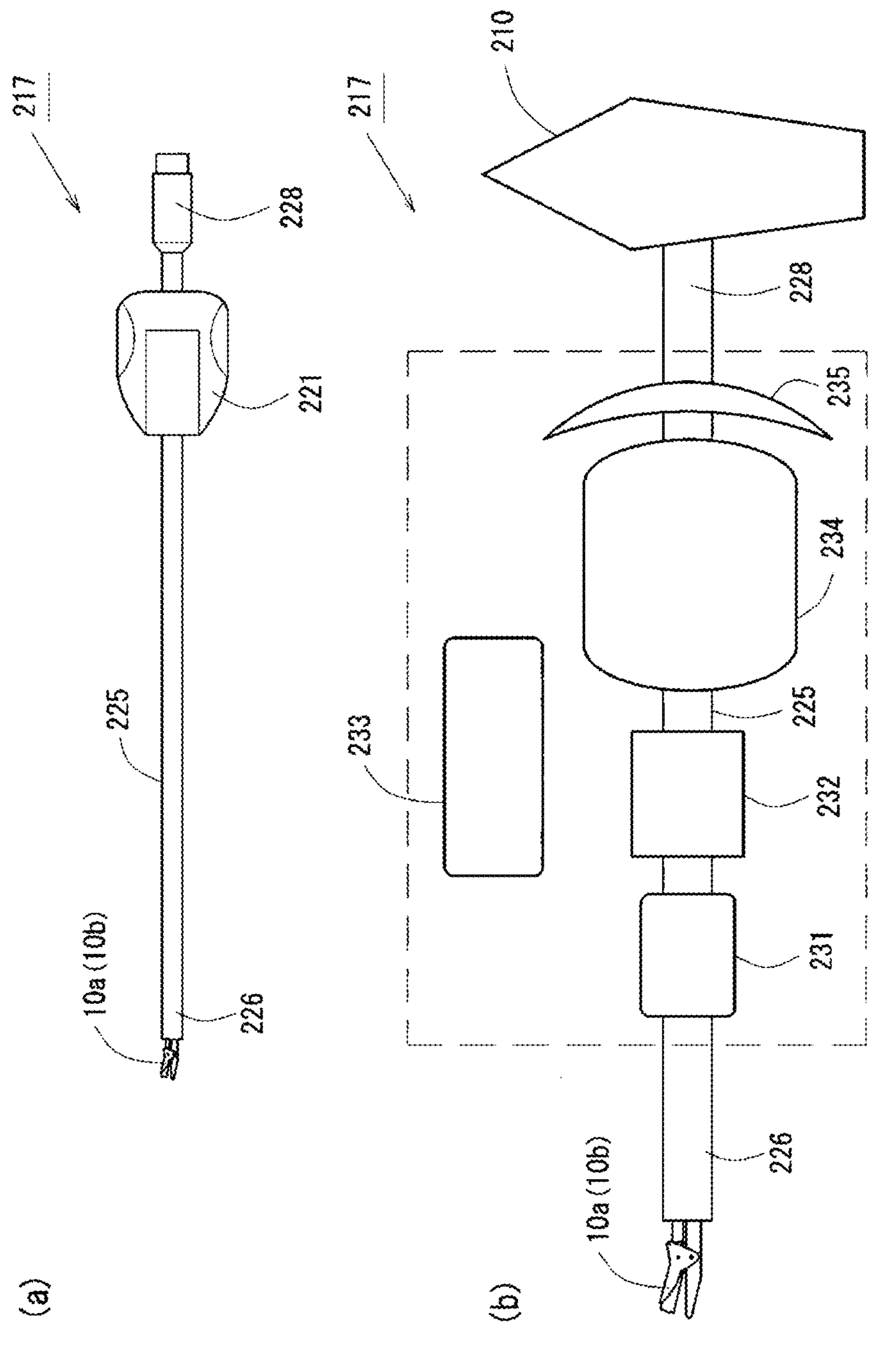
FIG. 47 is a schematic explanatory view of a surgical device in a remote surgery system.

As a modification of this embodiment (similar to FIG. 16), an electronic module 31 is provided for the end effector in the forceps 1A, and the microwave irradiation module 222 of FIG. 45 is incorporated. Or as shown in FIG. 47 at (b), it may be an electronic module that appropriately incorporates the electronic circuit of the surgical apparatus 221. By providing the electronic module 31, it is possible to reduce the size of medical equipment and improve the convenience of surgery.

Next, as another embodiment, the forceps 1B provided with the cutting mechanism 10 will be described with reference to FIG. 39.

Figure 39:
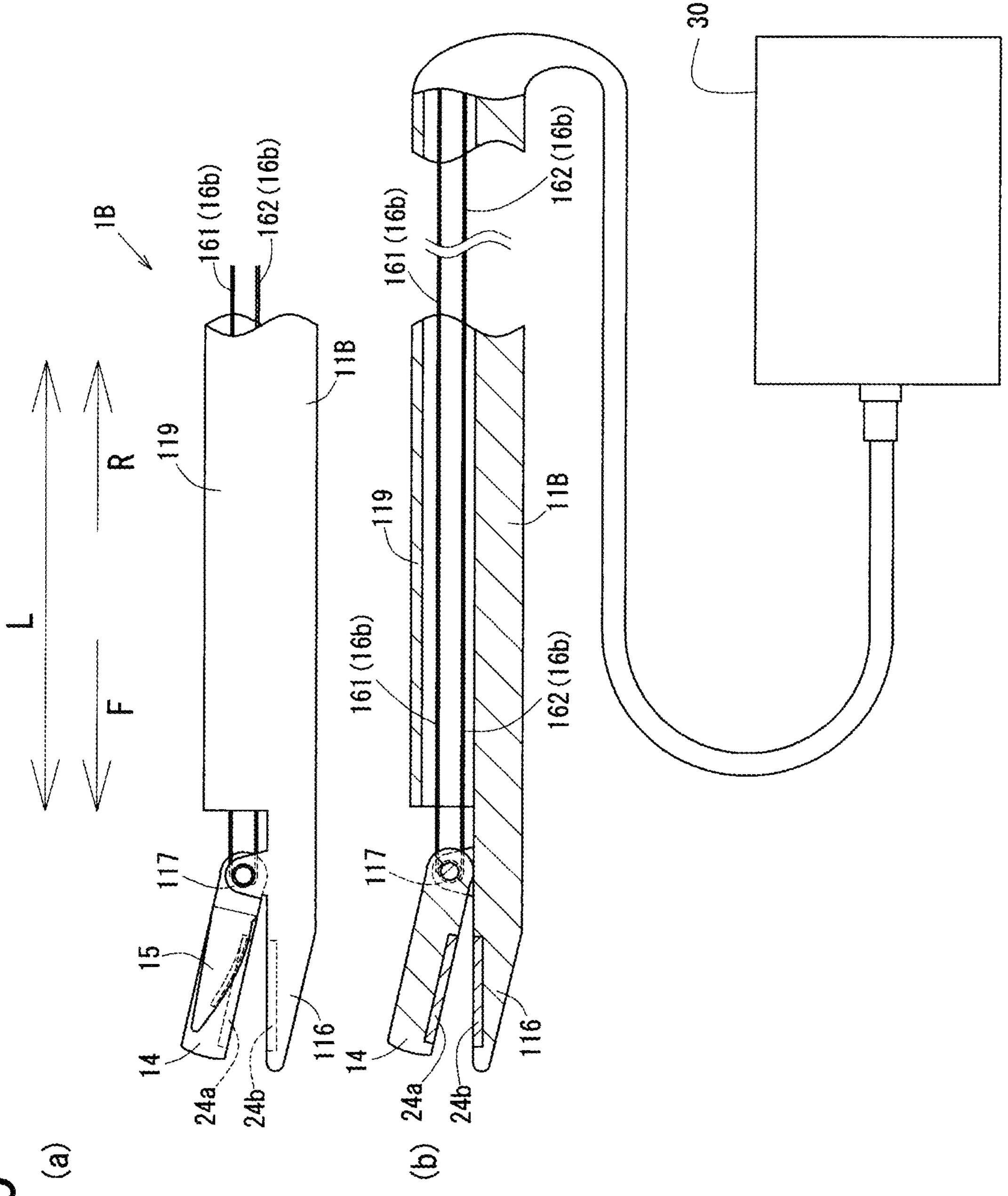
FIG. 39 is an explanatory view of an open forceps provided with a cutting mechanism of another embodiment.

FIG. 39 shows an explanatory view of the open forceps 1B provided with the cutting mechanism 10 of this embodiment. Specifically, FIG. 39 at (a) shows a rear view of the forceps 1B, and FIG. 39 at (b) shows a partial vertical sectional view of the forceps 1B.

Incidentally, definitive below forceps in the description of the forceps 1B, detailed explanation similar to the structures of forceps 1, 1X, 1Y and 1A will be denoted by the same reference numerals given to the same components as the forceps 1A.

Though, the base of the main body frame 11 is attached to the attachment 60 provided at the tip of the tube T in the above-mentioned forceps 1A, the forceps 1B does not use the tube T and the fixture 60, and the main body frame 11B and the roof 119 forming a circular cross-sectional shape are formed with the same length as the tube T in the forceps 1A.

Although the main body frame 11B and the roof 119 having a circular cross-sectional shape have predetermined flexibility, the portion constituting the lower jaw portion 116 has a rigid structure.

The forceps four closing wires 16 distal to the upper jaw 14 and the cutter 15 is mounted in terminal 1B is adapted to pass through the inside of the roof 119, to the opposite end switch inserted through the interior of the cube T, Ji is connected to the operation section provided on the opposite side of the cube T (not shown).

Further, forceps coaxial cable for supplying electricity to the radiation electrode 24 provided on the terminal 1B not shown) is Chi is inserted inside the cube T, Ji connected to a microwave oscillator 30 provided on the opposite side of the cube T Has been done.

The forceps 1B configured in this way is used in the same manner as the forceps 1A, for example, in a state of being inserted into the channel of the endoscope in endoscopic surgery. by operating an operation member (not shown) provided on the opposite side of the tube T (the root side of the endoscope), it is performed that by pulling the proximity side wire 161 and the open side wire 162 of the opening/closing wire 16, the upper jaw portion 14 of the gripping mechanism 17 and the cutting cutter 15 of the cutting mechanism 10 are rotated respectively to grasp, cut, and open the target site, which is a living tissue. Furthermore, the target portion, which is a living tissue, may be coagulated with the irradiation electrode 24.

As described above, the above-mentioned forceps 1B can exert the same effect as the forceps 1, 1X, and 1Y provided with the gripping mechanism 17 and the cutting mechanism 10 in the same manner as the forceps 1A.

An opening/closing wire 16 having a thickness sufficient to slide in the internal space may be inserted inside the main body frame 11A and the roof 119. In this case, the opening/closing wire 16 having a thickness sufficient to slide in the internal space can move not only in the pulling direction toward the proximal end side R but also in the pushing direction toward the distal end side F, and the upper jaw. The portion 14 and the cutter 15 can be rotated in either direction.

Next, as another embodiment, the end effector 10*c* for irradiating a living tissue with microwaves will be described with reference to FIGS. 40 and 41.

Figure 41:
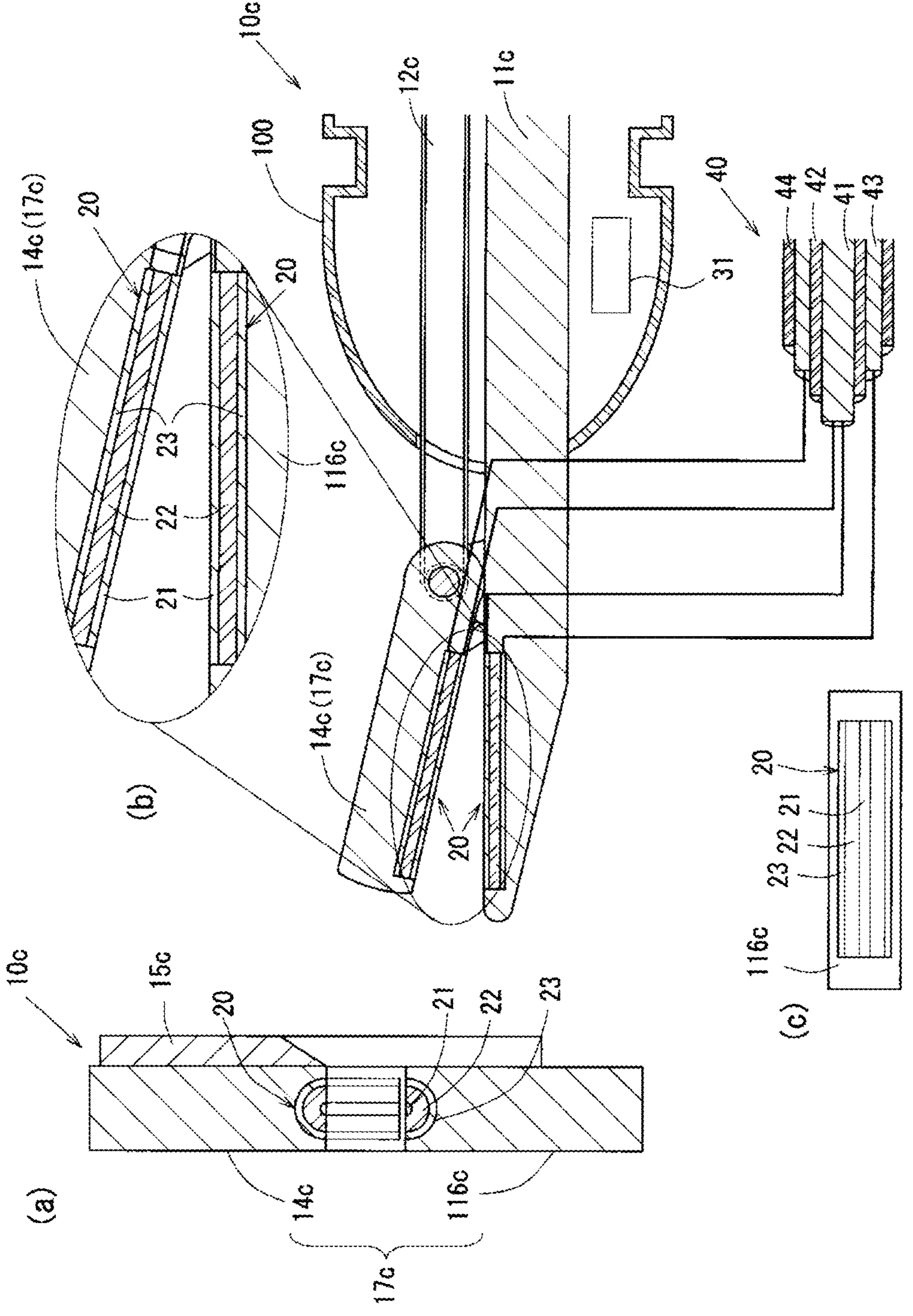
FIG. 41 is a schematic explanatory view of the end effector of FIG. 40.

FIG. 41 shows a schematic front view of the end effector 10*c* of this embodiment.

Figure 40:
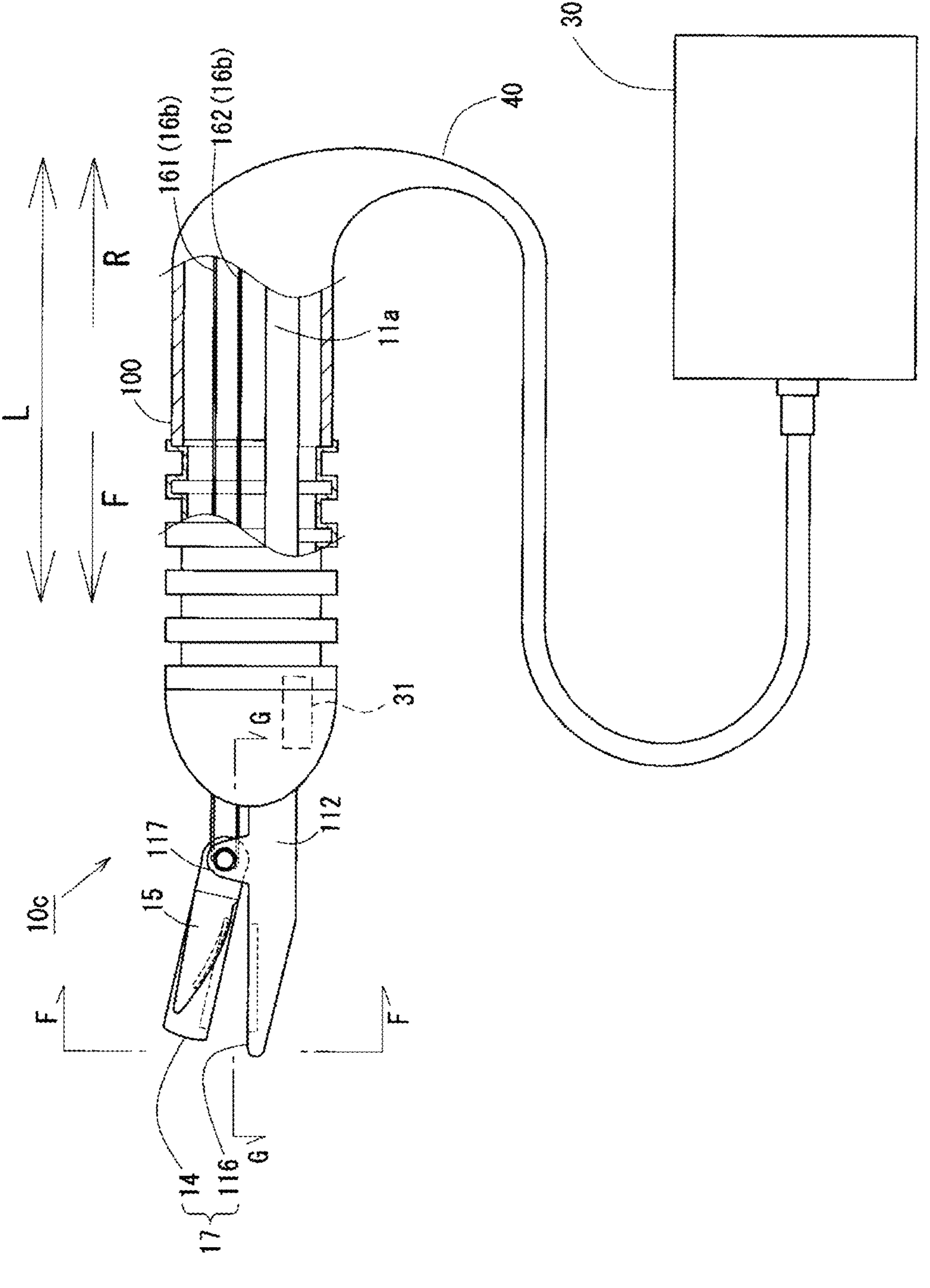
FIG. 40 is a schematic front view of an end effector of another embodiment.

FIG. 41 shows a schematic explanatory view of the end effector 10*c* of FIG. 40. Specifically, FIG. 41 at (a) shows a side sectional view taken along the line FF in FIG. 40, FIG. 41 at (b) shows a partial vertical sectional view of the end effector 10*c*, and FIG. 41 at (c) shows a partial vertical sectional view in FIG. 40. An enlarged plane view of the GG arrow is shown, and FIG. 41 at (c) shows an enlarged view of FIG. 41 at (b).

Figure 42:
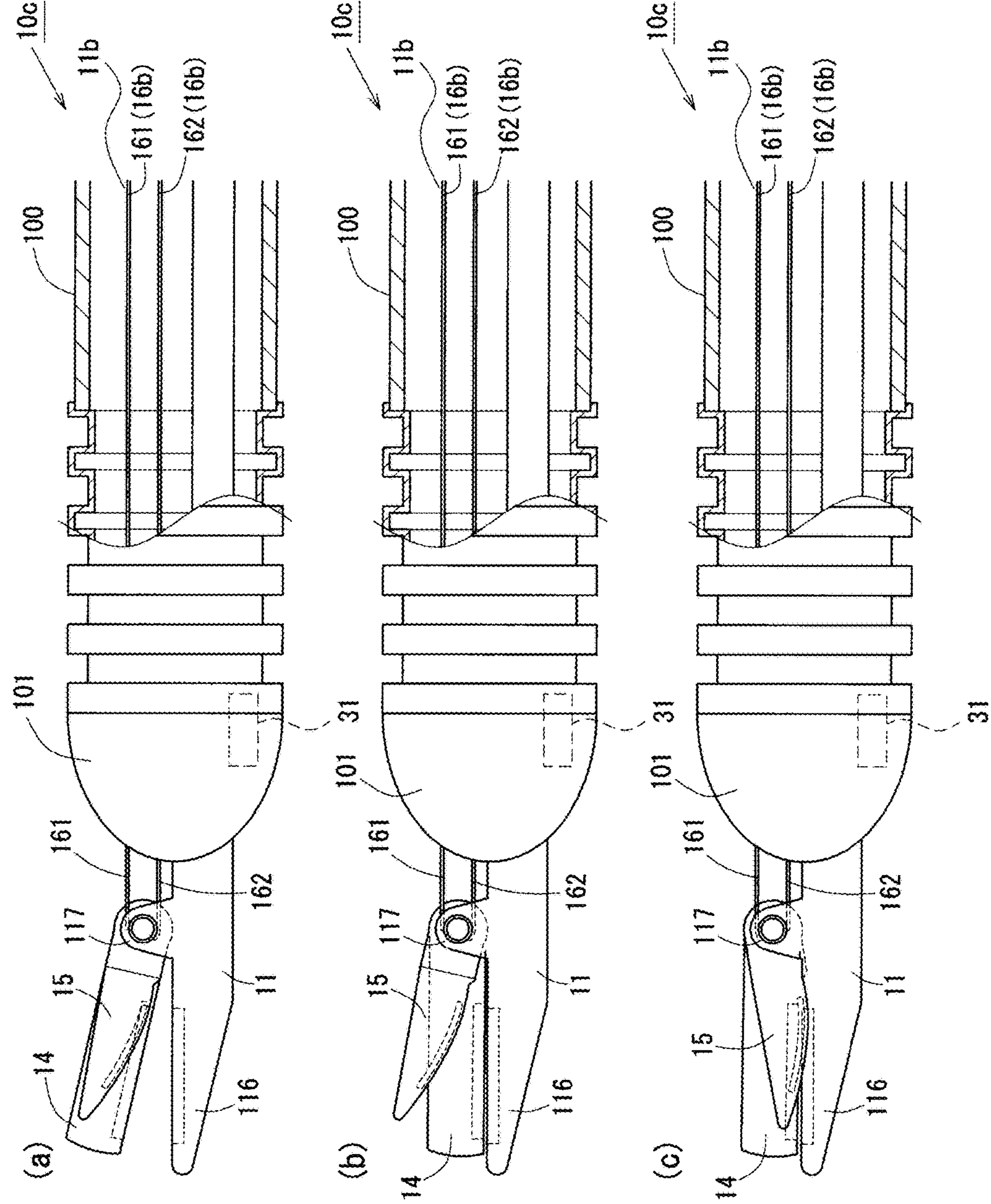
FIG. 42 is a schematic explanatory view of an end effector of another embodiment.

FIG. 42 shows a schematic explanatory view of the end effector 10*c* of another embodiment. Specifically, FIG. 42 at (a) shows a schematic front view of the end effector 10*c* in the normal state, FIG. 42 at (b) shows a schematic front view of the end effector 10*c* in the gripped state, and FIG. 42 at (c) shows a schematic front view of the end effector 10*c* in the gripped state. A schematic front view of the end effector 10*c* is shown.

The end effector 10*c* is used for a multifunctional surgical instrument and corresponds to the cutting mechanism 10 in the forceps 1 described above. Therefore, the same components as those in the above-mentioned forceps 1 are designated by the same reference numerals. Further, the end effector in this embodiment can constitute the above-mentioned cutting device, cutting mechanism, and forceps, and includes other similar configurations.

In addition, in FIGS. 40 and 41, a part of the tip end side F of the end effector 10*c* is shown.

The end effector 10*c* has a reference shaft 11*a* (corresponding to the reference frame 112 in the cutting mechanism 10) and an upper jaw portion that penetrate the bellows-shaped flexible portion 101 provided at the tip of the tubular support 100 attached to the multifunctional surgical device. There are 14, a cutter 15, and an opening/closing wire 16.

In the reference shaft 11*a*, the portion corresponding to the inside of the flexible portion 101 is configured to have flexibility that can be deformed by following the movable flexible portion 101, but is driven. A wire may be used as the above.

The operation of the upper jaw portion 14 and the cutter 15 in the end effector 10*c* configured in this way is the same as that of the upper jaw portion 14 and the cutter 15 of the cutting mechanism 10 in the forceps 1 described above, and the opening/closing wire 16 is connected to the longitudinal direction L. By moving to, the target site can be gripped by the gripping mechanism 17 composed of the lower jaw portion 116 and the upper jaw portion 14 provided at the end of the tip end side F of the reference shaft 11*a*, and can be cut by the cutter 15.

A coaxial electrode 20 along the longitudinal direction L is provided on the upper surface of the lower jaw portion 116 and the bottom surface of the upper jaw portion 14 of the end effector 10*c* configured in this way.

Further, a coaxial cable 40 for connecting the microwave transmitter 30 for irradiating microwaves and the coaxial electrode 20 is connected to the end effector 10*c*. The microwave transmitter 30 may be provided inside the end effector 10*c*.

As shown in the enlarged cross-sectional view in FIG. 41, the coaxial cable 40 is composed of an insulator 42, an outer conductor 43, and an insulating coating 44 with the central conductor 41 and the central conductor 41 interposed therebetween, and the coaxial cable 40 is formed from the center toward the outer diameter. They are arranged in order and have appropriate flexibility.

As shown in the enlarged view in FIG. 40 at (c), the coaxial electrodes 20 provided on the bottom surface of the upper jaw portion 14 and the upper surface of the lower jaw portion 116 include the central conductor 21, the semicircular insulator 22 having a semicircular cross section, and the semicircle. It is composed of a semicircular tubular semicircular conductor 23 arranged outside the insulator 22.

As shown in FIG. 41 at (c), the coaxial electrode 20 configured in this way has a semi-cylindrical shape and is configured to have a predetermined length, and has a flat surface on the bottom surface of the upper jaw portion 14 and the upper surface of the lower jaw portion 116. Are arranged along the longitudinal direction so as to face each other. Although not shown, the coaxial electrode 20 arranged on the upper jaw portion 14 and the lower jaw portion 116 has an insulating layer arranged on the outside and is insulated from the upper jaw portion 14 and the lower jaw portion 116.

Then, as shown in FIG. 41 at (b), the central conductor 21 of each coaxial electrode 20 provided in the upper jaw portion 14 and the lower jaw portion 116 and the central conductor 41 of the coaxial cable 40 are connected to each other, and half of the coaxial electrode 20. The circular conductor 23 and the outer conductor 43 of the coaxial cable 40 are connected to form the same pole connection. If necessary, one of them may be connected in the opposite polarity.

In this way, the coaxial electrode 20 connected to the microwave transmitter 30 via the coaxial cable 40 becomes a semicircular tube with the central conductor 21 of the coaxial electrode 20 via the coaxial cable 40 when the microwave transmitter 30 operates. A microwave can be irradiated between the conductor 23 and the conductor 23.

When a microwave is irradiated from the coaxial electrode 20 in a gripped state in which the blood vessel B, which is the target site, is gripped by the gripping mechanism 17, the blood vessel B gripped by the gripping mechanism 17 is condensed by the microwave. Then, in the blood vessel B, the portion condensed by the microwave irradiated from the coaxial electrode 20 can be cut by the cutter 15. As a modification of this embodiment, FIG. 39 shows an embodiment in which the electronic module 31 is built in the end effector 10*c*.

This is an example of incorporating the above-mentioned microwave transmitter 30 in the end effector 10*c*, but an electronic module in which the microwave irradiation module 222 of FIG. 45 is incorporated or the electronic circuit of the surgical apparatus 221 shown in FIG. 47 at (b) is appropriately incorporated. May be. By providing the electronic module 31 in the end effector 10*c*, the medical device can be miniaturized and the convenience of surgery is enhanced.

Further, the end effector 10*c* may be configured by connecting coaxial electrodes 20 provided on the facing surfaces of the lower jaw portion 116*a* and the upper jaw portion 14 so as to have opposite polarities.

Further, although not shown, in the end effector 10*c*, a coaxial electrode 20 may be provided on the side surface of the cutter 15 in addition to the facing surface between the lower jaw portion 116*a* and the upper jaw portion 14, or the coaxial electrode 20 may be provided on the upper jaw portion 14. The coaxial electrode 20 may be provided on the upper surface of the lower jaw portion 116*a* and the side surface of the cutter 15 without providing the 20. Further, the coaxial electrode 20 may be provided only on one of the facing surfaces of the upper jaw portion 14 and the lower jaw portion 116*a*.

Figure 43:
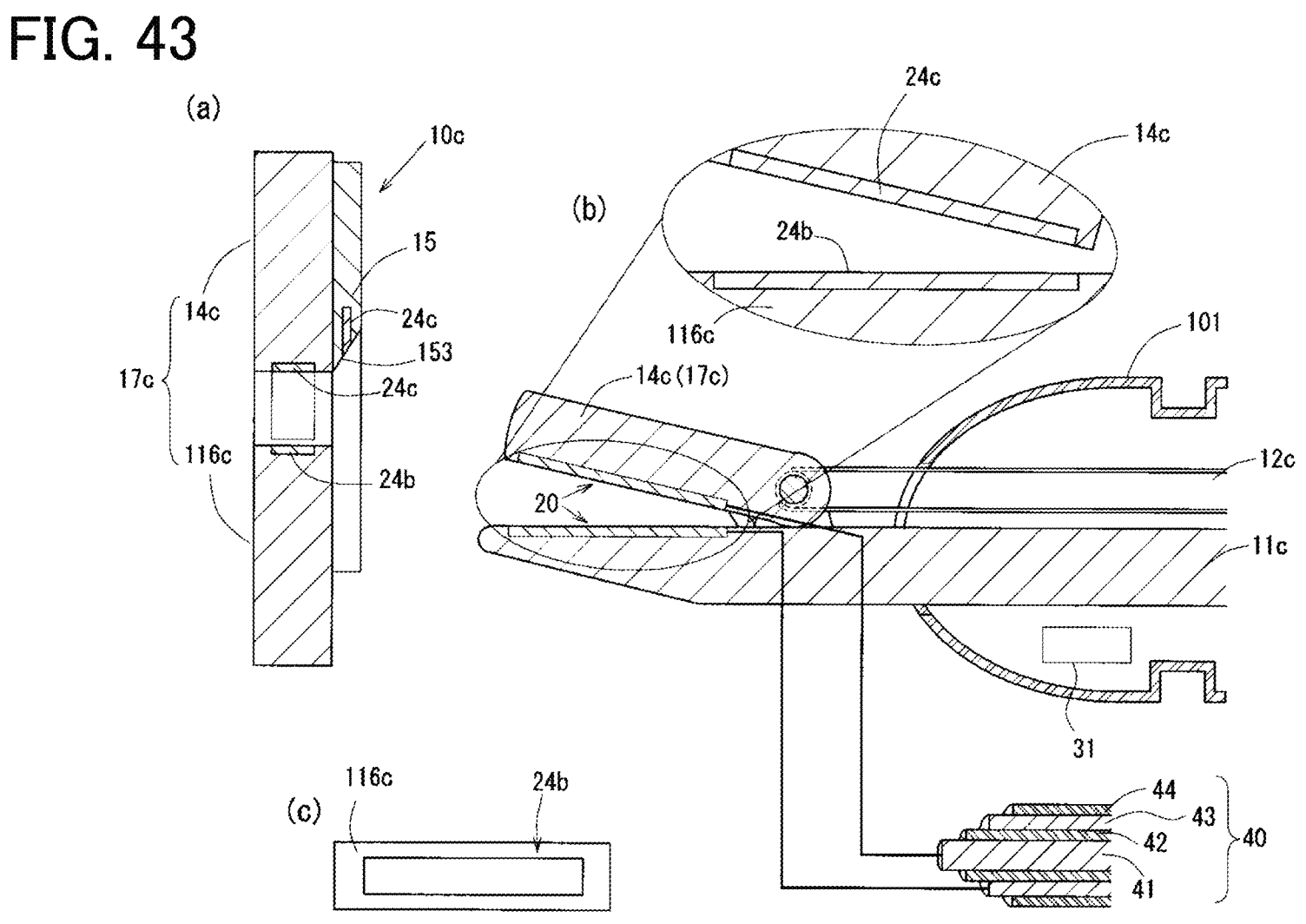

Further, as shown in FIG. 43, the above-mentioned irradiation electrodes 24*a* and 24*b* may be provided instead of the coaxial electrodes 20 provided on the upper jaw portion 14 and the lower jaw portion 116*a* in the end effector 10*c*. Further, an irradiation electrode 24*c* may be provided on the side surface of the cutter 15. 43 at (a) shows a vertical cross-sectional view of the end effector 10*c* provided with the irradiation electrode 24 (24*a*, 24*b*, 24*c*), and FIG. 43 at (b) shows a partially enlarged vertical cross-sectional view of the end effectors 10*c* provided with the irradiation electrode 24.

Furthermore, at least one of the upper jaw portion 14, the cutter 15 and the lower jaw portion 116 in the above-mentioned forceps 1, 1X, 1Y may be provided with a coaxial electrode 20 connected to the microwave transmitter 30 by a coaxial cable 40.

When the coaxial electrode 20 is provided on both the lower jaw portion 116*a* and the upper jaw portion 14 of the end effector 10*c*, or when the coaxial electrode 20 is provided on the lower jaw portion 116*a* and the cutter 15, further, when the coaxial electrodes 20 are provided on all of the lower jaw portion 116*a*, the upper jaw portion 14 and the cutter 15, the coagulated portion in the blood vessel B may be cut by the cutting mechanism in the end effector 10*c*, for example.

Surgical equipment such as the end effector 10*c* that irradiates microwaves emits less smoke and mist, has a strong hemostatic function, and is ideal for surgical support in closed spaces such as endoscopic surgery and robotic surgery. However, when there is a lot of bleeding, hemostasis in the blood pool and hemostasis in the liquid are diminished like other energy devices.

Figure 44:
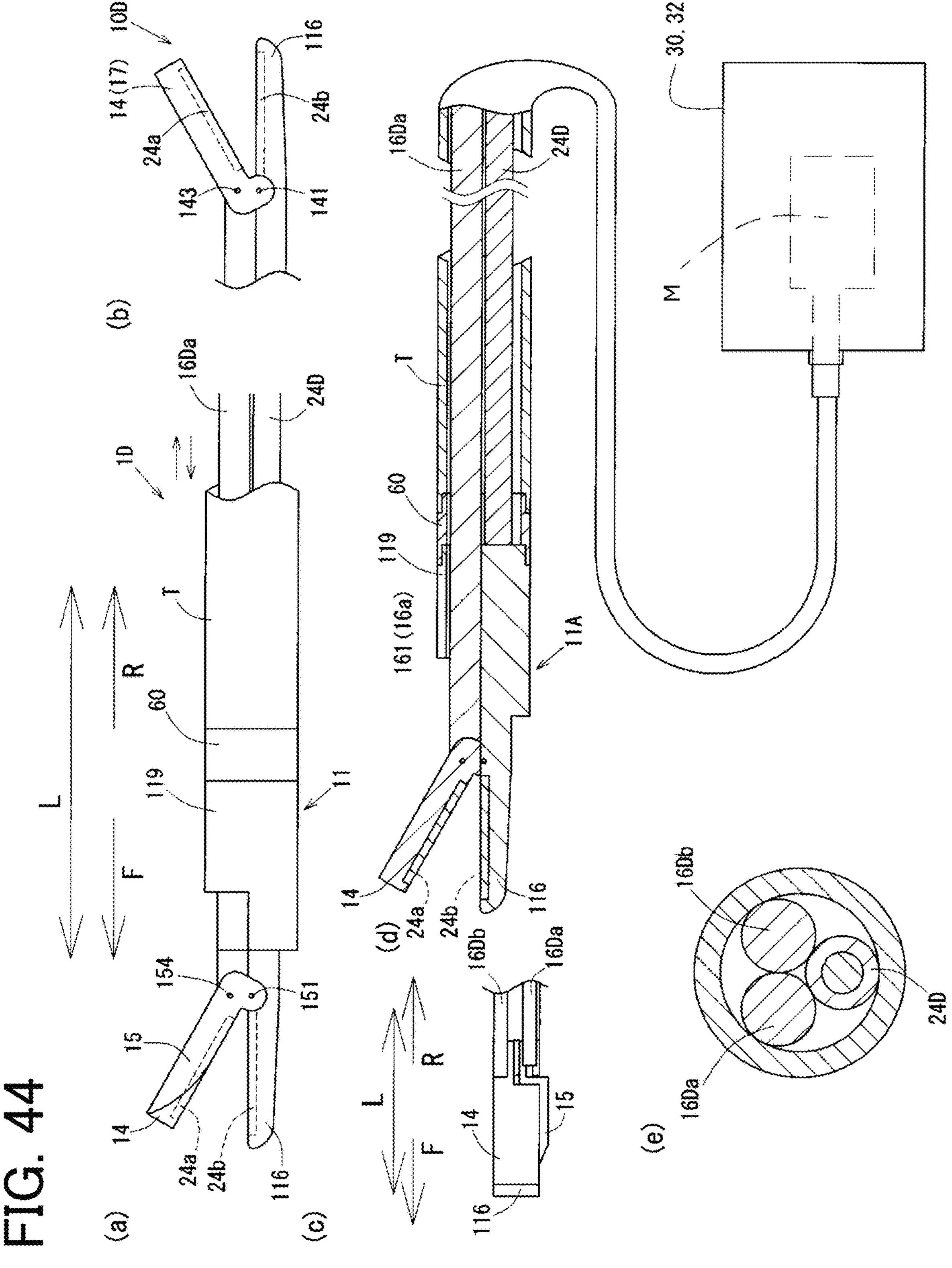
FIG. 44 is a schematic view of forceps in another embodiment.

As another embodiment, FIG. 44 shows a configuration diagram of forceps 1D. 44 at (a) shows a rear view of the forceps 1D, FIG. 44 at (b) shows a front view of the end effector portion 10D at the tip of the forceps 1D, and FIG. 44 at (c) shows the end shown in FIG. 44 at (a). A plane view of the effector portion 10D is shown, FIG. 44 at (d) shows a partial cross-sectional external view of the forceps 1D, and FIG. 44 at (e) shows a cross-sectional view of a tube T connecting the forceps 1D and the driving unit 32.

A drive unit or driving unit 32 for driving and controlling the forceps 1D is provided, and the forceps 1D and the driving unit 32 rotate a drive wire 16Da and a cutter 15 for rotating the upper jaw portion 14 inserted in a flexible tube T. The driving wire 16Db to be moved is connected by a coaxial cable 24D connected to the electrode 24*a* of the upper jaw portion 14 and the electrode 24*b* of the lower jaw portion 116.

The end effector portion 10D is composed of a fixed lower jaw portion 116, an upper jaw portion 14, and a cutter 15, and the base portion 11A of the main body frame 11 provided with the lower jaw portion 116 is attached to a fixture 60 provided at the tip of the tube T.

The tip of the drive wire 16Da is rotatably engaged with the base of the upper jaw portion 14 on the engaging shaft 143 which is pivotally supported by the rotating shaft 141 and is separated upward from the rotating shaft 141. When the drive wire 16Da moves to the tip side F, the engagement shaft 143 moves to the tip side F, and the upper jaw portion 14 pivotally supported by the rotation shaft 141 rotates in a direction close to the lower jaw portion 116. Then, the upper jaw portion 14 and the lower jaw portion 116 grip the object such as a living tissue. On the contrary, when the drive wire 16Da is moved to the proximal end side R, the upper jaw portion 14 is separated from the lower jaw portion 116 to eliminate the grip.

In FIG. 44 at (a) and (c), the cutter 15 is rotatably and independently attached to the upper jaw portion 14, and the base of the cutter 15 is shafted by a rotation shaft 151 provided in the lower jaw portion 116. The tip of the drive wire 16Db is rotatably engaged with the base of the cutter 15 on the engaging shaft 154 that is supported and separated upward from the rotating shaft 151.

When the drive wire 16Db moves to the tip side F, the engagement shaft 154 moves to the tip side F, and the cutter 15 pivotally supported by the rotation shaft 151 rotates in a direction close to the lower jaw portion 116 to join and cut objects such as living tissue. On the contrary, when the drive wire 16Db is moved to the base end side R, the cutter 15 is separated from the lower jaw portion 116 and the cutting state is eliminated.

The central conductor of the coaxial cable 24D is connected to the electrode 24*a*, and the outer conductor is connected to the electrode 24*b*. However, the connection structure with both electrodes is not limited to this embodiment, and may be the electrode connection structure of the above-described embodiment is not limited. As shown in FIG. 44 at (d), the coaxial cable 24D is led out from the forceps 1D together with the drive wires 16Da and Db to be inserted into the hollow portion of the tube T, and is connected to the driving unit 32.

The driving unit 32 is provided with a circuit for supplying electromagnetic waves, microwaves, high radio frequencies, and currents to the electrodes 24*a* and 24*b*, and the drive wires 16Da and 16Db are selectively or simultaneously pushed in the forceps 1D direction based on an internal or external signal. A control unit capable of individually rotating and controlling the upper jaw portion 14 and the cutter 15 by pulling in a direction away from the forceps 1D is provided. A micromotor M is built in the driving unit 32, and the upper jaw portion 14 and the cutter 15 may be individually rotated and driven by an electric signal.

According to this embodiment, since the end effector portion 10D has a simple structure that does not require a differential mechanism such as a spring or a gear, it is possible to prevent malfunction due to the entry of living tissue, and in particular, it is extremely fine with a diameter of several millimeters. Suitable for forceps. As shown in FIG. 24 at (e), the drive wires 16Da and 16Db are forced to move in the traveling direction by crawling the inner wall of the tube T, and are suitable for forceps of an endoscope. Both the tube T and the drive wire 16D are made of flexible material, but the wire may be made of a long thin plate member, and may be made of a rigid material if necessary.

By incorporating the function of the driving unit 32 into the driving unit 224 of the medical device shown in FIG. 45 or the irradiation/driving unit 2 of the surgical device shown in FIG. 47, it comes possible to easily provide multiple functions such as drilling function, gripping function, crashing function, coagulation function, cutting function, and opening or widening function.

Figure 49:
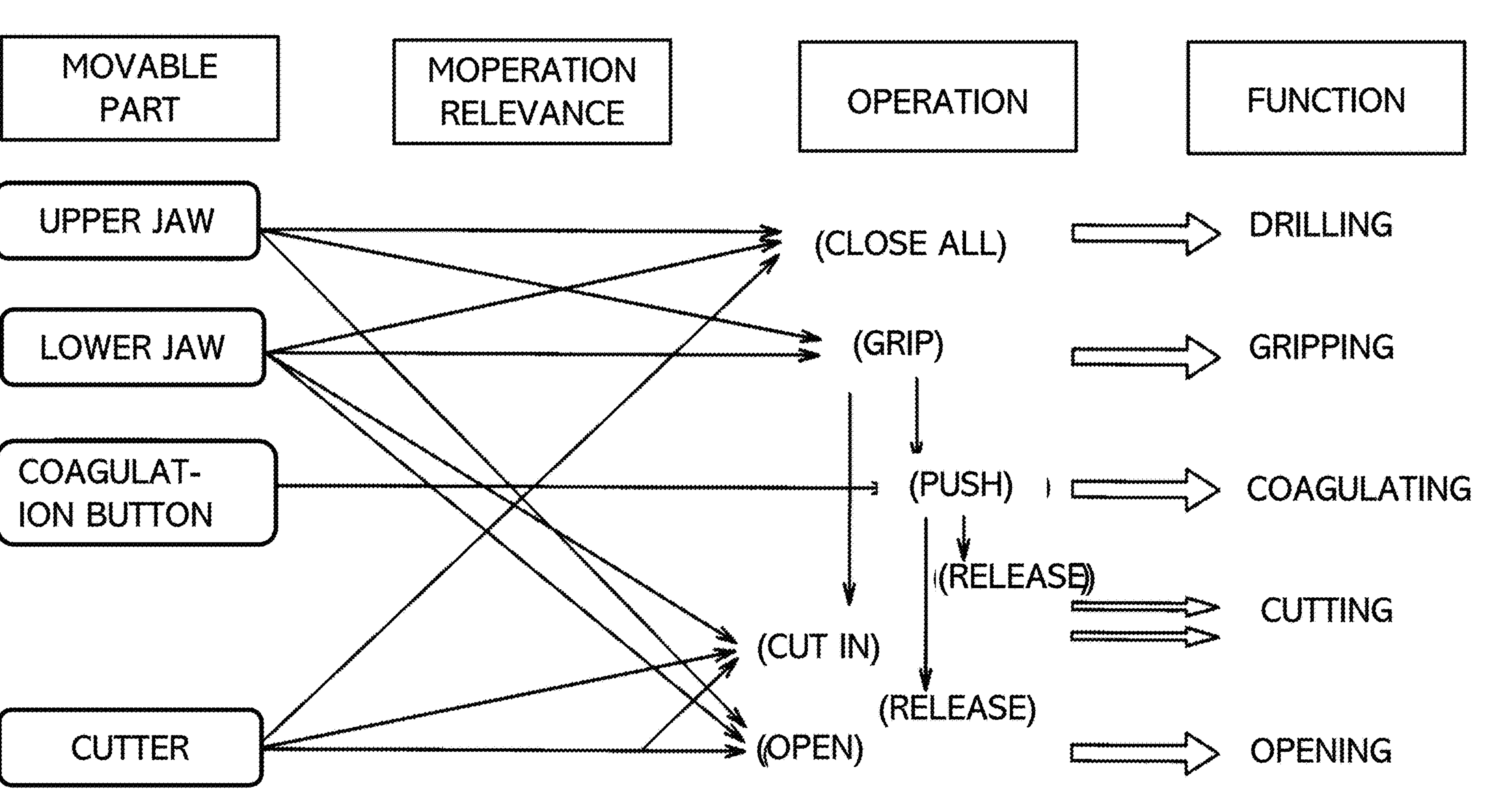
FIG. 49 is a schematic functional configuration diagram of forceps in another embodiment.

For example, in step S5 in the flowchart of FIG. 48, when the end effector portion 10D of this embodiment is applied to the end effector 10*c* of the tool 217 of FIG. 47, the upper jaw portion 14 and the cutter 15 are easily and independently driven. Therefore, as shown in FIG. 49, (1) The upper jaw, lower jaw, and cutter are all closed to provide a drilling function.

(2) To provide a gripping (or crashing) function by aligning the upper and lower jaws.

(3) In the second gripping function state, the coagulation button is operated to provide the coagulating function.

(4) Providing a cutting function by operating a cutter, (5) The opening (or widening) and closing function is provided by opening and closing the upper and lower jaws.

This makes it possible to provide a multifunctional forceps function with a single forceps tool 217 at the surgical site without replacement.

Alternatively, the medical device 220 of FIG. 45 may be provided with the forceps 1D of FIG. 44 and an operation unit 223A having five operation buttons associated with the above five functions (1) to (5) respectively to represent the design of FIG. 49. The five functions may be designed to be performed by a smartphone handled by operator.

That is, an end effector having a gripping mechanism and a cutting mechanism, and a driving unit for driving the end effector are provided, and the gripping mechanism includes a first gripping member and a second gripping member assembled so as to be openable and closable. The cutting mechanism has a gripping member rotating mechanism for rotating the first gripping member toward the second gripping member, and the cutting mechanism includes a cutting portion provided in the first gripping member and the cutting portion. The driving unit has a cutting portion rotating mechanism that rotates in the same direction as the rotation of the first gripping member, and the driving unit is driven by combining the first gripping member, the second gripping member, and the cutting portion. A medical tool that selectively provides at least one of a drilling function, a gripping function, a coagulation function, a cutting function, and an opening/closing function can be provided. The medical tool may be used alone, or it can be used for a medical robot driven by a control signal from the robot. In addition, when the grip and the grip are all closed and integrated, it can be used for opening a window, and when one of the grip and the grip is opened as a unit from this state, it can be used for opening and discharging, and all surgical operations are recorded in the robot. It is also possible to perform surgery using the function of artificial intelligence (AI). The end effector of the robot is provided with an electrode structure having a function of irradiating the target site with microwaves in the gripping rotation mechanism and/or the cutting rotation mechanism as described in the above embodiments.

The above-mentioned examples and embodiments have been described for medical treatment such as forceps and medical instruments, but the present invention is not limited to the above description, and the target site is not only a part of an object but also a member. It may include a general-purpose cutting device capable of gripping/contacting and cutting the target member. Further, the energy wave irradiated from the electrode of the forceps is not limited to the microwave, and may include other electromagnetic waves and electric currents.

For example, as described above, in the cutting mechanism 10 and the end effector 10*c* of the forceps such as 1, 1X, and 1Y, the gripping mechanism 17 is configured by the lower jaw portion 116 and the upper jaw portion 14, and the target such as the blood vessel B gripped by the gripping mechanism 17. The portion was configured to be cut by the cutter 15, but as shown in FIG. 30 (*d*), the gripping mechanism 17 composed of the lower jaw portion 116 and the upper jaw portion 14 is provided on both sides of the cutter 15 and is provided. The target site during gripping by the set gripping mechanism 17 may be configured to be cut by the cutter 15.

Further, the horizontal movement of the forceps or the end effector of the present invention is not limited to the axial movement, and may be a structure connected by a wire in order to increase the degree of freedom in the position and angle of the end effector. The spring mechanism for moving the upper jaw portion and the cutter for gripping, coagulating, and cutting the living tissue is not limited to the embodiment, and may be provided at any position.

Further, other than the electrodes and the cutting edge, insulation coating may be appropriately performed to prevent corrosion and sparks. In the above embodiment, the tissue between the upper jaw portion 14 and the cutter 15 and the lower jaw portion 116 can be coagulated from both sides. The split portion of the coaxial cable that supplies microwaves to the end effector enables a structure that does not restrict the movement of multiple joints and sends energy beyond multiple robot joints with a flexible cable.

Also, by using a metal blade, the rigidity and shape can be freely designed. The medical device having the forceps and end effector of the present invention can be used under MR image guidance, and microwave energy can be introduced not only under a microscope or a robot hand but also into endovascular surgery and fetal surgery.

In the above embodiment, the tissue between the upper jaw portion 14 and the cutter 15 and the lower jaw portion 116 can be coagulated from both sides. The split portion of the coaxial cable that supplies microwaves to the end effector makes it possible to send energy beyond multiple robot joints with a flexible cable without restricting the movement of multiple joints.

Also, by using a metal blade, the rigidity and shape can be freely designed. The medical device having the forceps and end effector of the present invention can be used under MR image guidance, and microwave energy can be introduced not only under a microscope or a robot hand but also into endovascular surgery and fetal surgery.

It is clear that the forceps and end effectors of the above embodiment may be easily replaced with the forceps and end effectors of the above medical devices, and remote surgery systems.

further the forceps of the above embodiments, medical devices with end effectors, and remote surgery systems may be provided.

FIG. 45 shows a medical device 220 according to another embodiment of the present invention. In FIG. 45 at (a), the medical device 220 includes a surgical device 221 that drives the end effector 10*c* of the multifunctional surgical device (medical processing tool) as described with FIGS. 40 to 43. If desired, as described above, the medical device 220 may be provided with the forceps 1D of FIG. 44 and an operation unit 223A having five operation buttons assigned to the five functions: drilling, gripping (or crashing), coagulating, cutting, and opening, respectively to represent the design of FIG. 49.

The surgical apparatus 221 includes a microwave irradiation module 222 including a microwave control circuit such as an irradiator and an amplifier, and a driving unit 224 of a mechanical mechanism that drives the end effector 10*c* by manual operation of the lever 223. Specifically, the trigger handle 13 of the forceps shown in FIGS. 1 to 15 and FIGS. 25 to 37 may be used as the lever 223, and the mechanical mechanism from the trigger handle 13 to the end effector 10*c* may be incorporated into the surgical apparatus 221.

The microwave irradiation module 222 having an irradiator is provided in the surgical apparatus 221 but, if necessary, inside the shaft portion 225 or in the bent portion 226 having a wrist function (such as the flexible portion 101 in FIG. 40). Alternatively, by providing the end effector 10*c* (the electronic module 31 of FIG. 16, FIG. 25, or FIG. 40 at (a)), the medical device 220 may be miniaturized.

The driving unit 224 operates the end effector 10*c* of FIG. 16 via the shaft portion 225 by the operator manually gripping and operating the lever 223 of the gripping member of the surgical apparatus 221.

The surgical apparatus 221 receives power from the adapter 227. The microwave irradiation module 222 included in the surgical apparatus 221 may be configured to be directly or indirectly connected to an irradiator installed in the robot body in addition to the conventional stationary type, shoulder-mounted type, and built-in type.

In the above embodiment, the microwave irradiation does not coagulate when gripped by the lower jaw portion 116 and the upper jaw portion 14 of the end effector 10*c*, but at the target site when the upper jaw portion 14 rotates with respect to the lower jaw portion 116. Even if a certain biological tissue is coagulated, the coagulation and hemostasis of the tissue can be cut. Further, when the biological tissue is gripped by the gripping mechanism 17*a* in the end effector 10*c* and cut by the cutter 15, microwaves may be irradiated.

With such forceps, the tissue can be opened and removed, griped to remove obstacles, and the gripping function can be used for the operation of maintaining the surgical field. Moreover, the part to be coagulated and cut can be griped with forceps and coagulated and cut as it is. It is possible to do. The operations of coagulation and cutting do not require re-gripping or re-pinching a plurality of tissues, but the operation is completed by gripping the pinched tissue once. Therefore, surgical operations can be performed with one device for gripping, coagulation, and cutting.

It is all the operation of general extraction surgery, and the extraction operation can be completed with a single instrument, and there is no need to replace it with another instrument.

As a modification of this embodiment, the microwave irradiation module 222 may be provided with an execution program memory, and the driving unit 224 may be an electric mechanical mechanism controlled by the execution program. As an operation, when the lever 223 is gripped, the execution program moves the driving unit 224 based on the position data of the lever 223, and the end effector 10*c* in FIG. 40 is configured to form the upper jaw wire 16*a* and the cutter wire. By moving each of 16*b*, the upper jaw portion 14 is rotated in the direction of the lower jaw portion 116, a microwave signal is sent to the irradiation electrode 24 by the above program, and the living tissue is coagulated by irradiating the microwave thereto.

Further, when the lever 223 is gripped, the proximity side wire 161 of the upper jaw wire 16*a* moves in the tensile direction according to the program according to the position data as described above, and the biological tissue can be gripped by the upper jaw portion 14*a* and the lower jaw portion 116*a*. can.

Furthermore, when the lever 223 is gripped, the near-side wire 161 of the cutter wire 16*b* moves in the tensile direction according to the position data of the lever, and only the cutter 15 is rotated to coagulate the living tissue and cut the coagulated living tissue. By releasing the lever 223 after cutting, the medical device 220 is configured to return to the initial state (open state) based on the position data of the lever.

The rotation position of the upper jaw portion 14 and the cutter 15 with respect to the lower jaw portion 116, the rotation of the pinion gear 12, and the position of the trigger handles 13 (13*a*, 13*b*) with respect to the fixed handle frame 111 are detected, and the detection signal based on the detection result is detected. It may be configured to receive and detect the state of the cutting mechanism 10 and the gripping mechanism 17.

FIG. 45 at (b) is a schematic diagram of a surgical system provided with a plurality of medical devices 220 illustrated in FIG. 45 at (a), and the internal configuration of each is the same as that of FIG. 45 at (a), but the medical device 220. Each microwave irradiation module 222 further includes a unit that synchronizes the wavelengths of the microwaves of each other, and synchronizes via the adapter 227 or wirelessly.

Therefore, when two medical devices 220 are operated in a patient by one or two operators, the wavelengths of both microwaves are synchronized, so that sparks or the like occur between the two medical devices 220. It can be prevented and safety is increased.

Figure 46:
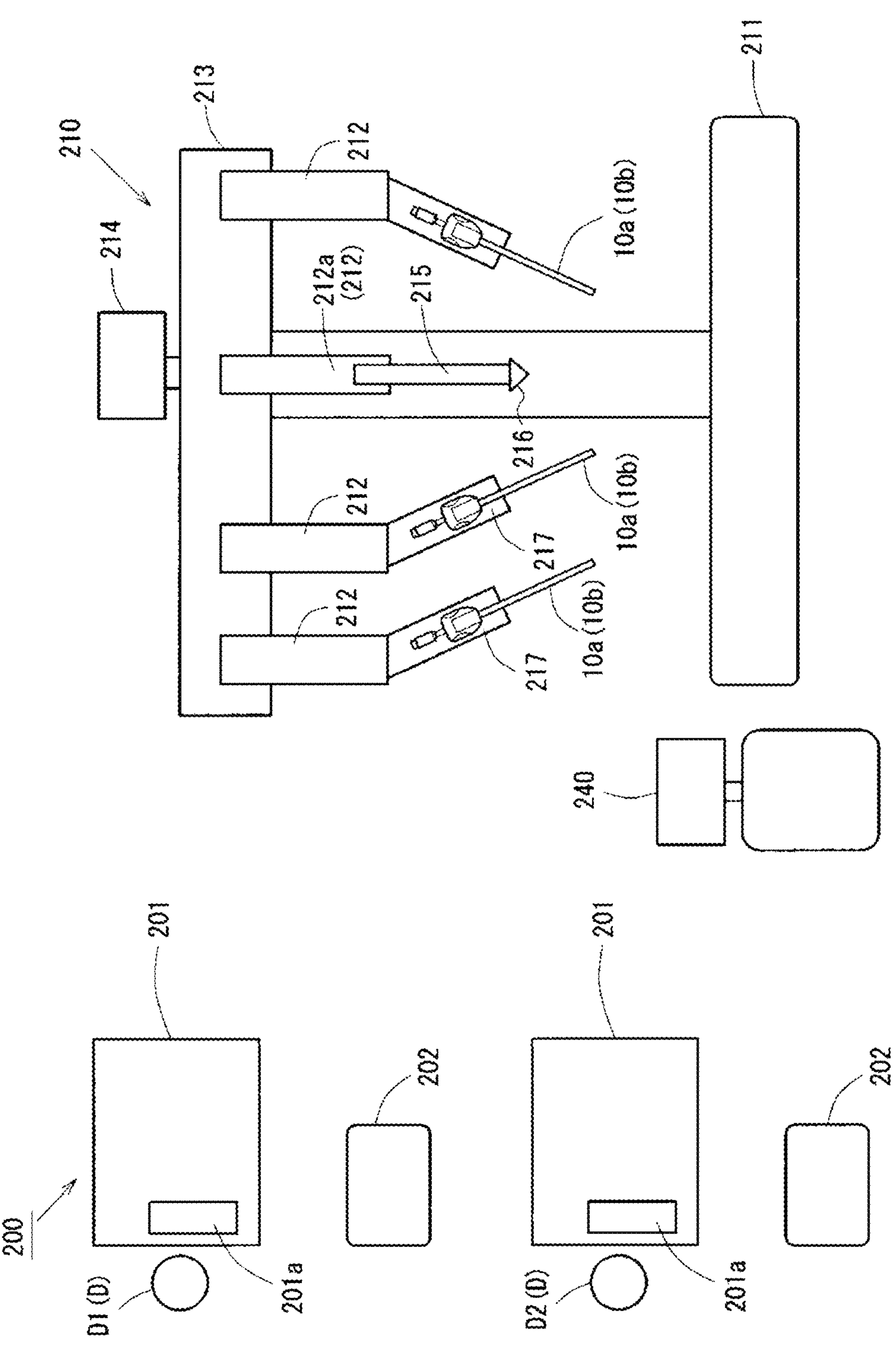
FIG. 46 is a schematic diagram of a remote surgery system in another embodiment.

FIG. 46 shows the remote surgery system 200 in one embodiment of the present invention. The remote surgery system 200 is a surgeon console 201 that serves as a station for each of the two operators D (D1 and D2), a master control unit 202 operated by the operator D, a viewing angle/core cart 240, and a patient-side cart. It has a robot of patient-side cart 210.

The surgeon console 201 includes a viewer 201*a* in which an image of the surgical site is displayed on the operator D. When using the surgeon console 201, operators D1 and/or D2 generally sit in the chair of the surgeon console, align their eyes in front of the viewer 201*a*, and grab the master control unit 202 in one hand.

In the remote surgery system 200, two operators can operate at the same time, but even one operator can operate it. When two operators operate at the same time, the two operators can operate in cooperation with each other, which has an advantage that the operation time of the entire patient can be shortened. The surgeon console 201 and the master control unit 202 may be provided in a system in which three or more units are provided, if necessary.

The robot of the patient-side cart 210 is arranged adjacent to the patient. During use, the patient-side cart 210 is placed near the patient in need of surgery. The robot of the patient-side cart 210 is provided with casters on the pedestal 211 so that it can be fixed but moved during surgery. The surgeon console 201 is used in the same operating room as the patient cart, but may be installed remotely from the patient cart 210.

The patient-side cart 210 includes four robot arm assemblies 212, but the number of robot arm assemblies 212 is arbitrary. Each robot arm assembly 212 has a structure that is connected to a drive device 213 that enables three-dimensional movement and is driven and controlled.

Display 214 displays image data related to surgery. The drive device 213 is controlled by the master control unit 202 of the surgeon console 201. The movement of the manipulator portion of the robot arm assembly 212 is controlled by the operation of the master control unit 202.

An image acquisition device 215 such as an endoscope is arranged in the robot arm assembly 212*a*, which is one of the four robot arm assemblies 212. A visual camera 216 is included at the remote end of the image capture device 215. The elongated shaft-shaped image capture device 215 allows the visual camera 216 to be inserted through the surgical entry port of the patient (not shown).

The image capture device 215 is operably connected to the viewer 201*a* of the surgeon console 201 to display the image captured by its visual camera 216.

Each of the other robot arm assemblies 212 is a linking device that supports and includes tools 217, which are removable surgical instruments, respectively. The tools 217 of the robot arm assembly 212 each include an end effector 10*c*.

Tool 217 has an elongated shaft that allows the end effector 10*c* to be inserted through the patient's surgical entry port. The movement of the end effector 10*c* is controlled by the master control unit 202 of the surgeon console 201.

When a microwave irradiation electrode (20, 24) and a microwave irradiation unit are used for the end effector 10*c* as the tool 217, the wavelengths of the microwaves emitted from the end effector 10*c* are synchronized with each other.

For example, when one or two operators D operate a plurality of tools 217 in a patient, the wavelengths of the irradiated microwaves are synchronized, so that the plurality of tools 217 or a plurality of end effectors 10*c* are synchronized. It is possible to prevent the occurrence of sparks between them, and safety is enhanced. Operating a plurality of end effectors 10*c* at the same time can shorten not only advanced surgery but also surgery time.

FIG. 47 shows the configuration of a tool 217 that is mounted on the robot arm assembly 212 of the remote surgery system 200 of FIG. 46 as a representative example of a surgical device. The tool 217 mounted on the other robot arm assembly 212 may have the same configuration or may be a surgical device having another configuration.

FIG. 47 at (a) shows a plane view of the tool 217. The tool 217 has an end effector 10*c* of a multifunctional surgical device, a bending portion 226, a shaft portion 225, a surgical device 221 for driving, controlling and monitoring the tool 217, and a connector 228 for connecting to a robot. The bent portion 226 increases the degree of freedom in the operation angle of the effector, and improves the accuracy of robot control.

FIG. 47 at (b) shows the internal configuration of the tool 217 of FIG. 47 at (a). FIG. 16 shows a medical system composed of a surgical device 221 that drives an end effector 10*c* directly connected to a slide shaft via a shaft portion 225 and a robot of a patient-side cart 210 that controls the surgical device 221.

The end effector 10*c* includes a cutting device having a rotatable upper jaw portion 14 and a lower jaw portion 116 held openable and closable, and a movable cutter 15 attached to the upper jaw portion 14 and the lower jaw portion 116. The surgical apparatus 221 connected to the end effector 10*c* is a matching unit with the tool 217, a reflected wave monitor 232, a control circuit for controlling signals in the surgical apparatus 233, and a cutting device of the tool 217 via a shaft portion 225 of the tool 217. It has an irradiation/driving unit 234 having an amplifier for mechanically driving the operation and a microwave generator, and a signal interface 235 with the robot of the patient-side cart 210.

As described in FIG. 48, the robot of the patient-side cart 210 is connected to the surgical device 221 via the signal interface 235 and the connector 228 by wire and/or wirelessly, and is connected to the robot of the patient-side cart 210. Inside, an input unit 210*a* that receives an operation signal from the master control unit 202, an arithmetic unit CPU that executes a predetermined operation program based on the operation signal, and a surgical apparatus 221 based on the output from the arithmetic unit. An output unit 210*a* that generates a drive signal for driving the upper jaw portion 14 and the cutter 15 of the end effector 10*c* is provided. The input unit and the output unit are composed of an input/output unit 210*a* (I/O).

FIG. 48 is an explanatory diagram of the remote surgery system 200, FIG. 48 at (a) is a block diagram showing a connection relationship with each unit, and FIG. 48 at (b) is an operation flow diagram of the remote surgery system 200.

The visual/core cart 240 has functions related to the image acquisition device. When the remote surgery system 200 is activated for surgery, the surgeon operates the master control unit 202 of the surgeon console 201, and if there are two surgeons, also operates the master control unit 202 of the surgeon console 201 (step S1). The command generated by the operation is transmitted to the visual core cart 240 (step S2).

The visual core cart 240 then interprets the signal and moves the desired robot arm assembly 212 to the patient's surgical area (step S3).

Next, the tool 217 attached to the selected robot arm assembly 212 is inserted into the patient through an elongated pipe (step S4), and the end effector 10*c* of the above embodiment is operated to grip, coagulate, and cut the tissue. (Step S5), the operation of the living tissue is completed.

The operation of gripping, coagulating, and cutting the biological tissue in step S5 is the operation of the end effector 10*c*, but there are three operation patterns: a first operation of coagulating, gripping, and cutting the biological tissue while irradiating microwaves from the electrode; a second operation of gripping a living tissue, irradiating microwaves from the electrode to the living tissue to coagulate after gripping, and cutting while irradiating the microwaves; and a third operation in which the irradiation of microwaves from the electrode is stopped and cut the living tissue though the living tissue is gripped and coagulated while irradiating the microwaves to the living tissue from the electrode. These three movement patterns are configured to be selectively available according to the surgical content. Further, it may be a pattern that is shared and operated by a plurality of tools of FIG. 21, such as being gripped or solidified by the tool 217 and cut by another tool 217.

The operation of coagulation/gripping/crashing/cutting of the tissue in this embodiment is controlled by the robot 210 instead of the control operation of the end effector 10*c* based on the position data of the lever 223 described as a modification of the embodiment of FIG. 45. By operating the end effector 10*c* based on the signal, the same control operation flow can be obtained.

That is, a gripping mechanism having a first gripping member and a second gripping member assembled so as to be openable and closable, and a gripping member rotating mechanism for rotating the first gripping member toward the second gripping member, and the above-mentioned. A cutting mechanism having a cutting portion provided in the first gripping member and a cutting portion rotating mechanism for rotating the cutting portion in the same direction as the rotation of the first gripping member is provided, and the second gripping member is provided. On the other hand, a driving unit is provided with a rotation shaft that rotatably supports the first gripping member and the cut portion, and independently drives the gripping member rotating mechanism and the cutting portion rotating mechanism while irradiating microwaves from the electrode to the living tissue to coagulate it. By applying a drive signal to the driving unit, it is possible to provide a medical system having a medical robot configured to coagulate and cut the target site while gripping the target site.

For example, in step S5 in the flowchart of FIG. 48, when the end effector portion 10D of this embodiment is applied to the end effector 10*c* of the tool 217 of FIG. 47, the upper jaw portion 14 and the cutter 15 are easily and independently driven. Therefore, as shown in FIG. 49, (1) The upper jaw, lower jaw, and cutter are all closed to provide a drilling function.

(2) To provide a gripping function by aligning the upper and lower jaws.

(3) In the second gripping function state, the coagulation button is operated to provide the coagulating function.

(4) Providing a cutting function by operating a cutter, (5) The opening (widening) function is provided by opening and closing the upper and lower jaws.

This makes it possible to provide a multifunctional forceps function with a single forceps tool 217 at the surgical site without replacement.

That is, an end effector having a gripping mechanism and a cutting mechanism, and a driving unit for driving the end effector are provided, and the gripping mechanism includes a first gripping member and a second gripping member assembled so as to be openable and closable, and a gripping rotation mechanism that rotates the first gripping member toward the second gripping member, and the cutting mechanism includes a cutting member attached to the first gripping member and the cutting member and a cutting rotation mechanism that rotates in the same direction as the rotation of the gripping member, and the driving unit driving the first gripping member, the second gripping member, and the cutting member in combination. Thus, it is possible to provide a medical tool that selectively provides at least one of a function, a gripping function, a crashing function, a coagulation function, a cutting function, and an opening function. The medical tool may be used alone, or it can be used for a medical robot driven by a control signal from the robot. Also, when the gripping member and the cutting member are all closed and integrated, it can be used for opening a window, and when one of the cutting member and the gripping member is opened integrally from this state, it can be used for opening and closing, and all surgical operations are recorded in the robot. It is also possible to perform surgery using the function of artificial intelligence (AI).

The above-mentioned examples and embodiments have been described for medical treatment such as forceps and medical instruments, but the present invention is not limited to the above description, and the target site is not only a part of an object but also a member. That is, the term "target site" shall include any "target portion". In other words "target portion" shall include any "target site". It may include a general-purpose cutting device capable of gripping/contacting and cutting the target member. Further, the energy wave irradiated from the electrode of the forceps is not limited to the microwave, and may include other electromagnetic waves and electric currents.

For example, as described above, in the cutting mechanism 10 and the end effector 10*c* of the forceps 1, 1X, 1Y and the like, the gripping mechanism 17 is configured by the lower jaw portion 116 and the upper jaw portion 14, and the target site such as the blood vessel B is gripped by the gripping mechanism 17 which is configured to cut the target site by the cutter 15, but as shown in FIG. 30 at (d), the gripping mechanism 17 may be composed of the lower jaw portion 116 and the upper jaw portion 14 provided on both sides of the cutter 15 and is provided. The target site during gripping by the set gripping mechanism 17 may be designed to be cut by the cutter 15.

Further, the horizontal movement of the forceps or the end effector of the present invention is not limited to the axial movement, and may be a structure connected by a wire in order to increase the degree of freedom in the position and angle of the end effector. The spring mechanism for moving the upper jaw portion and the cutter for gripping, coagulating, and cutting the living tissue is not limited to the embodiment, and may be provided at any position.

Further, other than the electrodes and the cutting edge, insulation coating may be appropriately performed to prevent corrosion and sparks. In the above embodiment, the tissue between the upper jaw portion 14 and the cutter 15 and the lower jaw portion 116 can be coagulated from both sides. The split portion of the coaxial cable that supplies microwaves to the end effector enables a structure that does not restrict the movement of multiple joints and sends energy beyond multiple robot joints with a flexible cable.

Also, by using a metal blade, the rigidity and shape can be freely designed. The medical device having the forceps and end effector of the present invention can be used under MR image guidance, and microwave energy can be introduced not only under a microscope or a robot hand but also into endovascular surgery and fetal surgery.

In the above embodiment, the tissue between the upper jaw portion 14 and the cutter 15 and the lower jaw portion 116 may be coagulated from both sides. The split portion of the coaxial cable that supplies microwaves to the end effector makes it possible to send energy beyond multiple robot joints with a flexible cable without restricting the movement of multiple joints.

Also, by using a metal blade, the rigidity and shape can be freely designed. The medical device having the forceps and end effector of the present invention can be used under MR image guidance, and microwave energy can be introduced not only under a microscope or a robot hand but also into endovascular surgery and fetal surgery.

The forceps and end effectors of the above embodiment can be easily replaced with the forceps and end effectors of the above-mentioned medical device and remote surgery system, and the forceps and end effectors of the above embodiment can be easily replaced with the above-mentioned medical devices and remote surgery systems.

Further, the gripping operation of the operation of gripping/coagulating the target site in the above embodiment may include the operation of gripping and crashing the target site as necessary, and the gripping/coagulation includes the operation of gripping, crashing, and coagulating.

The embodiments of the present invention are exemplified in all respects, and the scope of the present invention includes all modifications within the meaning and scope equivalent to the scope of claims.

What is claimed is:

1. A cutting device comprising:

a contact mechanism, including at least a first contact member and a second contact member, configured to rotate the first contact member toward the second contact member to bring the first contact member and the second contact member into contact with a living tissue, and a cutting mechanism, including at least a cutter, that is configured to cut the living tissue in a state where the first contact member and the second contact member are in contact with the living tissue by the contact mechanism, wherein the first contact member and the second contact member are served as a first gripping member and a second gripping member that are both configured to grip the living tissue, and the contact mechanism is served as a gripping mechanism in which the first gripping member is rotated toward the second gripping member to grip the living tissue by the first contact member and the second contact member, wherein the cutting mechanism includes the cutter attached alongside an outermost lateral surface of the first gripping member and the second gripping member, and, in a state in which the living tissue is gripped by the first gripping member and the second gripping member of the gripping mechanism, the cutter is rotated along the outermost lateral surface of the first gripping member in the same direction as the rotation of the first gripping member, and joined to the second gripping member, thereby cutting the living tissue.

2. The cutting device according to claim 1, further comprising:

a driver that is configured to contact and grip the first gripping member and the second gripping member on the living tissue in the contact mechanism, wherein the cutter is configured to come into contact with the second gripping member to cut the living tissue by driving the driver, one operator configured to operate the driver and the cutting mechanism, and a differential mechanism, including at least a spring, configured to operate the gripping mechanism and the cutting mechanism until the living tissue is gripped therewith by an operation of the one operator, wherein the cutting mechanism is differentially operated to the gripping mechanism in a gripping state by further operation of the one operator.

3. A grip and cut method using the cutting device of claim 2, comprising:

operating the gripping mechanism and the cutting mechanism together until the living tissue is gripped by the first gripping member and the second gripping member in accordance with the operation by the one operator, and differentially operating the cutting mechanism relative to the gripping mechanism in a gripping state in which the living tissue is gripped by further operation of the one operator.

4. The cutting device according to claim 1, wherein the first gripping member is provided with a protrusion that regulates the cutter that rotates in the same direction to protrude beyond the first gripping member in the direction opposite to the cutting direction.

5. The cutting device according to claim 1, further comprising electrodes for irradiating electromagnetic waves disposed on a gripping portion that grips the living tissue in the first gripping member and in a vicinity of the cutter, and on a gripping portion that grips the living tissue in the second gripping member.

6. The cutting device according to claim 5, wherein at least one of the electrodes are a coaxial electrode provided with a center electrode and an outer electrode surrounding the center electrode via an insulator, and wherein a plurality of coaxial cables configured to connect an irradiation device for irradiating the electromagnetic waves and the electrodes are branched in parallel, and each of the coaxial electrodes is electrically connected to a central conductor and an outer conductor of the coaxial cable.

7. A forceps having the cutting device according to claim 5 in which the first gripping member and the second gripping member are a first jaw member and a second jaw member, respectively, further comprising:

a driver configured to grip and coagulate the biological tissue by rotating the first jaw member toward the second jaw member, and one operator configured to operate the driver and the cutting mechanism, wherein at least a part of the living tissue is coagulated by irradiating electromagnetic waves from the electrodes, and wherein the biological tissue is gripped by the first jaw member and the second jaw member, and then cut by the cutting mechanism in accordance with a series of operations of the one operation member.

8. The forceps according to claim 7 further including a differential mechanism configured to operate the gripping mechanism and the cutting mechanism together by the one operation member until the living tissue is gripped, and differentially operates the cutting mechanism relative to the gripping mechanism in a gripping state in which the living tissue is gripped by further operation of the one operator.

9. The forceps according to claim 7 further including a notifier configured to notify a user of the operation of the differential mechanism by a series of operations of the one operator.

10. An end effector including the cutting device according to claim 1, wherein the first contact member is a movable upper jaw member rotatably connected to a shaft, and the second gripping member is a stationary lower jaw member supported by a main body frame, and wherein the end effector comprises:

a first electrode provided on the surface of the upper jaw member facing the lower jaw member, a second electrode provided on the surface of the lower jaw member facing the upper jaw member, a third electrode provided at or near the cutting edge of the cutting member, a coaxial cable connected to the first electrode, the second electrode, and the third electrode, and a flexible member with a bendable cover shape.

11. The cutting device according to claim 1 including a notifier configured to notify at least one of the rotation of the first gripping member and the rotation of the cutter with respect to the second gripping member.

12. The cutting device according to claim 1 including electrodes which are disposed in at least one of a gripping portion that grips the living tissue in the first gripping member and a vicinity of the cutter, and a gripping portion that grips the living tissue in the second gripping member irradiating electromagnetic waves.

13. The cutting device according to claim 1, further comprising:

a reference frame with the second gripping member at its distal end, and a slide frame with the first gripping member at its distal end and sliding relative to the reference frame, wherein the first gripping member is pivotally supported at the distal end of the slide frame so as to be rotatable toward the second gripping member, wherein a tip support shaft is provided at the distal end side of the reference frame for pivotally supporting the first gripping member and the cutter, and wherein a spring is arranged along an outer surface of the first gripping member to bias the first gripping member and the cutter.

14. The cutting device according to claim 13, wherein the spring is configured to bias the first gripping member and the cutter in a rotational direction in which they move away from each other when the first gripping member and the cutter rotate toward each other around a support shaft provided at the distal end of the slide frame.

15. The cutting device according to claim 1, further comprising a differential mechanism including at least a reference frame with the second gripping member at its distal end that includes a first slide plate and a second slide plate that are arranged independently of each other with respect to the reference frame, wherein when the second slide plate is moved to its distal end side, the first gripping member pivots around a distal end support shaft provided on a distal end side in a direction approaching the second gripping member to grip the living tissue, wherein when the first slide plate is further moved to the distal end side, the cutter rotates along the outermost lateral surface of the first gripping member and pivots beyond an upper surface of the second gripping member, thereby cutting the gripped living tissue.

16. The cutting device according to claim 1, wherein the cutter is attached alongside the outermost lateral surface of the first gripping member and the second gripping member, the outermost lateral surface being an outermost surface in a direction orthogonal to an extension direction of the first gripping member.

17. The cutting device according to claim 16, wherein a width of the first gripping member overlaps an entire width of the second gripping member in a plan view of the cutting device.

18. The cutting device according to claim 1, wherein a width of the first gripping member overlaps an entire width of the second gripping member in a plan view of the cutting device.

19. The cutting device according to claim 1, further comprising a trigger handle for rotating the first gripping member and a fixed handle frame connected to the second gripping member, and a compression coil spring for automatic return provided between the fixed handle frame and the trigger handle.

20. The cutting device according to claim 1, wherein the cutter attached along the outermost lateral surface of the first gripping member and the second gripping member is rotatably supported by a shaft provided on the second gripping member.

21. The cutting device according to claim 1, wherein the cutter attached along the outermost lateral surface of the one side of the first gripping member and the second gripping member is rotatably supported by a shaft provided on the second gripping member, and is urged by a spring arranged along a front side of the first gripping member together with the first gripping member.

* * * * *